US 11,690,653 B2

United States Patent
Hyer et al.

(10) Patent No.: US 11,690,653 B2
(45) Date of Patent: Jul. 4, 2023

(54) FASTENING DEVICES, SYSTEMS, AND METHODS

(71) Applicant: RTG Scientific, LLC, Austin, TX (US)

(72) Inventors: Richard Justin Hyer, Hyrum, UT (US); Jonathan Bitter, Hyde Park, UT (US); Andrew Fauth, North Logan, UT (US)

(73) Assignee: RTG Scientific, LLC, Austin, TX (US)

( * ) Notice: Subject to any disclaimer, the term of this patent is extended or adjusted under 35 U.S.C. 154(b) by 0 days.

(21) Appl. No.: 17/555,389

(22) Filed: Dec. 18, 2021

(65) Prior Publication Data

US 2022/0249148 A1     Aug. 11, 2022

Related U.S. Application Data

(60) Provisional application No. 63/147,640, filed on Feb. 9, 2021.

(51) Int. Cl.
| | |
|---|---|
| *A61B 17/70* | (2006.01) |
| *A61B 17/86* | (2006.01) |
| *A61B 17/72* | (2006.01) |
| *A61F 2/40* | (2006.01) |
| *A61B 17/56* | (2006.01) |

(Continued)

(52) U.S. Cl.
CPC ........ *A61B 17/704* (2013.01); *A61B 17/7032* (2013.01); *A61B 17/7034* (2013.01);
(Continued)

(58) Field of Classification Search
CPC .............. A61B 17/8625; A61B 17/863; A61B 17/7032; A61B 17/7037; A61B 17/70; F16B 33/02

(Continued)

(56) References Cited

U.S. PATENT DOCUMENTS

| | | | |
|---|---|---|---|
| 5,964,768 | A | 10/1999 | Huebner |
| 8,337,205 | B2 | 12/2012 | Reed |

(Continued)

FOREIGN PATENT DOCUMENTS

| | | |
|---|---|---|
| WO | 2004098442 A1 | 11/2004 |
| WO | 2007074498 A2 | 7/2007 |
| WO | 2020224657 A1 | 11/2020 |

OTHER PUBLICATIONS

International Search Report and Written Opinion dated Apr. 25, 2022 for corresponding PCT Application No. PCT/US2021/060196.

(Continued)

*Primary Examiner* — Eduardo C Robert
*Assistant Examiner* — Michelle C Eckman
(74) *Attorney, Agent, or Firm* — David Meibos; Maywood IP Law

(57) ABSTRACT

A pedicle bone fastener may include a shaft, a helical thread, and an integrated attachment feature. The shaft may include a proximal end, a distal end, and a longitudinal axis. The helical thread may be disposed about the shaft along the longitudinal axis between the proximal and distal ends of the shaft. The helical thread may include a first undercut surface and a second undercut surface. The first undercut surface may be angled toward one of the proximal end and the distal end of the shaft and the second undercut surface may be angled toward the other one of the proximal end and the distal end of the shaft. The integrated attachment feature may be disposed at the proximal end of the shaft and configured to be adjustably secured to a spinal stabilization implement.

20 Claims, 29 Drawing Sheets

(51) Int. Cl.
   *A61B 17/00*    (2006.01)
   *A61F 2/30*     (2006.01)
   *A61B 17/68*    (2006.01)

(52) U.S. Cl.
   CPC ........ *A61B 17/7037* (2013.01); *A61B 17/725* (2013.01); *A61B 17/863* (2013.01); *A61B 17/8605* (2013.01); *A61B 17/8625* (2013.01); *A61F 2/4014* (2013.01); *A61F 2/4081* (2013.01); *A61B 2017/00477* (2013.01); *A61B 2017/00526* (2013.01); *A61B 2017/564* (2013.01); *A61B 2017/681* (2013.01); *A61F 2002/30332* (2013.01); *A61F 2220/0033* (2013.01)

(58) Field of Classification Search
   USPC .................................................. 411/411–412
   See application file for complete search history.

(56) References Cited

U.S. PATENT DOCUMENTS

| | | | |
|---|---|---|---|
| 8,602,781 B2 | 12/2013 | Reed | |
| 8,875,399 B2 | 11/2014 | Reed | |
| 9,079,263 B2 | 7/2015 | Reed | |
| 9,526,547 B2 | 12/2016 | Reed | |
| 9,687,319 B2 | 6/2017 | Reed | |
| 9,782,209 B2 | 10/2017 | Reed | |
| 9,901,379 B2 | 2/2018 | Reed | |
| 10,085,782 B2 | 10/2018 | Reed | |
| 10,441,385 B2 | 10/2019 | Reed | |
| 10,639,086 B2 | 5/2020 | Reed | |
| 2003/0088248 A1* | 5/2003 | Reed | A61B 17/863 606/308 |
| 2007/0233123 A1 | 10/2007 | Ahmad et al. | |
| 2009/0069852 A1* | 3/2009 | Farris | A61B 17/7038 606/301 |
| 2010/0121327 A1 | 5/2010 | Velikov | |
| 2014/0058460 A1* | 2/2014 | Reed | A61B 17/863 606/301 |
| 2014/0329202 A1 | 11/2014 | Zadeh | |
| 2018/0303529 A1 | 10/2018 | Zastrozna | |
| 2019/0223917 A1* | 7/2019 | Gray | A61B 17/7082 |
| 2021/0259842 A1 | 8/2021 | Feng et al. | |

OTHER PUBLICATIONS

International Search Report and Written Opinion dated Jul. 6, 2022 for corresponding PCT Application No. PCT/US2022/015866.

* cited by examiner

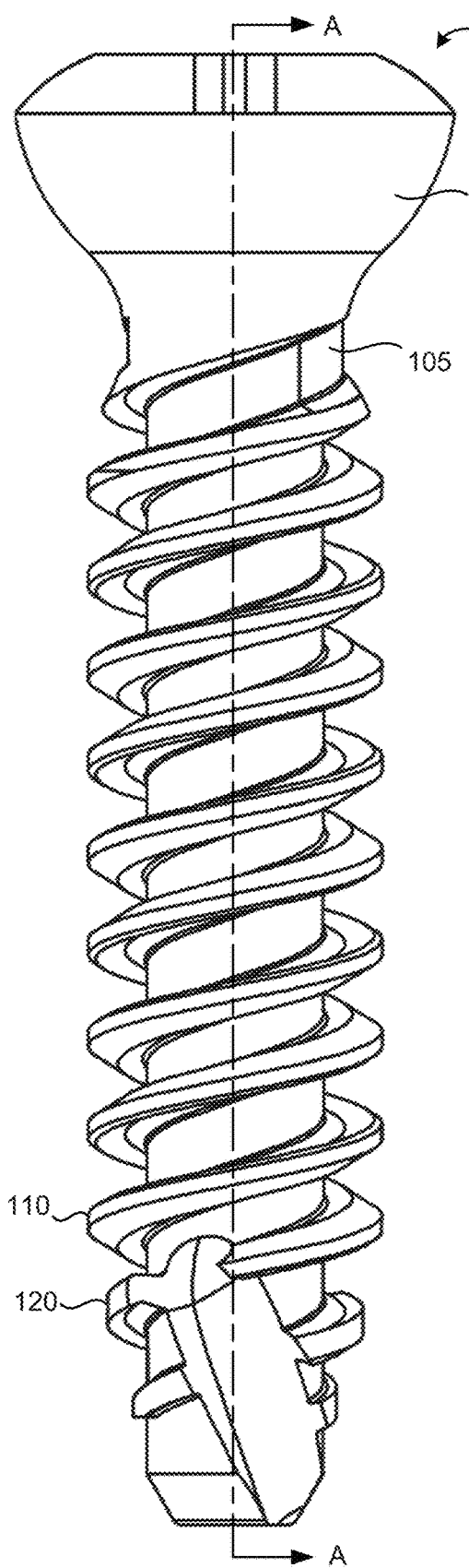
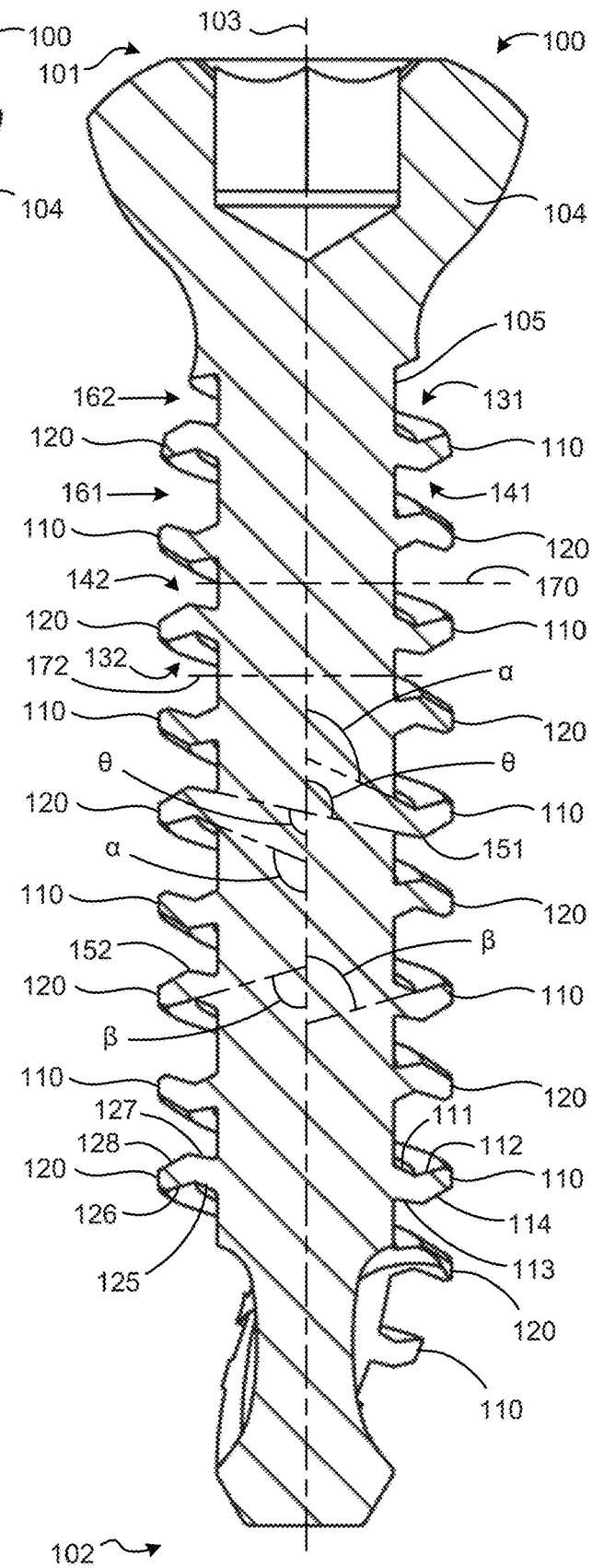
FIG. 1C  FIG. 1D

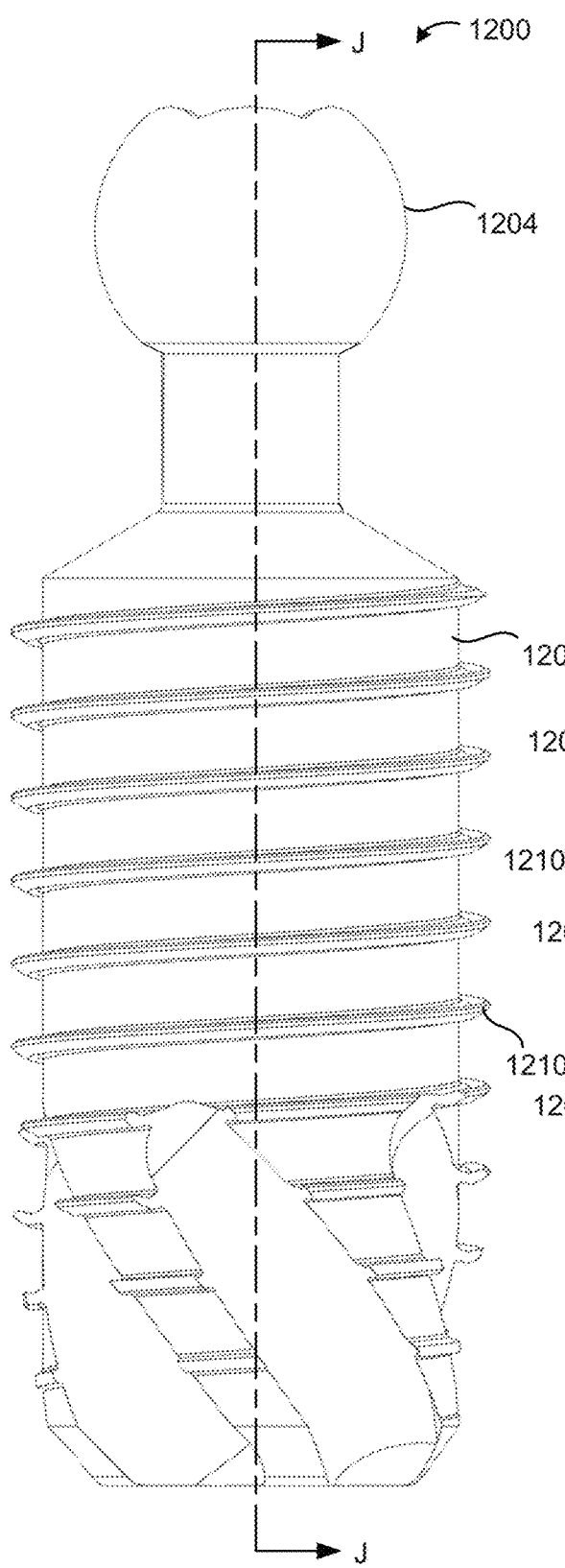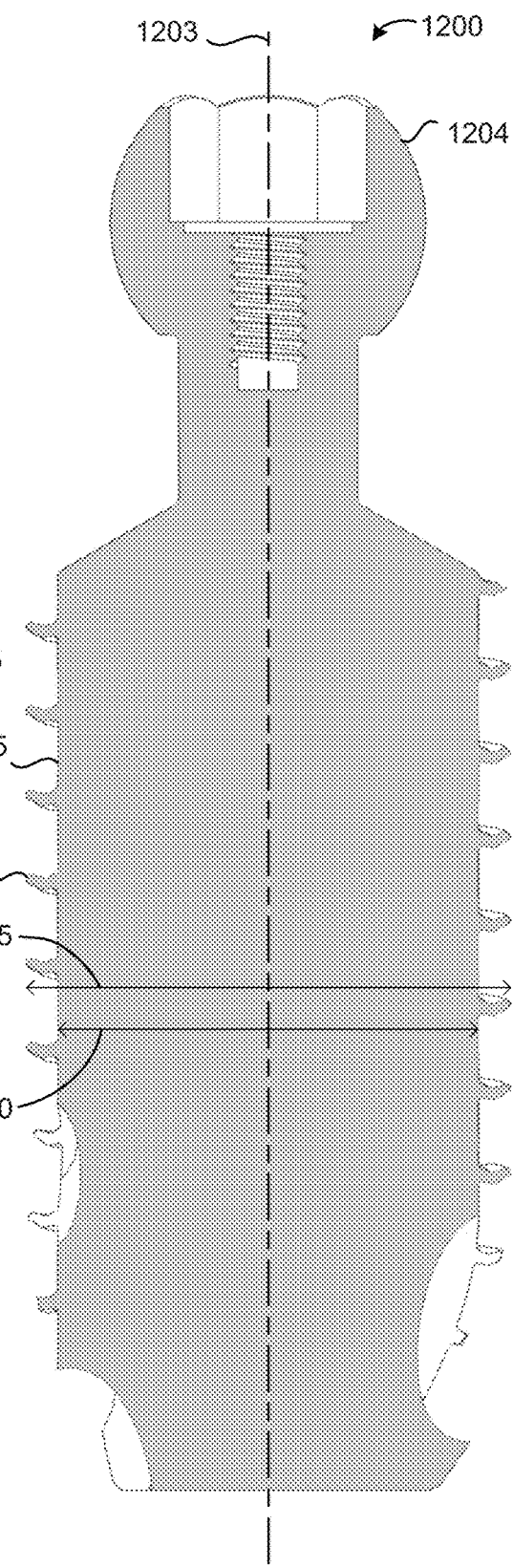
FIG. 12C
FIG. 12D

FASTENING DEVICES, SYSTEMS, AND METHODS

CROSS-REFERENCE TO RELATED APPLICATIONS

This application claims the benefit of U.S. Provisional Patent Application Ser. No. 63/147,640 filed on Feb. 9, 2021, entitled "FASTENING DEVICES, SYSTEMS, AND METHODS". The foregoing document is hereby incorporated by reference in its entirety.

TECHNICAL FIELD

The present disclosure relates to fastening devices, systems, and methods. More specifically, the present disclosure relates to fastening devices with improved thread designs and fastening systems/methods utilizing fastening devices with improved thread designs.

BACKGROUND

Surgical procedures involving fasteners implanted within bone and other tissues can become lose over time due to multi-axial forces and off-axis loading scenarios that may be applied to the fastener during the healing process. Traditional fastener thread designs may not provide sufficient fastener fixation to overcome these multi-axial forces and off-axis loading scenarios.

Accordingly, fasteners with improved thread designs for increasing bone fixation and load sharing between a bone/fastener interface experiencing multi-axial and off-loading conditions would be desirable.

SUMMARY

The various fastening devices, systems, and methods of the present disclosure have been developed in response to the present state of the art, and in particular, in response to the problems and needs in the art that have not yet been fully solved by currently available fastening devices, systems, and methods. In some embodiments, the fastening devices, systems, and methods of the present disclosure may provide improved bone fixation and load sharing between a bone/fastener interface under multi-axial and off-loading conditions.

In some embodiments, a pedicle bone fastener may include a shaft, a helical thread, and an integrated attachment feature. The shaft may include a proximal end, a distal end, and a longitudinal axis. The helical thread may be disposed about the shaft along the longitudinal axis between the proximal and distal ends of the shaft. The helical thread may include a first undercut surface and a second undercut surface. The first undercut surface may be angled toward one of the proximal end and the distal end of the shaft and the second undercut surface may be angled toward the other one of the proximal end and the distal end of the shaft. The integrated attachment feature may be disposed at the proximal end of the shaft and configured to be adjustably secured to a spinal stabilization implement.

In some embodiments, the integrated attachment feature may include a polyaxial head having a first semi-spherical surface configured to be polyaxially-adjustably secured to the spinal stabilization implement.

In some embodiments, the spinal stabilization implement may include a discrete tulip having a second semi-spherical surface configured to engage the first semi-spherical surface of the polyaxial head to polyaxially-adjustably secure the discrete tulip to the polyaxial head at any of a variety of relative orientations.

In some embodiments, the discrete tulip may include at least one opening and a locking member configured to secure a rod receivable through the at least one opening to the discrete tulip.

In some embodiments, the integrated attachment feature may include an integrated tulip having at least one opening configured to receive at least a part of the spinal stabilization implement therethrough.

In some embodiments, the integrated tulip further may include a locking member configured to secure the rod to the integrated tulip.

In some embodiments, a pedicle fastener stabilization system may include a pedicle bone fastener, a tulip, and a spinal stabilization rod. The pedicle bone fastener may include a shaft having a proximal end, a distal end, and a longitudinal axis. The pedicle bone fastener may also include a polyaxial head at the proximal end of the shaft. The pedicle bone fastener may also include a first helical thread disposed about the shaft along the longitudinal axis between the proximal and distal ends of the shaft. The first helical thread may include a first concave undercut surface. The pedicle bone fastener may also include a second helical thread disposed about the shaft adjacent the first helical thread. The second helical thread may include a second concave undercut surface. The first concave undercut surface and the second concave undercut surface may be angled towards one of the proximal end and the distal end of the shaft. The tulip may be configured to be polyaxially-adjustably secured to the polyaxial head, and the spinal stabilization rod may be securable to the tulip.

In some embodiments, the polyaxial head may be integrally formed with the pedicle bone fastener.

In some embodiments, the polyaxial head may include a first semi-spherical surface.

In some embodiments, the tulip may include a second semi-spherical surface configured to engage the first semi-spherical surface of the polyaxial head to polyaxially-adjustably secure the tulip to the polyaxial head at any of a variety of relative orientations.

In some embodiments, the tulip may include at least one opening configured to receive the spinal stabilization rod therethrough.

In some embodiments, the tulip may include a locking member configured to secure the spinal stabilization rod to the tulip.

In some embodiments, a minor diameter of the shaft may be constant.

In some embodiments, a method of implanting a bone fastener assembly may include: (1) inserting a bone fastener into a bone, (2) adjusting an orientation of an implement to a selected orientation relative to an attachment feature of the bone fastener, and (3) attaching the implement to the attachment feature at the selected orientation. The bone fastener may include a shaft, a helical thread, and the attachment feature. The shaft may include a proximal end, a distal end, and a longitudinal axis. The helical thread may be disposed about the shaft along the longitudinal axis between the proximal and distal ends of the shaft. The helical thread may include a first undercut surface and a second undercut surface. The first undercut surface may be angled toward one of the proximal end and the distal end of the shaft. The second undercut surface may be angled toward the other one of the proximal end and the distal end of the shaft. The attachment feature may be disposed at the proximal end of the shaft and configured to be adjustably secured to the implement.

In some embodiments, the attachment feature at the proximal end of the shaft may be configured to be polyaxially-adjustably secured to the implement. Adjusting the orientation of the implement to the selected orientation relative to the attachment feature may comprise polyaxially-adjusting the orientation of the implement to a selected relative orientation, of a plurality of polyaxially-differentiated potential relative orientations, relative to the attachment feature.

In some embodiments, the attachment feature may include a polyaxial head having a first semi-spherical surface, and the implement may include a discrete tulip having a second semi-spherical surface configured to engage the first semi-spherical surface of the polyaxial head to polyaxially-adjustably secure the discrete tulip to the polyaxial head at any of a variety of relative orientations.

In some embodiments, the discrete tulip may include at least one opening and a locking member configured to secure a rod received through the at least one opening to the discrete tulip.

In some embodiments, the method may also include drilling a pilot hole into the bone and inserting the shaft of the bone fastener into the pilot hole.

In some embodiments, the method may also include tapping a bone thread in the bone to form a tapped bone thread about the pilot hole and inserting the helical thread into the tapped bone thread.

These and other features and advantages of the present disclosure will become more fully apparent from the following description and appended claims or may be learned by the practice of the devices, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which:

FIG. 1C illustrates a side view of the fastener of FIG. 1A; FIG. 1D illustrates a cross-sectional side view of the fastener of FIG. 1A taken along the line A-A shown in FIG. 1C;

FIG. 12C illustrates a side view of the fastener of FIG. 12A; FIG. 12D illustrates a cross-sectional side view of the fastener of FIG. 12A taken along the line J-J shown in FIG. 12C.

Figure 1A:
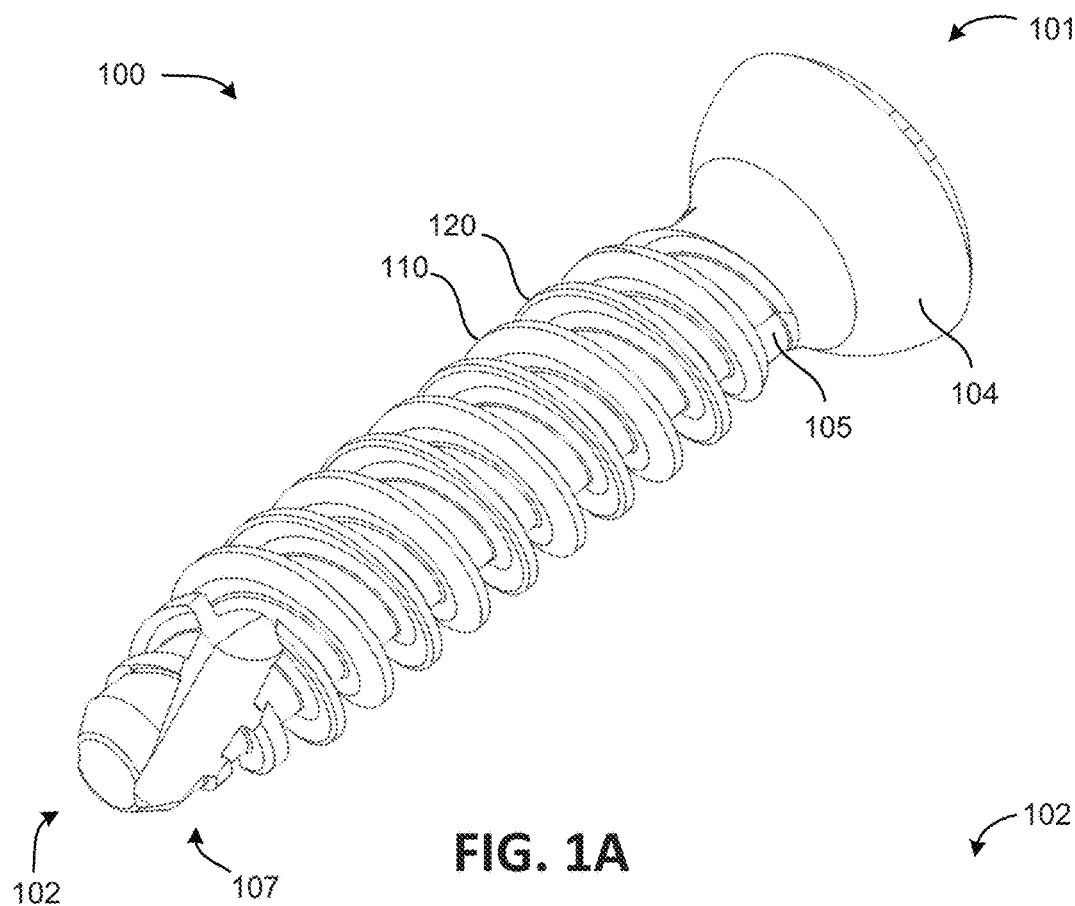
FIG. 1A illustrates a front perspective view of a fastener, according to an embodiment of the present disclosure.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the implants, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

The following disclosure presents various fasteners for utilization in bone and other tissues as implantable devices (e.g., orthopedic implants, spine implants, etc.) for the purpose of streamlining the present disclosure. However, it will be understood that the various fasteners and helical threading concepts presented herein can be utilized in any medium beyond bones/tissues and/or for any application beyond surgical procedures.

Example applications/procedures that may utilize any of the fasteners described or contemplated herein, in any configuration and with any of the features described herein, may include, but are not limited to: spine procedures (e.g., SI fusion, facet fixation, etc.), extremity procedures, reconstruction procedures, trauma procedures, sports related procedures, bone fixation procedures, bone fusion procedures, joint arthroplasty procedures, veterinary procedures, procedures involving osteoporotic or compromised bone, etc.

Moreover, fastener types that may utilize any of the thread designs, morphology, and/or features described herein may include, but are not limited to pedicle fasteners, cervical fasteners, threaded stems, threaded intramedullary canal stems, cortical fasteners, soft tissue fasteners, long fasteners, cannulated fasteners, joint stems, revision fasteners, compression fasteners (e.g., hip compression fasteners, etc.), veterinary fasteners, etc.

Figure 1B:
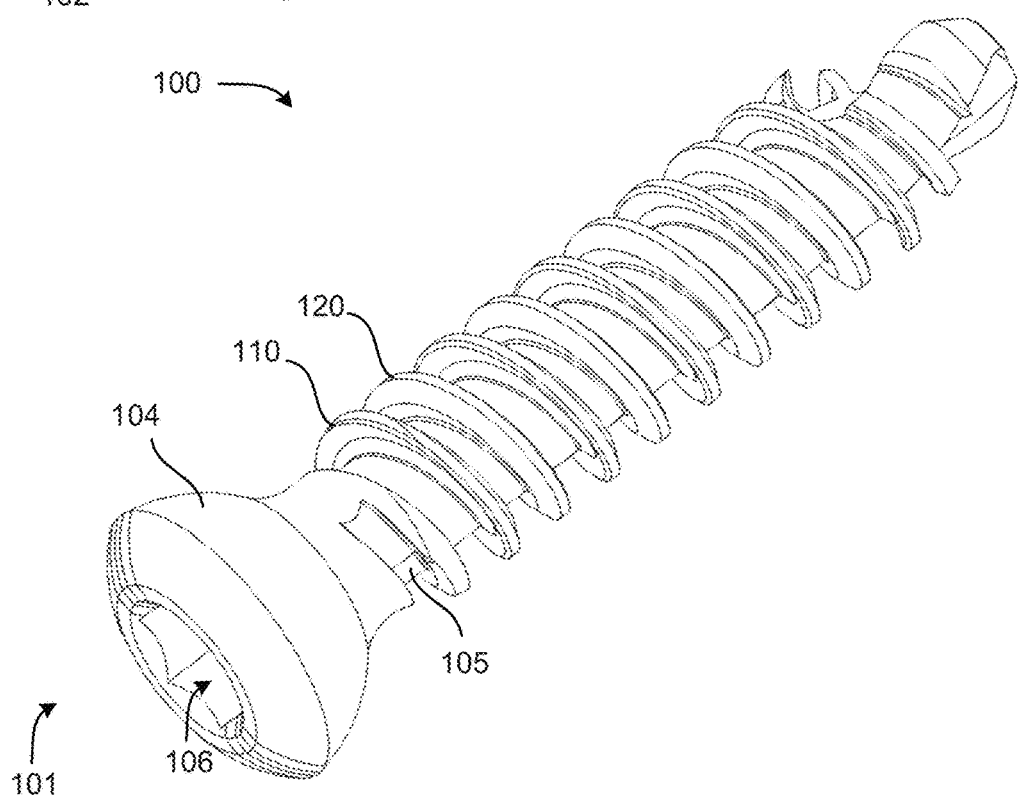
FIG. 1B illustrates a rear perspective view of the fastener of FIG. 1A.

FIGS. 1A-1D illustrate various views of a fastener 100, implantable bone anchor, or bone screw, according to one embodiment of the present disclosure. Specifically, FIG. 1A is a front perspective view of the fastener 100, FIG. 1B is a rear perspective view of the fastener 100, FIG. 1C is a side view of the fastener 100, and FIG. 1D is a cross-sectional side view of the fastener 100 taken along the line A-A in FIG. 1C.

In general, the fastener 100 may include a shaft 105 having a proximal end 101, a distal end 102, and a longitudinal axis 103. The fastener 100 may also include a head 104 located at the proximal end 101 of the shaft 105, a torque connection interface 106 formed in/on the head 104 (in either a male/female configuration), and a self-tapping feature 107 formed in the distal end 102 of the shaft 105.

In some embodiments, the fastener 100 may include a first helical thread 110 disposed about the shaft 105, and a second helical thread 120 disposed about the shaft 105 adjacent the first helical thread 110.

In some embodiments, the fastener 100 may include a "dual start" or "dual lead" thread configuration comprising the first helical thread 110 and the second helical thread 120.

In some embodiments, a depth of the first helical thread 110 and/or the second helical thread 120 with respect to the shaft 105 may define a major diameter vs. a minor diameter of the shaft 105 alone.

In some embodiments, a major diameter and/or a minor diameter of the fastener 100 may be constant or substantially constant along the entire length of the fastener, or along a majority of the length of the fastener. In these embodiments, a constant minor diameter may help avoid blowout of narrow/delicate bones (e.g., a pedicle) when inserting a fastener into a bone. In some embodiments, a pilot hole may first be drilled into a narrow/delicate bone and then a fastener having a similar minor diameter in comparison to the diameter of the pilot hole may be chosen to avoid blowout when inserting the fastener into the bone, as will be discussed in more detail below.

In some embodiments, a depth of the first helical thread 110 and/or the second helical thread 120 with respect to the shaft 105 may vary along a length of the shaft 105 to define one or more major diameters of the fastener 100 and/or one or more regions along the fastener 100 may comprise a one or more continuously variable major diameters.

In some embodiments, a thickness of the shaft 105 may vary along a length of the shaft 105 to define one or more minor diameters of the fastener 100, and/or one or more regions along the fastener 100 may comprise one or more continuously variable minor diameters. In some embodiments, a thickness/height/width/length/pitch/shape, etc., of the first helical thread 110 and/or the second helical thread 120 (or any additional helical thread) may vary along a length of the shaft 105. For example, a thickness/height/width/length/pitch/shape, etc., of the first helical thread 110 and/or the second helical thread 120 may be greater towards the tip of the fastener and thinner towards the head of the fastener (or vice versa) in either a discrete or continuously variable fashion, etc.

In some embodiments, the major and/or minor diameters may increase toward a proximal end or head of a fastener in order to increase bone compaction as the fastener is terminally inserted into the bone/tissue.

In some embodiments, a pitch of the first helical thread 110 and/or the second helical thread 120 may vary along a length of the fastener 100.

In some embodiments, the fastener 100 may include a plurality of helical threads disposed about the shaft 105.

However, it will also be understood that any of the fasteners disclosed or contemplated herein may include a single helical thread disposed about the shaft of the fastener. Moreover, the fastener 100 may comprise a nested plurality of helical threads having different lengths (not shown). As one non-limiting example, the fastener 100 may include a first helical thread 110 that is longer than a second helical thread 120, such that the fastener 100 comprises dual threading along a first portion of the shaft 105 and single threading along a second portion of the shaft 105.

In some embodiments, the plurality of helical threads may include three helical threads (not shown) comprising a "triple start" or "triple lead" thread configuration (not shown).

In some embodiments, the plurality of helical threads may include four helical threads (not shown) comprising a "quadruple start" or "quadruple lead" thread configuration (not shown).

In some embodiments, the plurality of helical threads may include more than four helical threads (not shown).

In some embodiments, the fastener 100 may include first threading with any of the shapes disclosed herein oriented toward one of the proximal end and the distal end of the fastener 100, with the first threading located proximate the distal end of the fastener 100, as well as second threading with any of the shapes disclosed herein oriented toward the other one of the proximal end and the distal end of the fastener 100, with the second threading located proximate the head of the fastener 100 (not shown).

In some embodiments, the fastener 100 may include multiple threading (e.g., dual helical threading, etc.) with any of the shapes disclosed herein located proximate one of the proximal end and the distal end of the fastener 100, as well as single threading with any of the shapes disclosed herein with the second threading located proximate the other of the proximal end and the distal end of the fastener 100 (not shown).

In some embodiments, the first helical thread 110 may include a plurality of first concave undercut surfaces 131 and a plurality of first convex undercut surfaces 141.

In some embodiments, the second helical thread 120 may include a plurality of second concave undercut surfaces 132 and a plurality of second convex undercut surfaces 142.

In some embodiments, when the fastener 100 is viewed in section along a plane that intersects the longitudinal axis 103 of the shaft 105 (see FIG. 1D), the plurality of first concave undercut surfaces 131 and the plurality of second convex undercut surfaces 142 may be oriented toward (i.e., point toward) the proximal end 101 of the shaft 105.

In some embodiments, the plurality of first convex undercut surfaces 141 and the plurality of second concave undercut surfaces 132 may be oriented toward (i.e., point toward) the distal end 102 of the shaft 105.

In some embodiments, at least one of the plurality of first concave undercut surfaces 131, the plurality of first convex undercut surfaces 141, the plurality of second concave undercut surfaces 132, and the plurality of second convex undercut surfaces 142 may comprise at least one substantially flat surface.

In some embodiments, when the fastener 100 is viewed in section along a plane intersecting the longitudinal axis 103 of the shaft 105, the first helical thread 110 may comprise a plurality of first bent shapes (comprising at least one surface that is angled relative to the longitudinal axis 103 of the shaft 105 and/or at least one undercut surface) with a plurality of first intermediate portions 151 that are oriented toward (i.e., point toward) the distal end 102 of the shaft 105. This may be referred to as "standard" threading, having a "standard" orientation.

In some embodiments, when the fastener 100 is viewed in section along a plane intersecting the longitudinal axis 103 of the shaft 105, the second helical thread 120 may comprise a plurality of second bent shapes (comprising at least one surface that is angled relative to the longitudinal axis 103 of the shaft 105 and/or at least one undercut surface) with a plurality of second intermediate portions 152 that are oriented toward (i.e., point toward) the proximal end 101 of the shaft 105. This may be referred to as "inverted" threading, having an "inverted" orientation.

In some embodiments, one or more helical threads may morph/transition between a standard orientation and an inverted orientation along a shaft of a fastener.

In some embodiments, at least one of the plurality of first concave undercut surfaces 131, the plurality of first convex undercut surfaces 141, the plurality of second concave undercut surfaces 132, and the plurality of second convex undercut surfaces 142 may comprise at least one curved surface.

As shown in FIG. 1D, the proximally-oriented and distally-oriented surfaces of the first helical thread 110 (i.e., the first concave undercut surfaces 131 and the first convex undercut surfaces 141 in the fastener 100 of FIG. 1D) may not have mirror symmetry relative to each other about any plane perpendicular to the longitudinal axis 103 of the fastener 100. Rather, the first concave undercut surfaces 131 and the first convex undercut surfaces 141 may be generally parallel to each other. The same may be true for the second helical thread 120, in which the second concave undercut surfaces 132 and the second convex undercut surfaces 142 may not have mirror symmetry relative to each other but may be generally parallel to each other.

Conversely, as also shown in FIG. 1D, the proximally-oriented surfaces of the first helical thread 110 may have mirror symmetry relative to the distally-oriented surfaces of the second helical thread 120. Specifically, the first concave undercut surfaces 131 may have mirror symmetry relative to the second convex undercut surfaces 142 about a plane 170 that bisects the space between them and lies perpendicular to the longitudinal axis 103.

Similarly, the distally-oriented surfaces of the first helical thread 110 may have mirror symmetry relative to the proximally-oriented surfaces of the second helical thread 120. Specifically, the second concave undercut surfaces 132 may have mirror symmetry relative to the first convex undercut surfaces 141 about a plane 172 that bisects the space between them and lies perpendicular to the longitudinal axis 103.

This mirror symmetry may be present along most of the length of the first helical thread 110 and the second helical thread 120, with symmetry across different planes arranged between adjacent turns of the first helical thread 110 and the second helical thread 120 along the length of the longitudinal axis 103. Such mirror symmetry may help more effectively capture bone between the first helical thread 110 and the second helical thread 120 and may also facilitate manufacture of the fastener 100.

Figure 3:
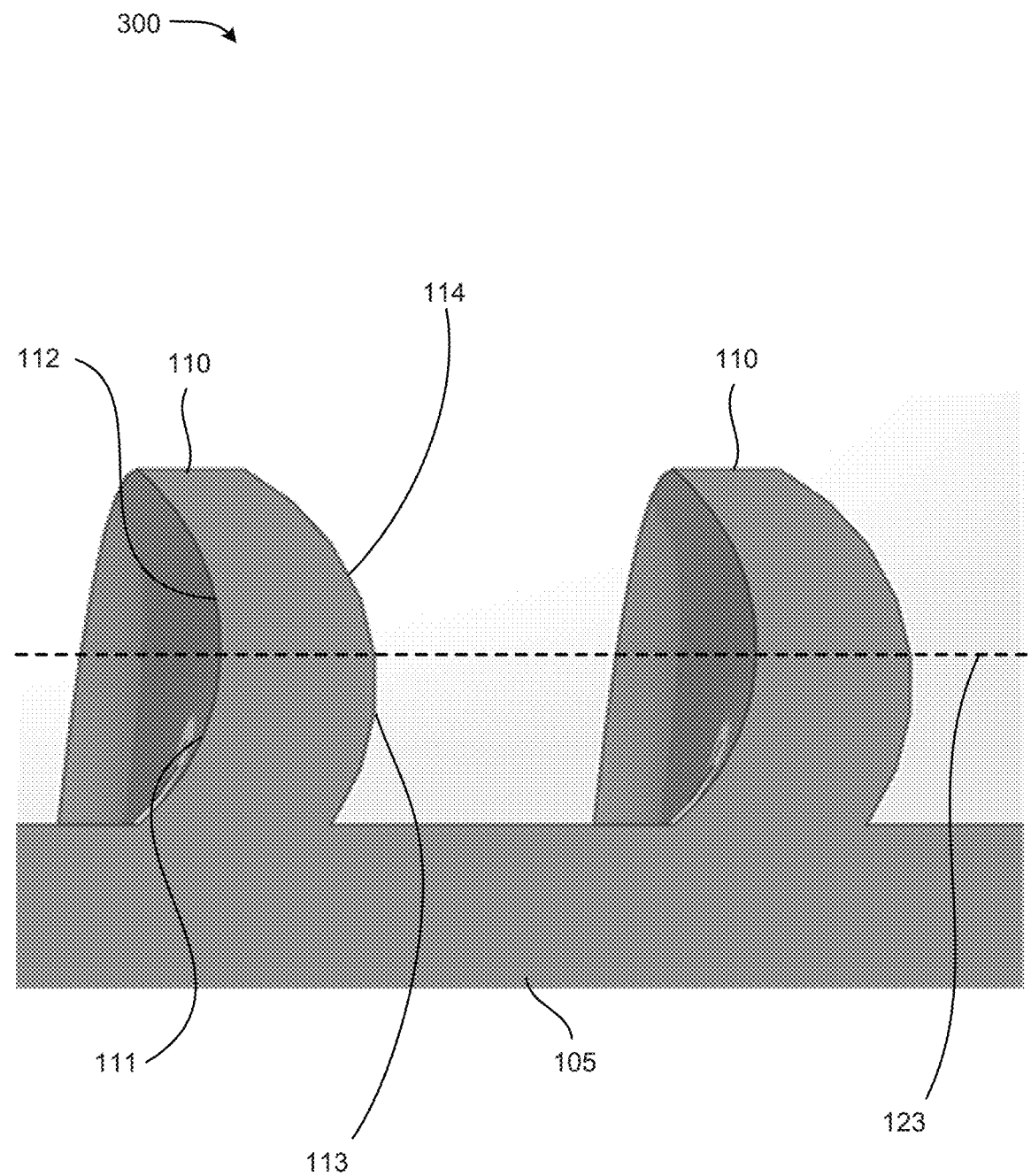
FIG. 3 illustrates a partial cross-sectional side view of a fastener comprising crescent-shaped threading.

In some embodiments, when the fastener 100 is viewed in section along a plane intersecting the longitudinal axis 103 of the shaft 105, the first helical thread 110 may include at least one partial crescent shape that is oriented toward (i.e., points toward) the distal end 102 of the shaft 105 and/or the proximal end 101 of the shaft 105. FIG. 3 illustrates a partial cross-sectional view of a fastener 300 comprising crescent shapes, as one non-limiting example of such an embodiment.

In some embodiments (not shown), when the fastener 100 is viewed in section along a plane intersecting the longitudinal axis 103 of the shaft 105, the first helical thread 110 may include at least one partial crescent shape that is oriented toward (i.e., points toward) the distal end 102 of the shaft 105, and the second helical thread 120 may include at least one partial crescent shape that is oriented toward (i.e., points toward) the proximal end 101 of the shaft 105.

In some embodiments (not shown), the first helical thread 110 may include a first plurality of partial crescent shapes that are oriented toward (i.e., point toward) the distal end 102 of the shaft 105, and the second helical thread 120 may include a second plurality of partial crescent shapes that are oriented toward (i.e., point toward) the proximal end 101 of the shaft 105.

In some embodiments (not shown), the first plurality of partial crescent shapes and the second plurality of partial crescent shapes may be arranged in alternating succession along the shaft 105 of the fastener 100.

In some embodiments, the first helical thread 110 may be bisected by the line 123 shown in FIG. 3 with each crescent shape including a plurality of first undercut surfaces 111, a plurality of second undercut surfaces 112, a plurality of third undercut surfaces 113, and a plurality of fourth open surfaces 114 similar to the helical threading shown in FIG. 1D, except with curved surfaces in place of flat surfaces.

In some embodiments, the plurality of first undercut surfaces 111 and the plurality of second undercut surfaces 112 may comprise concave curved surfaces. However, it will be understood that portions of the plurality of first undercut surfaces 111 and/or portions of the plurality of second undercut surfaces 112 may also comprise convex curved surfaces and/or flat surfaces (not shown in FIG. 3).

In some embodiments, the plurality of third undercut surfaces 113 and the plurality of fourth open surfaces 114 may comprise convex curved surfaces. However, it will be understood that portions of the plurality of third undercut surfaces 113 and the plurality of fourth open surfaces 114 may also comprise concave curved surfaces and/or flat surfaces (not shown in FIG. 3).

In some embodiments, the plurality of third undercut surfaces 113 and the plurality of fourth open surfaces 114 may be replaced by a ramped surface (such as that utilized in a standard buttress thread design) without any undercuts (not shown in FIG. 3). Likewise, any of the other thread designs disclosed herein may utilize a ramped or buttress thread design on at least one side of the helical thread.

In some embodiments, a fastener may have only standard threads or only inverted threads. The type of threads that are desired may depend on the type and/or magnitude of loads to be applied to the fastener. For example, a screw loaded axially away from the bone in which it is implanted may advantageously have a standard thread, while a screw loaded axially toward the bone in which it is implanted may advantageously have an inverted thread. A screw that may experience multi-axial loading and/or off-loading conditions may advantageously include at least one standard thread and at least one inverted thread in order to increase bone fixation and load sharing between a bone/fastener interface during multi-axial and off-loading conditions to reduce high bone strain and distribute multi-axial forces applied to the bone in a load-sharing, rather than load-bearing, configuration. Shear loads and/or bending moments may also be optimally resisted with any chosen combination of threading, threading morphology, and/or threading variations contemplated herein to optimally resist shear loads, bending moments, multi-axial loading, off-loading conditions, etc.

In some embodiments, fasteners with standard threads may be used in conjunction with fasteners with inverted threads in order to accommodate different loading patterns.

In some embodiments, a single fastener may have both standard and inverted threads, like the fastener 100. Such a combination of threads may help the fastener 100 remain in place with unknown and/or varying loading patterns.

In some embodiments, the geometry of the threading of a fastener (with standard and/or inverted threads) may be varied to suit the fastener for a particular loading scheme. For example, the number of threads, the number of thread starts, the pitch of the threading, the lead(s) of the threading, the shape(s) of the threading, any dimension(s) associated with the threading (e.g., any length(s)/width(s)/height(s), etc., associated with the threading), the major diameter(s), the minor diameter(s), any angulation/angles associated with any surfaces of the threading, the "handedness" of the threading (e.g., right-handed vs. left-handed), etc., may be varied accordingly to suit any specific medium of installation, loading pattern, desired radial loading force, pull-out strength, application, procedure, etc., that may be involved.

In some embodiments, the material(s) of any portion of a fastener described herein may include, but are not limited to metals (e.g., titanium, cobalt, stainless steel, etc.), metal alloys, plastics, polymers, PEEK, UHMWPE, composites, additive particles, textured surfaces, biologics, biomaterials, bone, etc.

In some embodiments, any of the fasteners described herein may include additional features such as: self-tapping features, locking features (e.g., locking threading formed on a portion of the fastener, such as threading located on or near a head of the fastener), cannulation, any style of fastener head (or no fastener head at all), any style of torque connection interface (or no torque connection interface at all), etc.

In some embodiments, a tap (not shown) may be utilized to pre-form threading in a bone according to any threading shape that is disclosed or contemplated herein. In this manner, taps with any suitable shape may be utilized in conjunction with any fastener described or contemplated herein to match or substantially match the threading geometry of a given fastener.

In some embodiments, a minor diameter of the fastener may be selected to match, or substantially match, a diameter of a pilot hole that is formed in a bone to avoid bone blowout when the fastener is inserted into the pilot hole, as will be discussed in more detail below.

Additionally, or alternatively thereto, the type of threads and/or thread geometry may be varied based on the type of bone in which the fastener is to be anchored. For example, fasteners anchored in osteoporotic bone may fare better with standard or inverted threads, or when the pitch, major diameter, and/or minor diameter are increased or decreased, or when the angulation of thread surfaces is adjusted, etc.

In some embodiments, a surgical kit may include multiple fasteners with any of the different fasteners and thread options described or contemplated herein. The surgeon may select the appropriate fastener(s) from the kit based on the particular loads to be applied and/or the quality of bone in which the fastener(s) are to be anchored.

Continuing with FIG. 1D, in some embodiments the first helical thread 110 may include a plurality of first undercut surfaces 111, a plurality of second undercut surfaces 112, a plurality of third undercut surfaces 113, and a plurality of fourth open surfaces 114.

In some embodiments, the second helical thread 120 may include a plurality of fifth undercut surfaces 125, a plurality of sixth undercut surfaces 126, a plurality of seventh undercut surfaces 127, and a plurality of eighth open surfaces 128.

In some embodiments one or more of the plurality of first undercut surfaces 111, the plurality of second undercut surfaces 112, the plurality of third undercut surfaces 113, the plurality of fourth open surfaces 114, the plurality of fifth undercut surfaces 125, the plurality of sixth undercut surfaces 126, the plurality of seventh undercut surfaces 127, and the plurality of eighth open surfaces 128 may comprise at least one flat or substantially flat surface.

In some embodiments, the plurality of first undercut surfaces 111, the plurality of third undercut surfaces 113, the plurality of sixth undercut surfaces 126, and the plurality of eighth open surfaces 128 may be angled towards the distal end 102 of the shaft 105.

In some embodiments, the plurality of second undercut surfaces 112, the plurality of fourth open surfaces 114, the plurality of fifth undercut surfaces 125, and the plurality of seventh undercut surfaces 127 may be angled towards the proximal end 101 of the shaft 105.

In some embodiments, when the fastener 100 is viewed in section along a plane that intersects the longitudinal axis 103 of the shaft 105 (as shown in FIG. 1D), the first helical thread 110 may include at least one chevron shape that is oriented toward (i.e., points toward) the distal end 102 of the shaft 105. Likewise, the second helical thread 120 may also include at least one chevron shape that is oriented toward (i.e., points toward) the proximal end 101 of the shaft 105.

In some embodiments, when the fastener 100 is viewed in section along a plane that intersects the longitudinal axis 103 of the shaft 105 (as shown in FIG. 1D), the first helical thread 110 may include a first plurality of chevron shapes that are oriented toward (i.e., point toward) the distal end 102 of the shaft 105. Likewise, the second helical thread 120 may include a second plurality of chevron shapes that are oriented toward (i.e., point toward) the proximal end 101 of the shaft 105.

In some embodiments, the first plurality of chevron shapes and the second plurality of chevron shapes may be arranged in alternating succession along the shaft 105 of the fastener 100, (e.g., see FIG. 1D).

In some embodiments, a plurality of first interlocking spaces 161 and a plurality of second interlocking spaces 162 may be formed between the first helical thread 110 and the second helical thread 120 along the shaft 105 of the fastener 100.

In some embodiments, the plurality of first interlocking spaces 161 may be formed intermediate the first concave undercut surfaces 131 and the second concave undercut surfaces 132.

In some embodiments, the plurality of second interlocking spaces 162 may be formed intermediate the first convex undercut surfaces 141 and the second convex undercut surfaces 142.

In some embodiments, the plurality of first interlocking spaces 161 may be larger in size than the plurality of second interlocking spaces.

In some embodiments, the plurality of first interlocking spaces 161 and the plurality of second interlocking spaces 162 may be shaped and/or configured to interlock with bone/other tissues received therein to increase fixation of the fastener 100 within the bone/other tissues and provide additional resistance against multi-axial forces that may be applied to the fastener 100 and/or the bone/other tissues.

In some embodiments, the plurality of second undercut surfaces 112 and the plurality of sixth undercut surfaces 126 may be angled toward each other to trap bone/other tissues within the plurality of first interlocking spaces 161 in order to increase fixation and resistance against multi-axial forces.

In some embodiments, the plurality of third undercut surfaces 113 and the plurality of seventh undercut surfaces 127 may be angled toward each other to trap bone/other tissues within the plurality of second interlocking spaces 162 in order to increase fixation and resistance against multi-axial forces.

In some embodiments, the plurality of first undercut surfaces 111 and the plurality of fifth undercut surfaces 125 may each form an angle α with respect to the longitudinal axis 103 of the shaft 105, as shown in FIG. 1D.

In some embodiments, the angle α may be greater than 90 degrees.

In some embodiments, the plurality of second undercut surfaces 112 and the plurality of sixth undercut surfaces 126 may each form an angle β with respect to the longitudinal axis 103 of the shaft 105.

In some embodiments, the angle β may be less than 90 degrees.

In some embodiments, the plurality of third undercut surfaces 113 and the plurality of seventh undercut surfaces 127 may each form an angle θ with respect to the longitudinal axis 103 of the shaft 105.

In some embodiments, the angle θ may be approximately 90 degrees.

In some embodiments, the angle θ may be greater than 90 degrees.

It will be understood that the fastener 100 may include any thread configuration, feature, or morphology described or contemplated herein to achieve optimal fixation within a given bone/tissue. Moreover, it will also be understood that the fastener 100 may be utilized in conjunction with (or within) any system, method, or instrumentation described or contemplated herein.

Figure 2A:
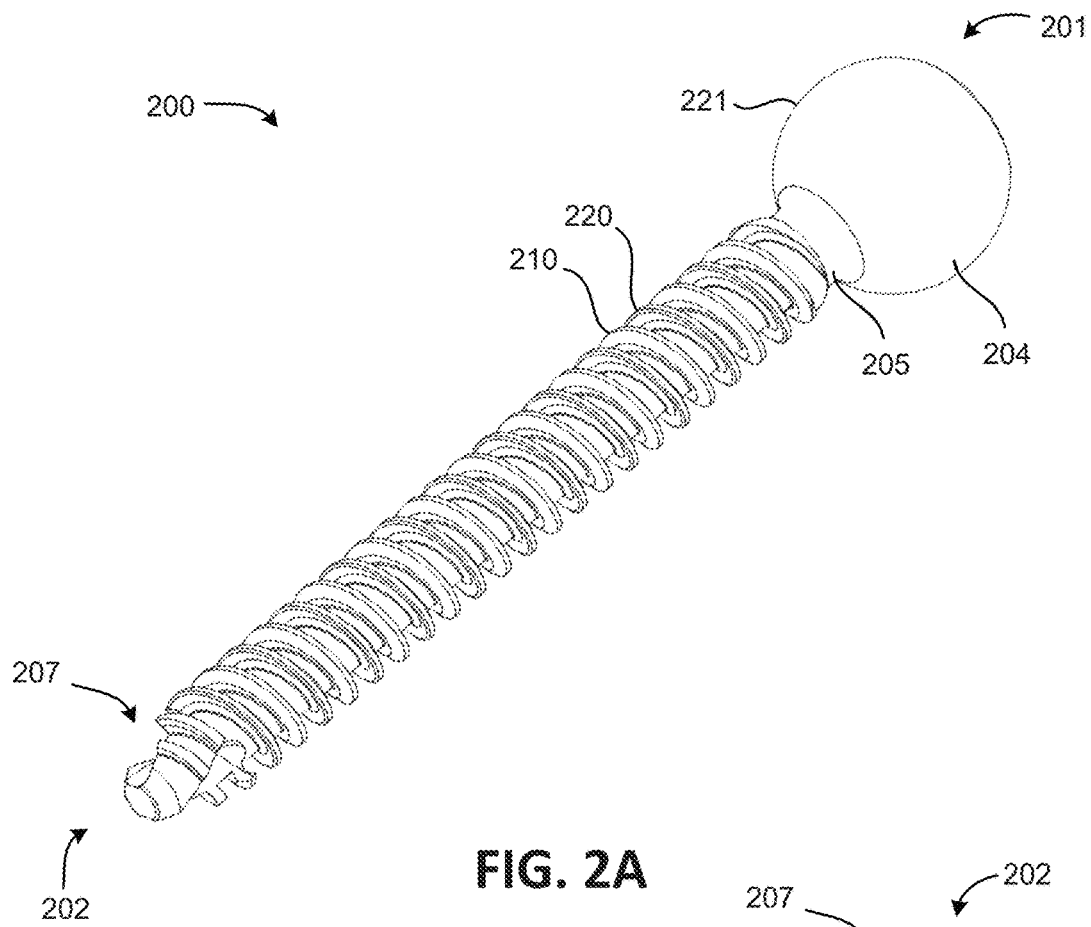
FIG. 2A illustrates a front perspective view of a fastener, according to another embodiment of the present disclosure.
Figure 2B:
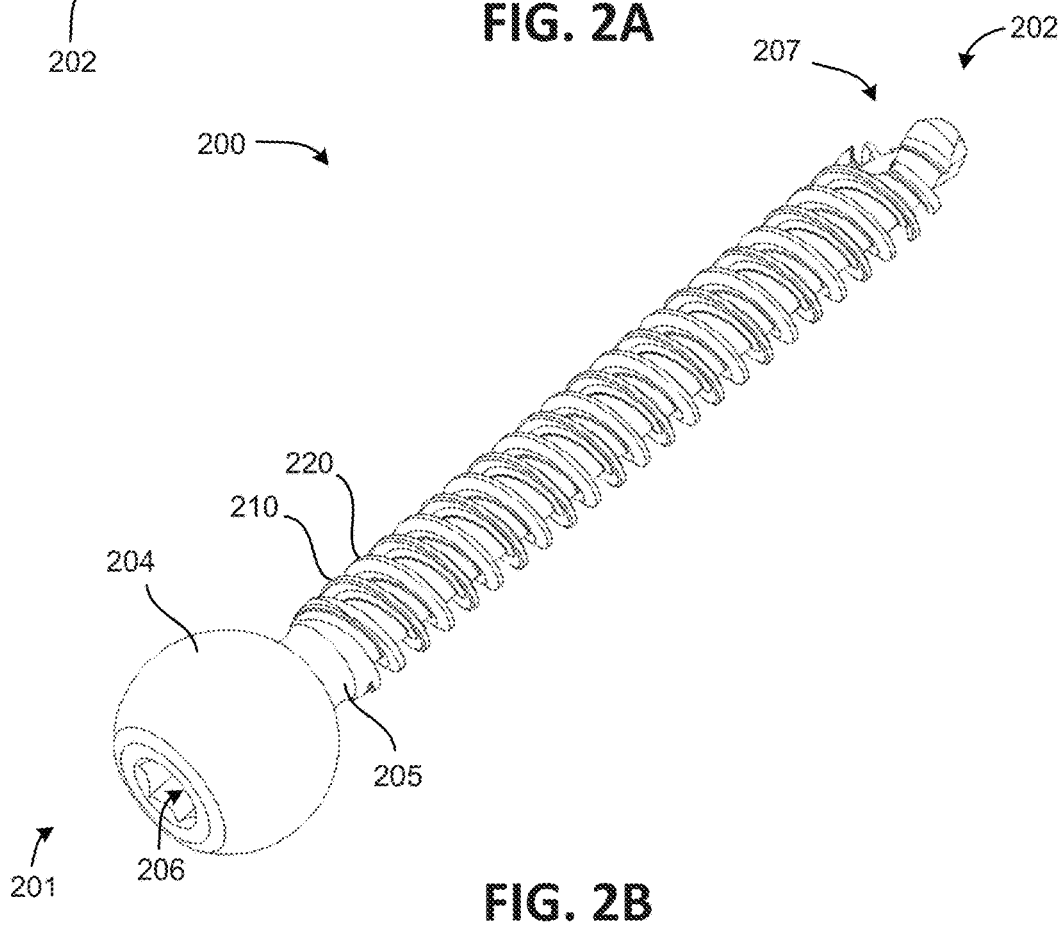
FIG. 2B illustrates a rear perspective view of the fastener of FIG. 2A.
Figure 2C:
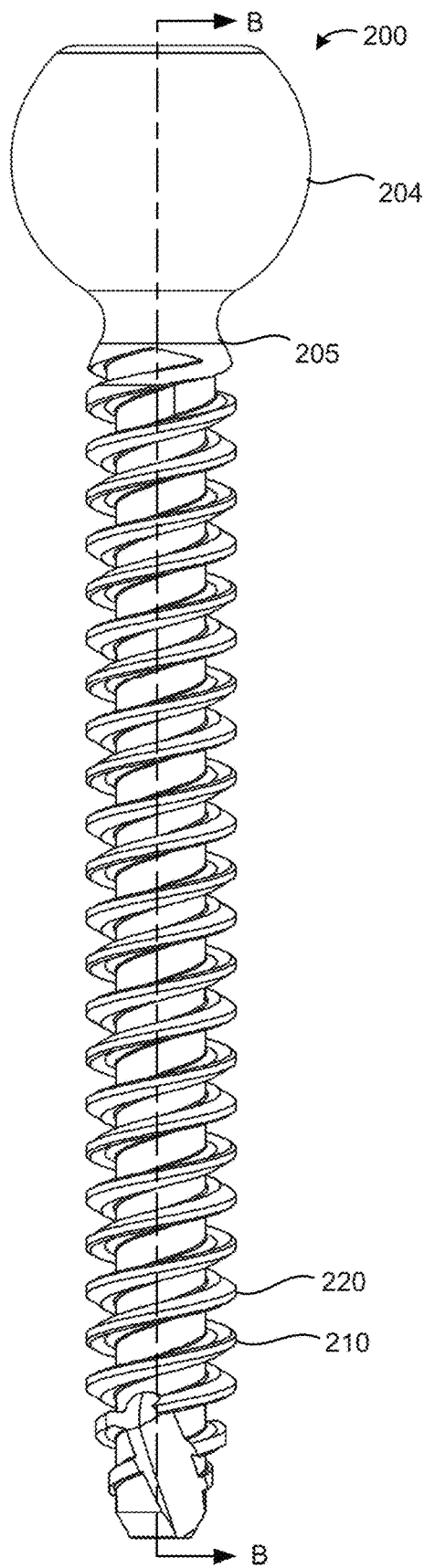
FIG. 2C illustrates a side view of the fastener of FIG. 2A.
Figure 2D:
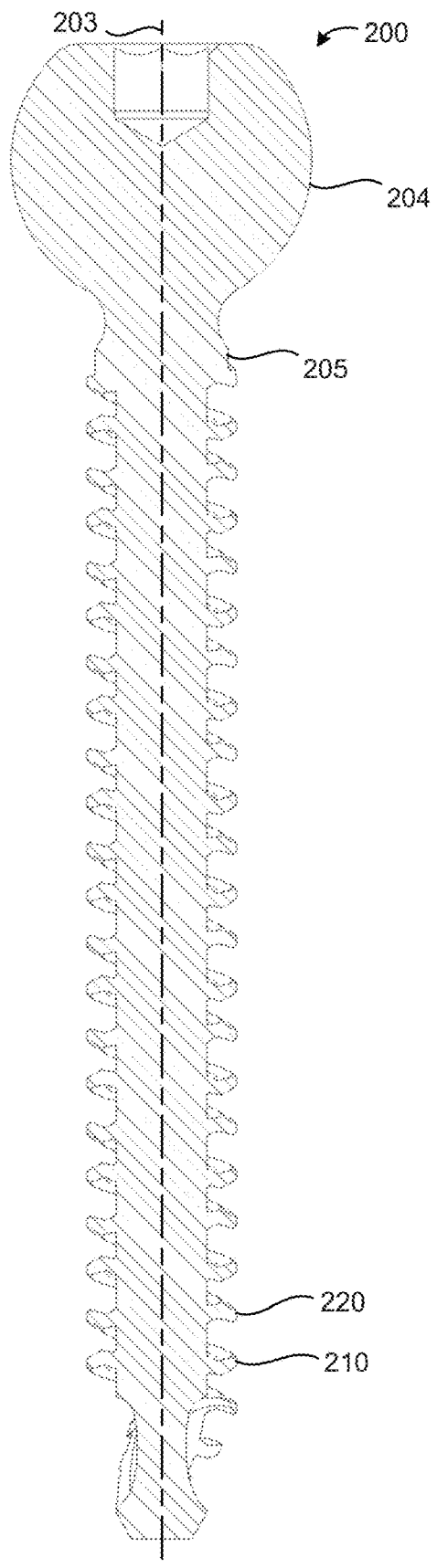
FIG. 2D illustrates a cross-sectional side view of the fastener of FIG. 2A taken along the line B-B shown in FIG. 2C.

FIGS. 2A-2D illustrate various views of a polyaxial screw, pedicle bone fastener, or fastener 200, according to another embodiment of the present disclosure. Specifically, FIG. 2A is a front perspective view of the fastener 200, FIG. 2B is a rear perspective view of the fastener 200, FIG. 2C is a side view of the fastener 200, and FIG. 2D is a cross-sectional side view of the fastener 200 taken along the line B-B in FIG. 2C. The fastener 200 may include a shaft 205 having a proximal end 201, a distal end 202, and a longitudinal axis 203. The fastener 200 may also include a polyaxial head 204 having a first semi-spherical surface 221 located at the proximal end 201 of the shaft 205, a torque connection interface 206 formed in/on the polyaxial head 204, and a self-tapping feature 207 formed in the distal end 202 of the shaft 205. In some embodiments, the fastener 200 may include a first helical thread 210 disposed about the shaft 205, and a second helical thread 220 disposed about the shaft 205 adjacent the first helical thread 210. In these embodiments, the fastener 200 may comprise a "dual start" or "dual lead" thread configuration. However, it will also be understood that the fastener 200 may include any thread configuration, feature, or morphology described or contemplated herein to achieve optimal fixation within a given bone/tissue. Moreover, it will also be understood that the fastener 200 may be utilized in conjunction with (or within) any system, method, or instrumentation described or contemplated herein.

Figure 4A:
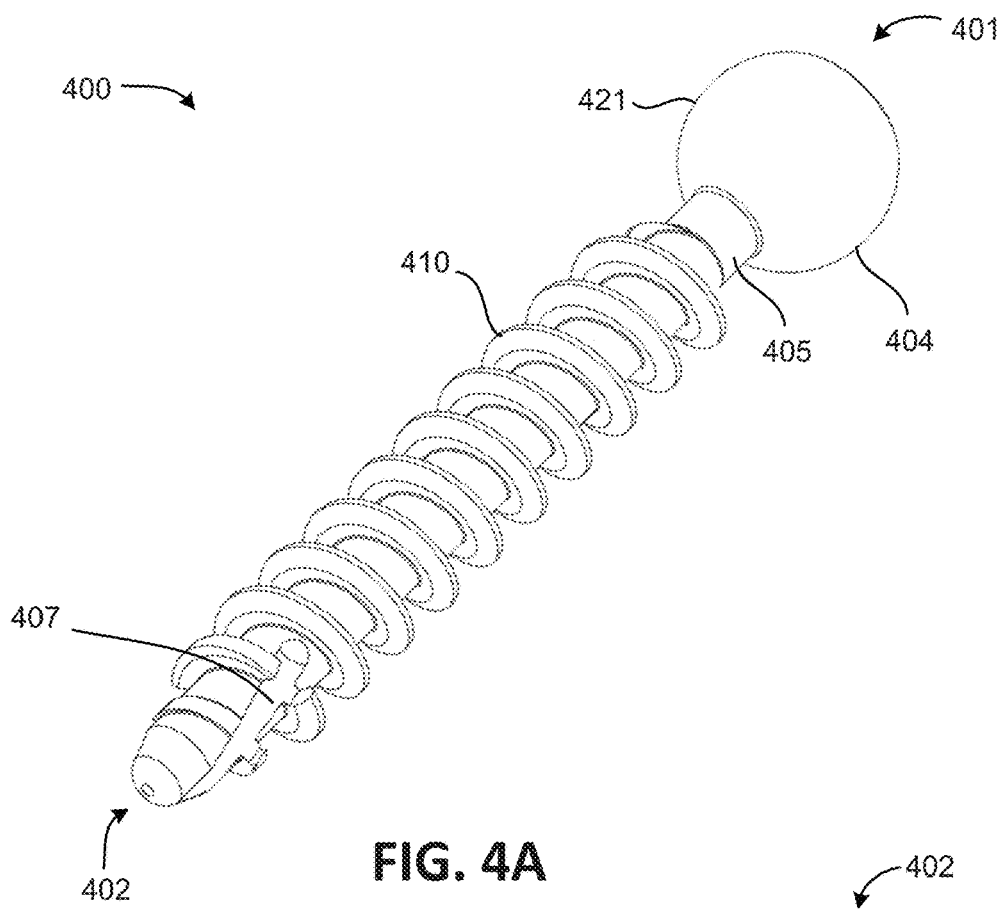
FIG. 4A illustrates a front perspective view of a fastener, according to another embodiment of the present disclosure.
Figure 4B:
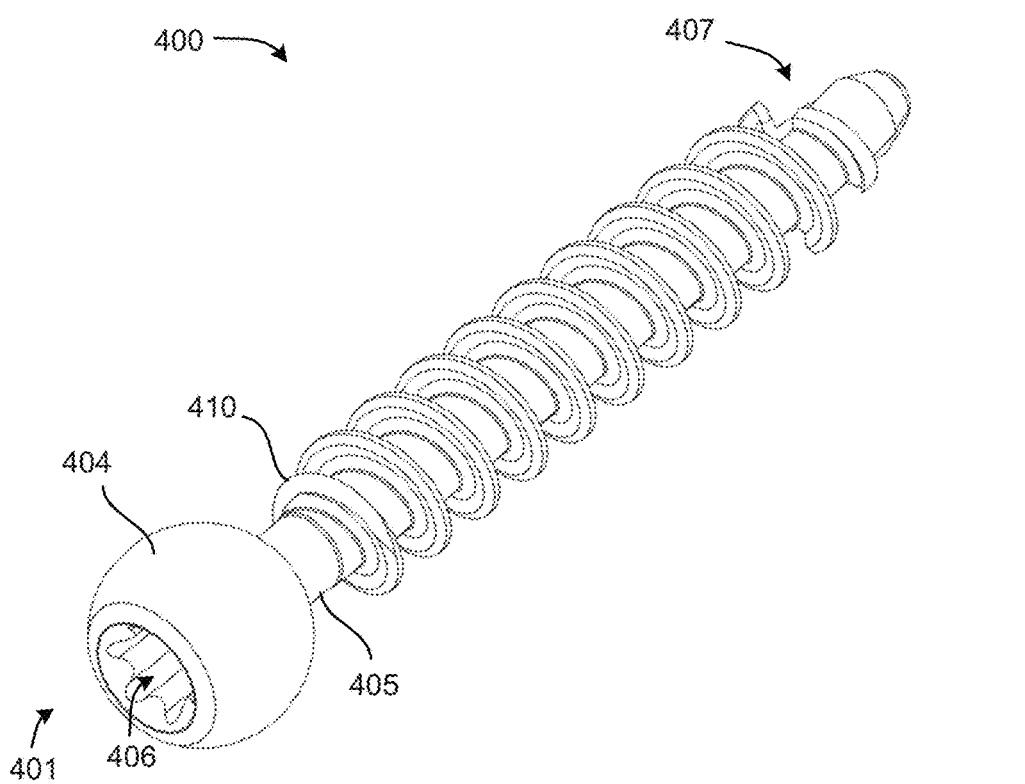
FIG. 4B illustrates a rear perspective view of the fastener of FIG. 4A.
Figure 4C:
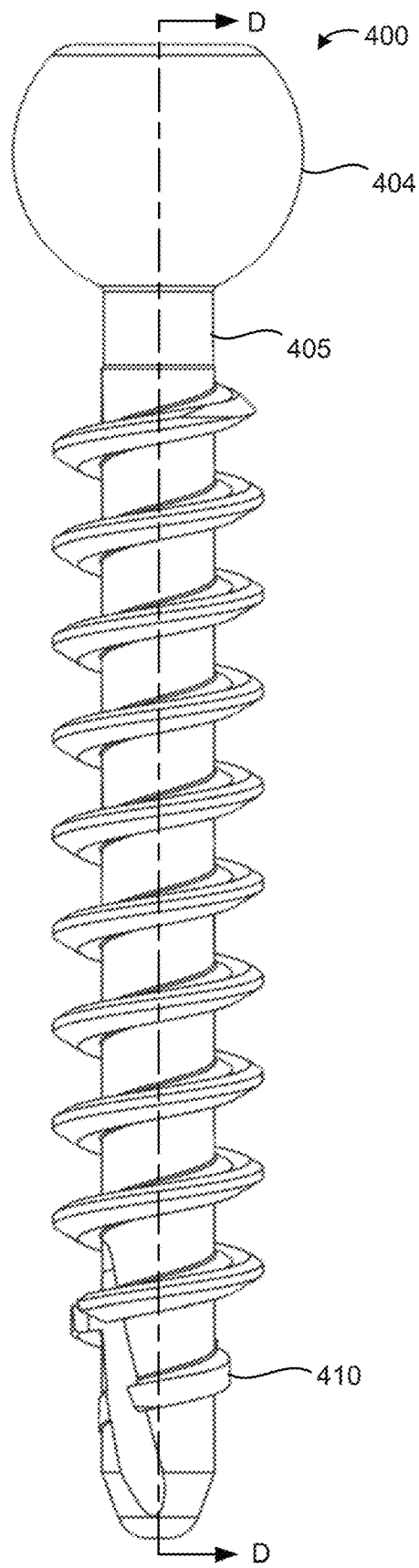
FIG. 4C illustrates a side view of the fastener of FIG. 4A.
Figure 4D:
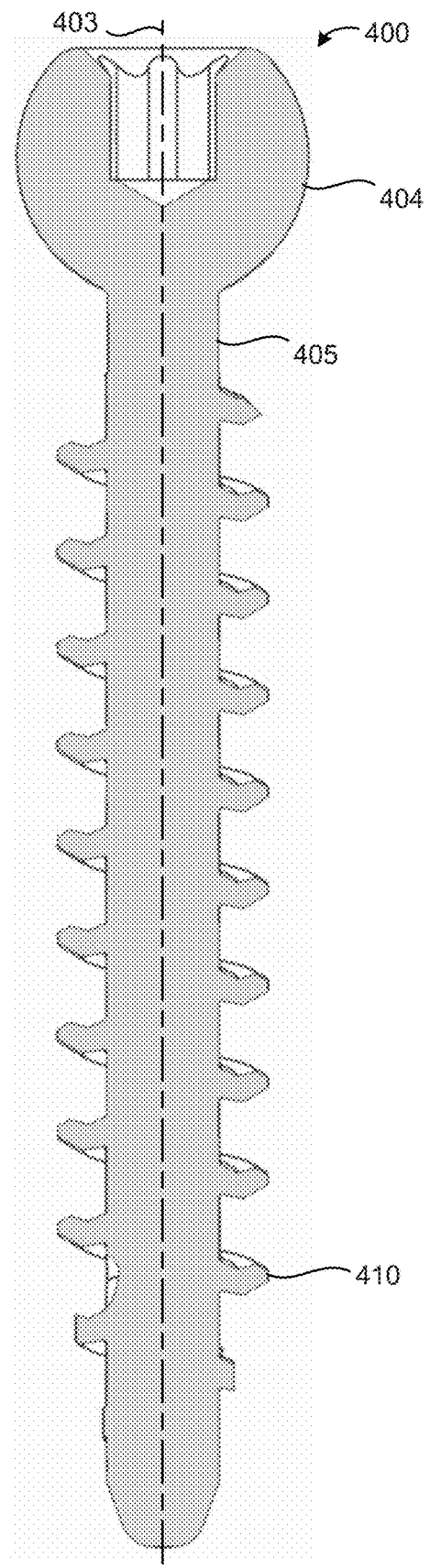
FIG. 4D illustrates a cross-sectional side view of the fastener of FIG. 4A taken along the line D-D shown in FIG. 4C.

FIGS. 4A-4D illustrate various views of a polyaxial screw, pedicle bone fastener, or fastener 400, according to another embodiment of the present disclosure. Specifically, FIG. 4A is a front perspective view of the fastener 400, FIG. 4B is a rear perspective view of the fastener 400, FIG. 4C is a side view of the fastener 400, and FIG. 4D is a cross-sectional side view of the fastener 400 taken along the line D-D in FIG. 4C. The fastener 400 may include a shaft 405 having a proximal end 401, a distal end 402, and a longitudinal axis 403. The fastener 400 may also include a polyaxial head 404 having a first semi-spherical surface 421 located at the proximal end 401 of the shaft 405, a torque connection interface 406 formed in/on the polyaxial head 404, and a self-tapping feature 407 formed in the distal end 402 of the shaft 405. In some embodiments, the fastener 400 may include a single helical thread 410 disposed about the shaft 405, as shown in FIG. 4D. In some embodiments, the fastener 400 may comprise a "single start" or "single lead" thread configuration having a standard orientation, as shown in FIG. 4D. However, it will also be understood that the fastener 400 may include any thread configuration, feature, or morphology described or contemplated herein to achieve optimal fixation within a given bone/tissue. Moreover, it will also be understood that the fastener 400 may be utilized in conjunction with (or within) any system, method, or instrumentation described or contemplated herein.

Figure 5A:
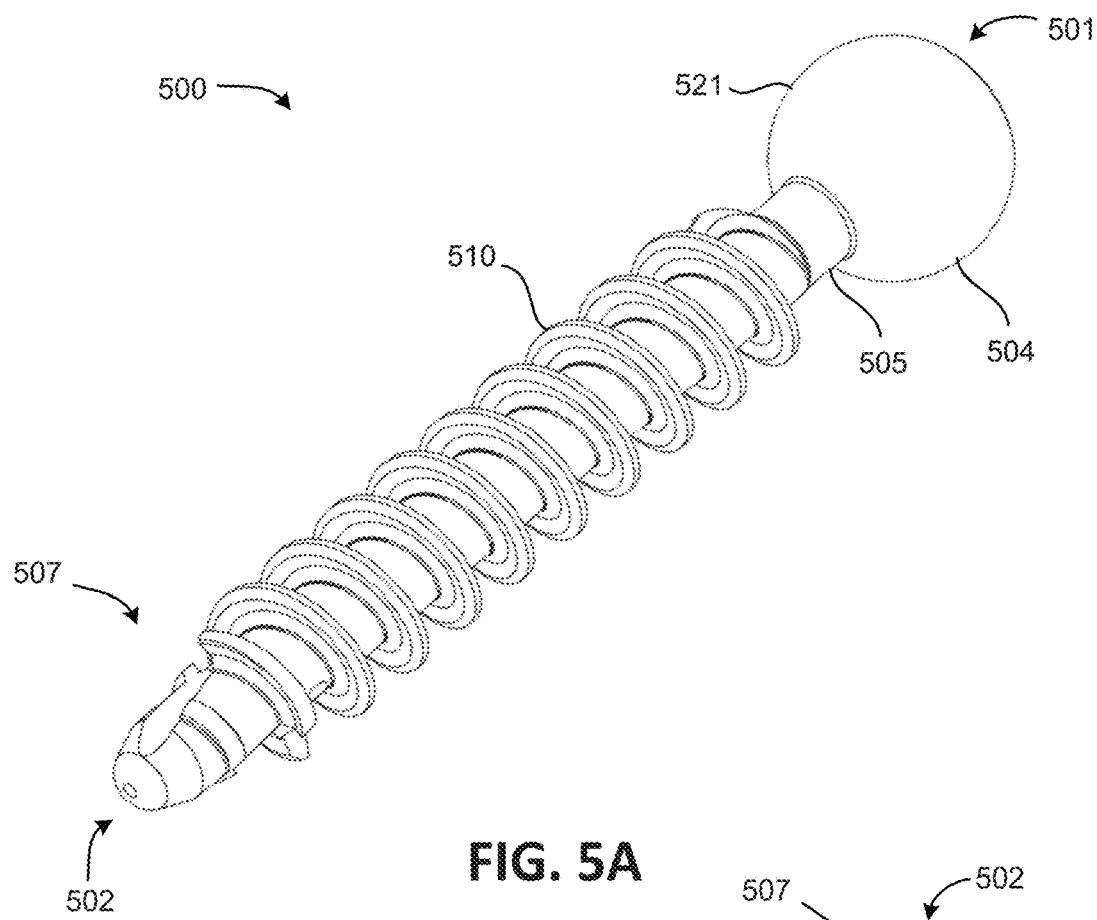
FIG. 5A illustrates a front perspective view of a fastener, according to another embodiment of the present disclosure.
Figure 5B:
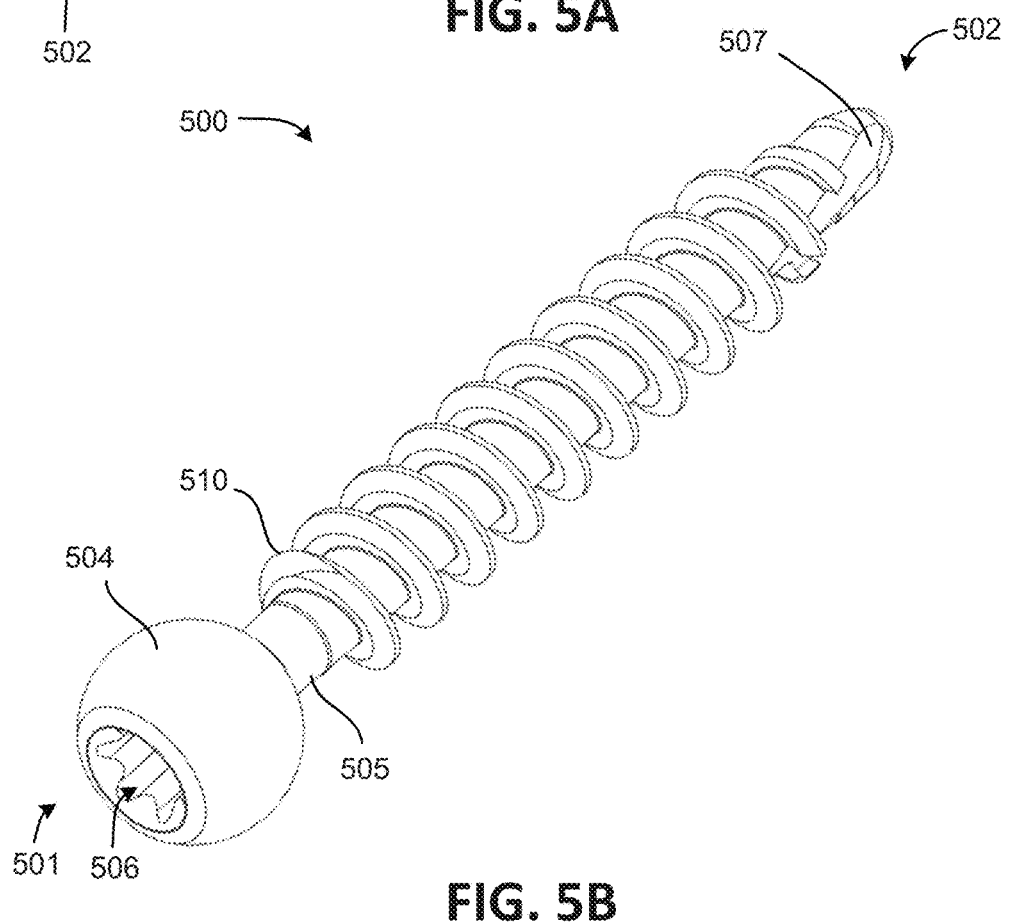
FIG. 5B illustrates a rear perspective view of the fastener of FIG. 5A.
Figure 5C:
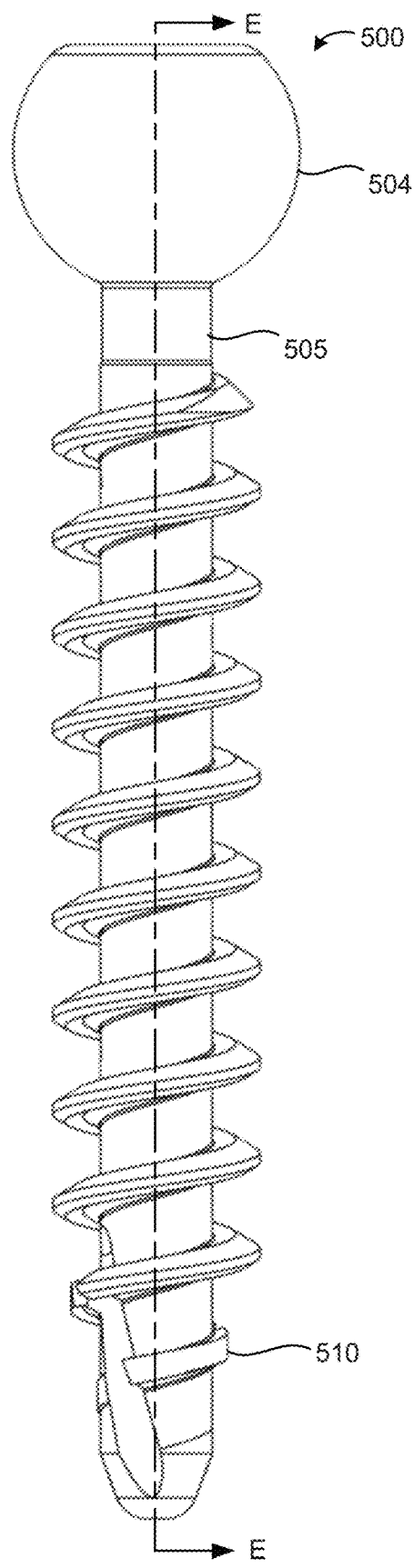
FIG. 5C illustrates a side view of the fastener of FIG. 5A.
Figure 5D:
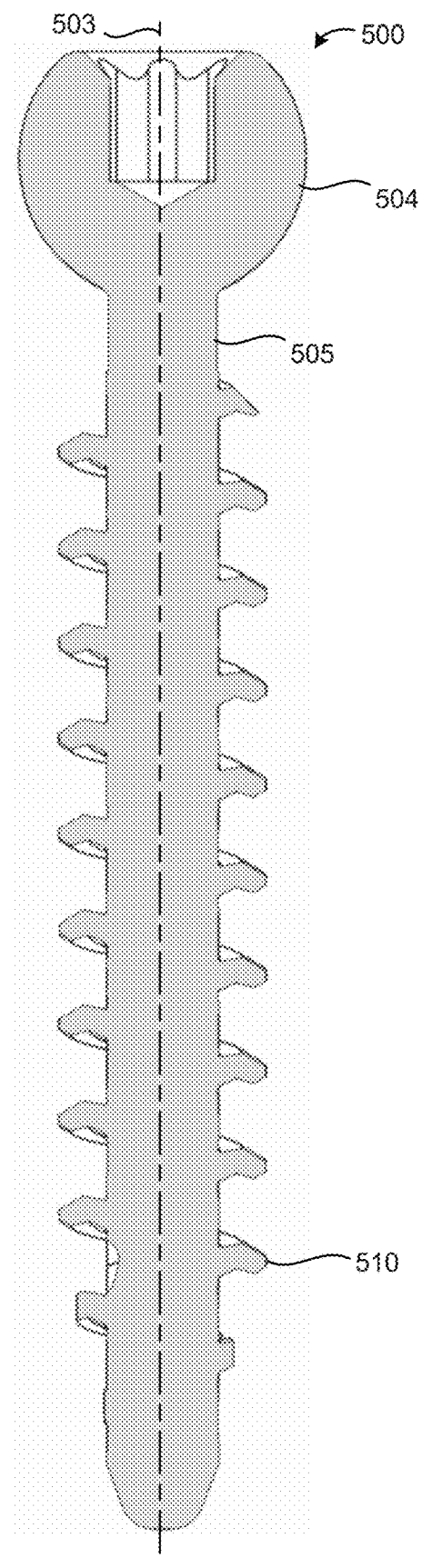
FIG. 5D illustrates a cross-sectional side view of the fastener of FIG. 5A taken along the line E-E shown in FIG. 5C.

FIGS. 5A-5D illustrate various views of a polyaxial screw, pedicle bone fastener, or fastener 500, according to another embodiment of the present disclosure. Specifically, FIG. 5A is a front perspective view of the fastener 500, FIG. 5B is a rear perspective view of the fastener 500, FIG. 5C is a side view of the fastener 500, and FIG. 5D is a cross-sectional side view of the fastener 500 taken along the line E-E in FIG. 5C. The fastener 500 may include a shaft 505 having a proximal end 501, a distal end 502, and a longitudinal axis 503. The fastener 500 may also include a polyaxial head 504 having a first semi-spherical surface 521 located at the proximal end 501 of the shaft 505, a torque connection interface 506 formed in/on the polyaxial head 504, and a self-tapping feature 507 formed in the distal end 502 of the shaft 505. In some embodiments, the fastener 500 may include a single helical thread 510 disposed about the shaft 505, as shown in FIG. 5D. In some embodiments, the fastener 500 may comprise a "single start" or "single lead" thread configuration having an inverted orientation, as shown in FIG. 5D. However, it will also be understood that the fastener 500 may include any thread configuration, feature, or morphology described or contemplated herein to achieve optimal fixation within a given bone/tissue. Moreover, it will also be understood that the fastener 500 may be utilized in conjunction with (or within) any system, method, or instrumentation described or contemplated herein.

Figure 6A:
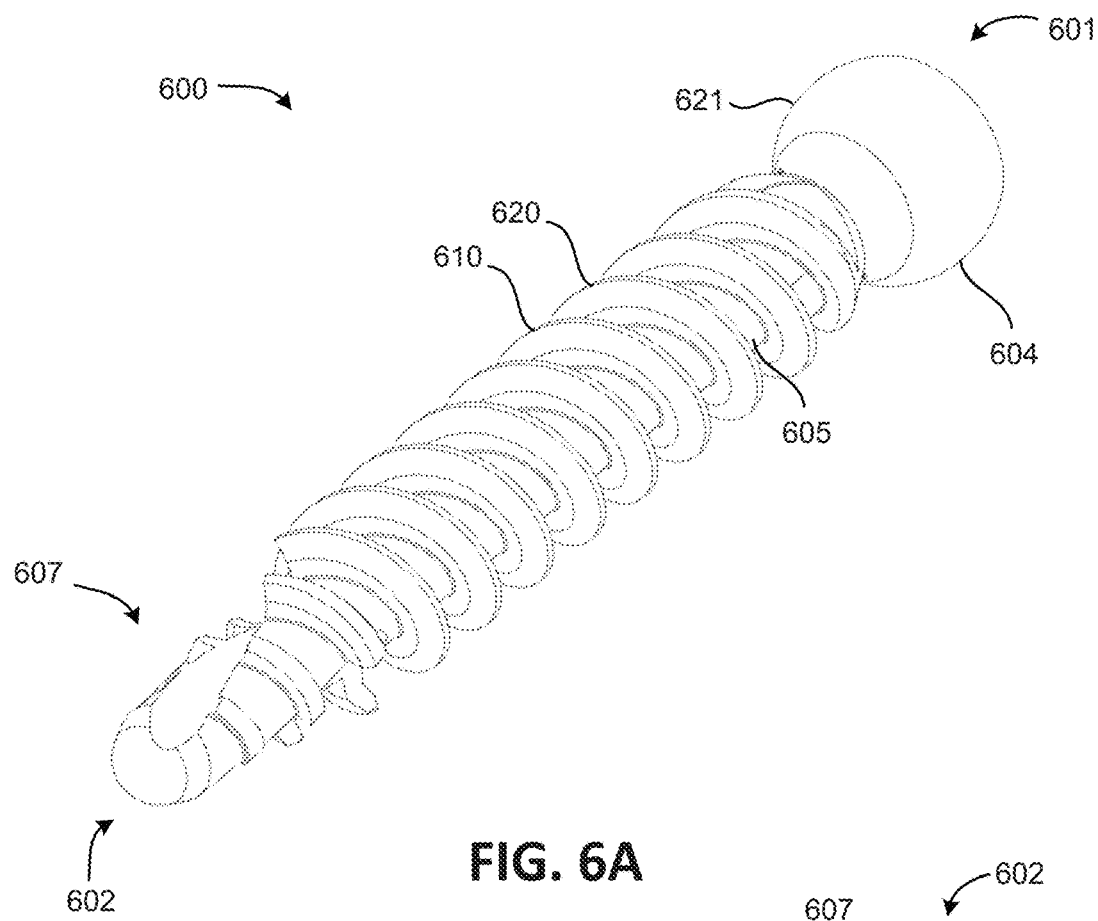
FIG. 6A illustrates a front perspective view of a fastener, according to another embodiment of the present disclosure.
Figure 6B:
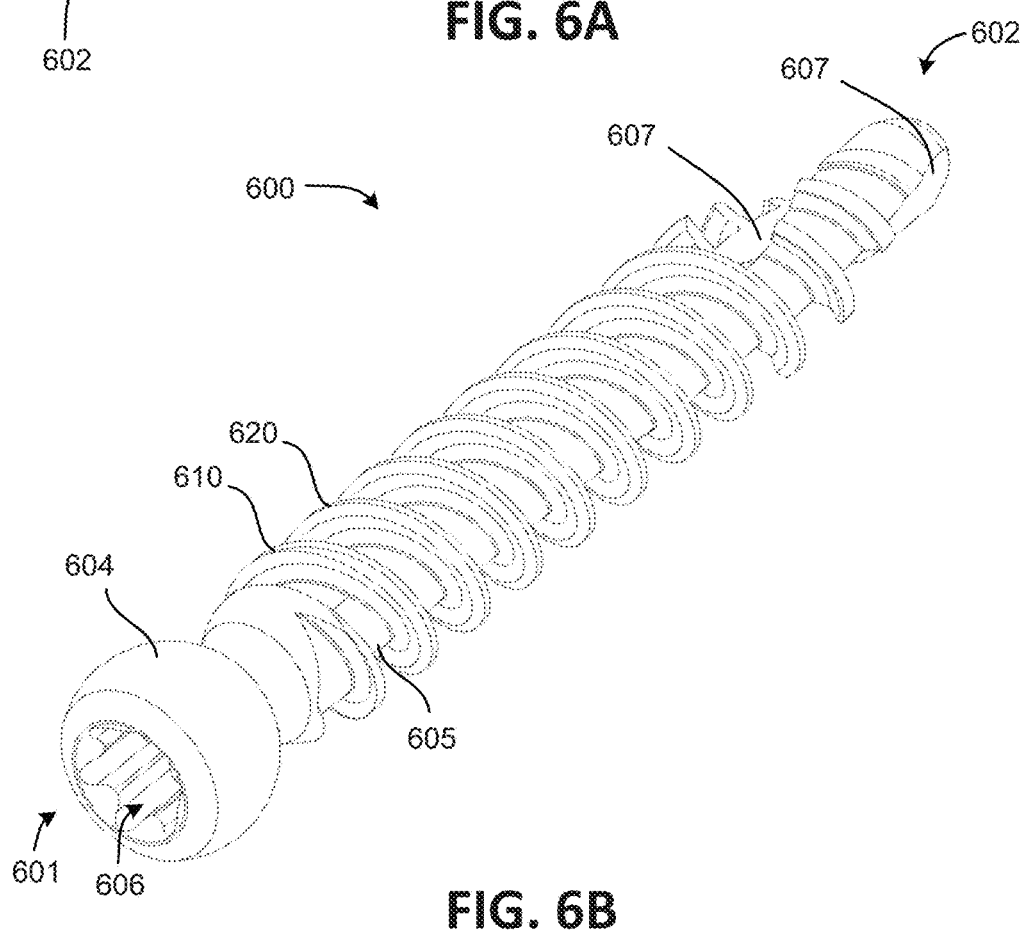
FIG. 6B illustrates a rear perspective view of the fastener of FIG. 6A.
Figure 6C:
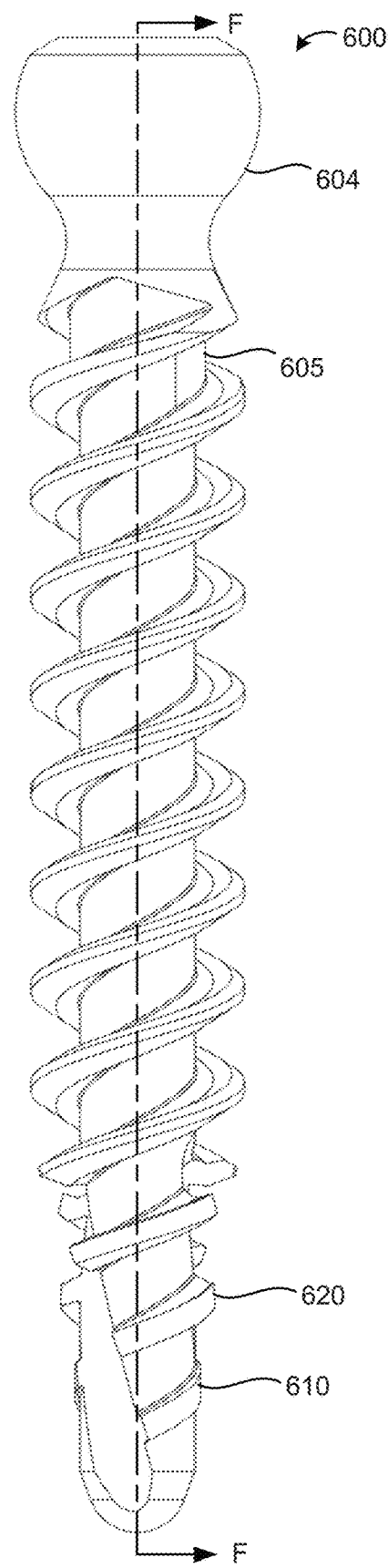
FIG. 6C illustrates a side view of the fastener of FIG. 6A.
Figure 6D:
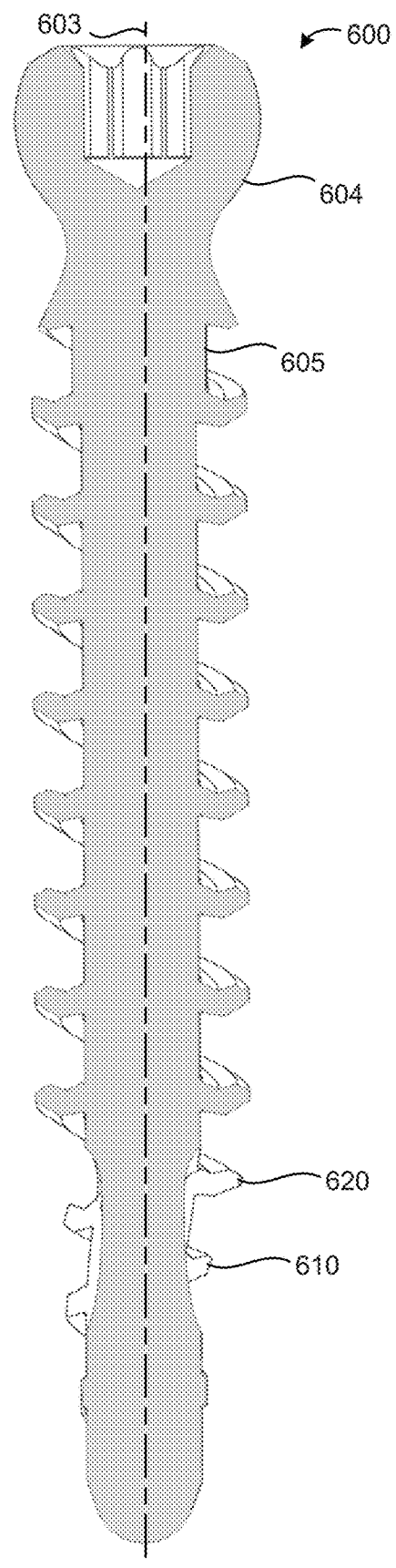
FIG. 6D illustrates a cross-sectional side view of the fastener of FIG. 6A taken along the line F-F shown in FIG. 6C.

FIGS. 6A-6D illustrate various views of a polyaxial screw, pedicle bone fastener, or fastener 600, according to another embodiment of the present disclosure. Specifically, FIG. 6A is a front perspective view of the fastener 600, FIG. 6B is a rear perspective view of the fastener 600, FIG. 6C is a side view of the fastener 600, and FIG. 6D is a cross-sectional side view of the fastener 600 taken along the line F-F in FIG. 6C. The fastener 600 may include a shaft 605 having a proximal end 601, a distal end 602, and a longitudinal axis 603. The fastener 600 may also include a polyaxial head 604 having a first semi-spherical surface 621 located at the proximal end 601 of the shaft 605, a torque connection interface 606 formed in/on the polyaxial head 604, and a self-tapping feature 607 formed in the distal end 602 of the shaft 605. In some embodiments, the fastener 600 may include a first helical thread 610 disposed about the shaft 605, and a second helical thread 620 disposed about the shaft 605 adjacent the first helical thread 610. In these embodiments, the fastener 600 may comprise a "dual start" or "dual lead" thread configuration. In some embodiments, a dual start thread configuration may allow quicker insertion of the fastener 600 into bone/other tissues by requiring fewer rotations of the fastener 600 during insertion. In some embodiments, the first helical thread 610 and the second helical thread 620 may each comprise "standard" threading having a "standard" orientation, as shown in FIG. 6D. However, it will also be understood that the fastener 600 may include any thread configuration, feature, or morphology described or contemplated herein to achieve optimal fixation within a given bone/tissue. Moreover, it will also be understood that the fastener 600 may be utilized in conjunction with (or within) any system, method, or instrumentation described or contemplated herein.

Figure 7A:
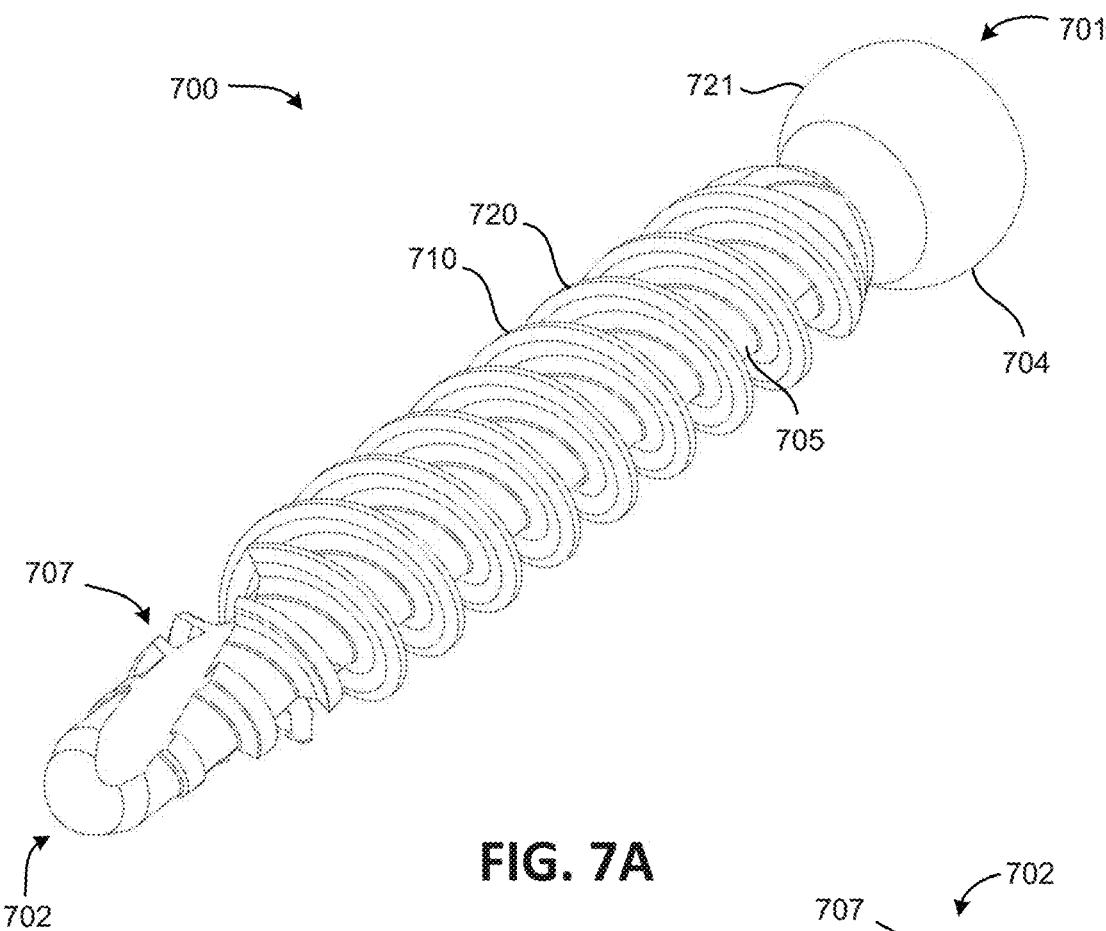
FIG. 7A illustrates a front perspective view of a fastener, according to another embodiment of the present disclosure.
Figure 7B:
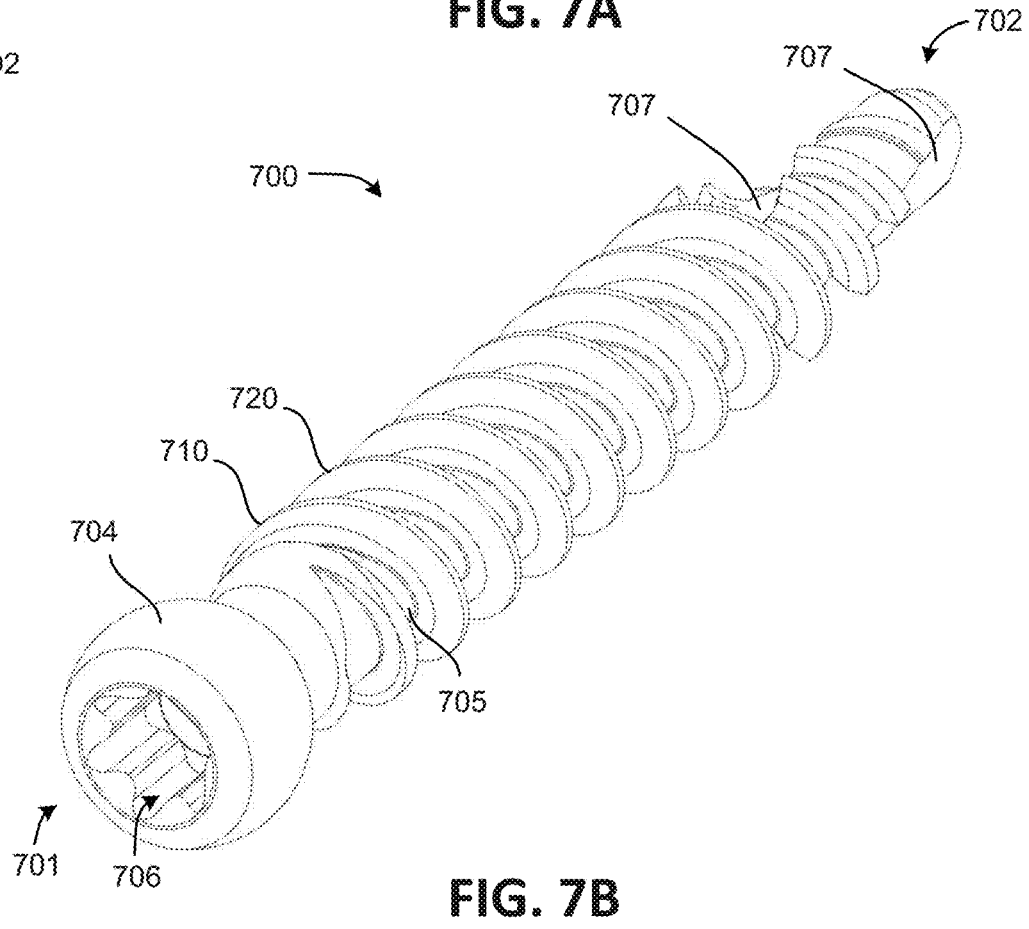
FIG. 7B illustrates a rear perspective view of the fastener of FIG. 7A.
Figure 7C:
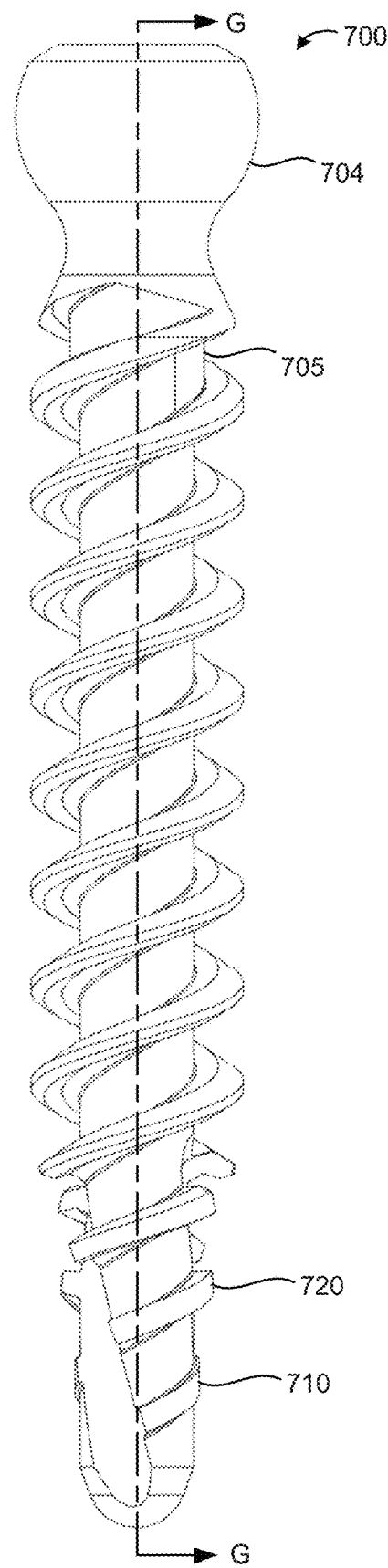
FIG. 7C illustrates a side view of the fastener of FIG. 7A.
Figure 7D:
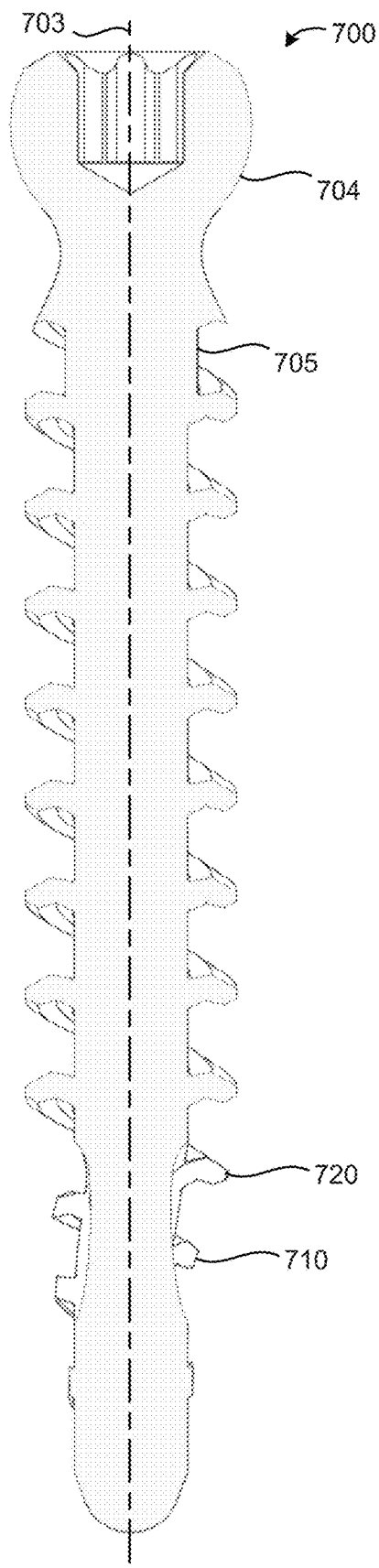
FIG. 7D illustrates a cross-sectional side view of the fastener of FIG. 7A taken along the line G-G shown in FIG. 7C.

FIGS. 7A-7D illustrate various views of a polyaxial screw, pedicle bone fastener, or fastener 700, according to another embodiment of the present disclosure. Specifically, FIG. 7A is a front perspective view of the fastener 700, FIG. 7B is a rear perspective view of the fastener 700, FIG. 7C is a side view of the fastener 700, and FIG. 7D is a cross-sectional side view of the fastener 700 taken along the line G-G in FIG. 7C. The fastener 700 may include a shaft 705 having a proximal end 701, a distal end 702, and a longitudinal axis 703. The fastener 700 may also include a polyaxial head 704 having a first semi-spherical surface 721 located at the proximal end 701 of the shaft 705, a torque connection interface 706 formed in/on the polyaxial head 704, and a self-tapping feature 707 formed in the distal end 702 of the shaft 705. In some embodiments, the fastener 700 may include a first helical thread 710 disposed about the shaft 705, and a second helical thread 720 disposed about the shaft 705 adjacent the first helical thread 710. In these embodiments, the fastener 700 may comprise a "dual start" or "dual lead" thread configuration. This dual start thread configuration may allow quicker insertion of the fastener 700 into bone/tissue by requiring fewer rotations of the fastener 700 during insertion. In some embodiments, the first helical thread 710 and the second helical thread 720 may each comprise "inverted" threading having an "inverted" orientation, as shown in FIG. 7D. However, it will be understood that the fastener 700 may include any thread configuration, feature, or morphology described or contemplated herein to achieve optimal fixation within a given bone/tissue. Moreover, it will also be understood that the fastener 700 may be utilized in conjunction with (or within) any system, method, or instrumentation described or contemplated herein.

Figure 8A:
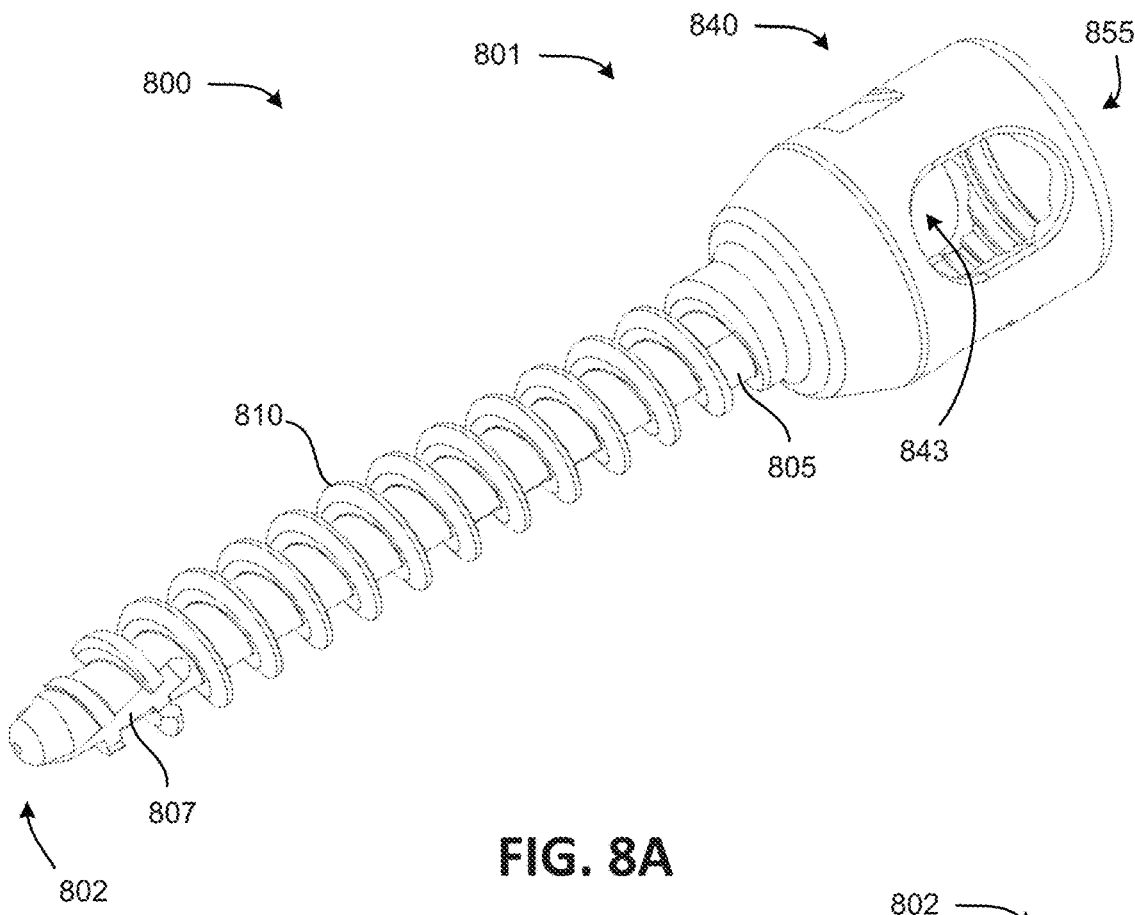
FIG. 8A illustrates a front perspective view of a fastener, according to another embodiment of the present disclosure.
Figure 8B:
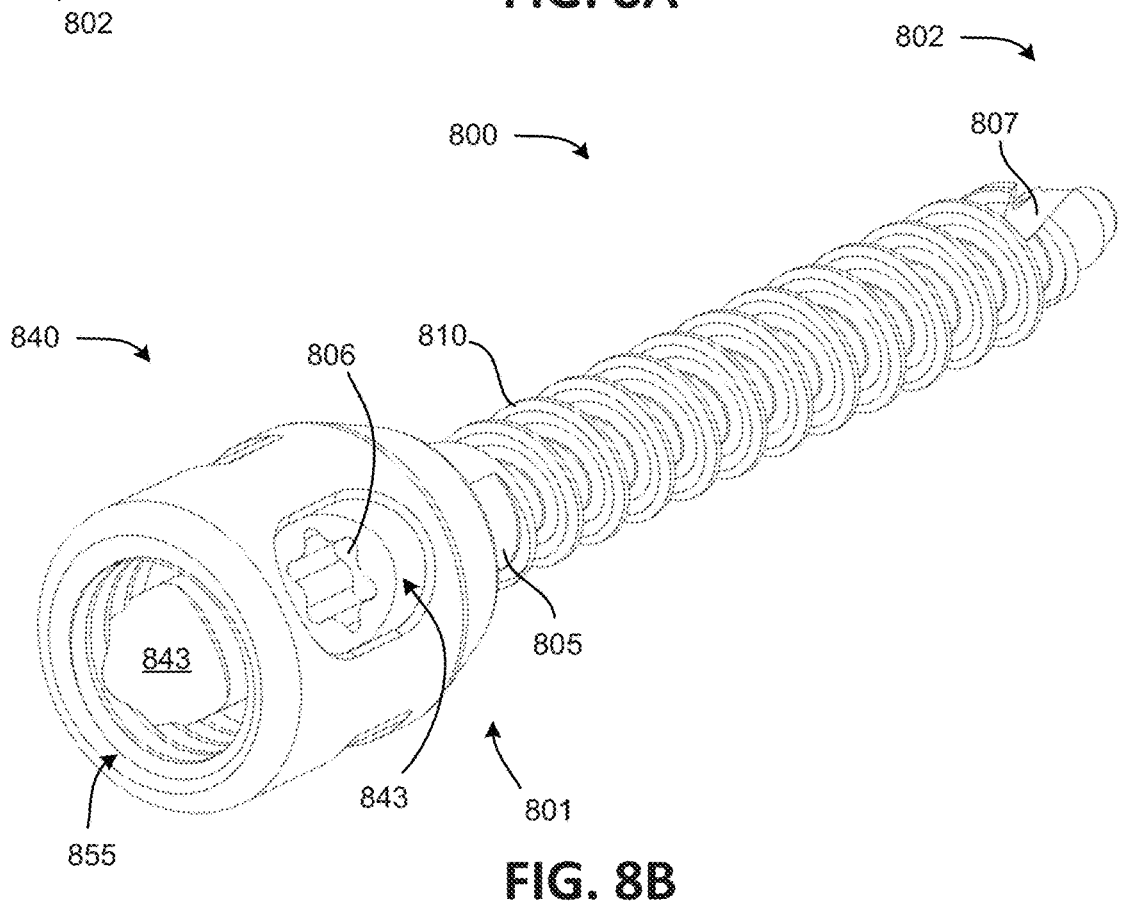
FIG. 8B illustrates a rear perspective view of the fastener of FIG. 8A.

FIGS. 8A and 8B illustrate various views of a pedicle bone fastener or fastener 800, according to another embodiment of the present disclosure. Specifically, FIG. 8A is a front perspective view of the fastener 800, and FIG. 8B is a rear perspective view of the fastener 800.

The fastener 800 may generally include a shaft 805 having a proximal end 801, a distal end 802, a helical thread 810, and self-tapping feature 807. The fastener 800 may also include an integrated attachment feature, such as an integrated tulip 840 located at the proximal end 801 of the shaft 805, and a torque connection interface 806 within the integrated tulip 840.

In some embodiments, at least a portion of a minor diameter of the shaft 805 and/or a major diameter of the helical thread 810 may be constant to help prevent bone blowout during insertion of the bone fastener, as will be discussed below in more detail.

The fastener 800 may also include a helical thread 810 disposed about the shaft 805. In some embodiments, the helical thread 810 may comprise standard threading. In some embodiments, the helical thread 810 may comprise inverted threading. However, it will be understood that the fastener 800 may include any thread configuration, feature, or morphology described or contemplated herein to achieve optimal fixation within a given bone/tissue. For example, in some embodiments the helical thread 810 may comprise a first helical thread with standard or inverted threading comprising a first concave undercut surface, and the fastener 800 may also include a second helical thread (not shown) with standard or inverted threading adjacent the first helical thread comprising a second concave undercut surface, forming a "dual start" thread configuration. Moreover, it will also be understood that the fastener 800 may be utilized in conjunction with (or within) any system, method, or instrumentation described or contemplated herein.

In some embodiments, the integrated tulip 840 may include at least one opening 843 formed through one or more sides of the integrated tulip 840.

In some embodiments, the integrated tulip 840 may include two openings formed through opposing sides of the integrated tulip 840.

In some embodiments, the at least one opening 843 may be configured to receive at least a part of a spinal stabilization implement therethrough.

Figure 9A:
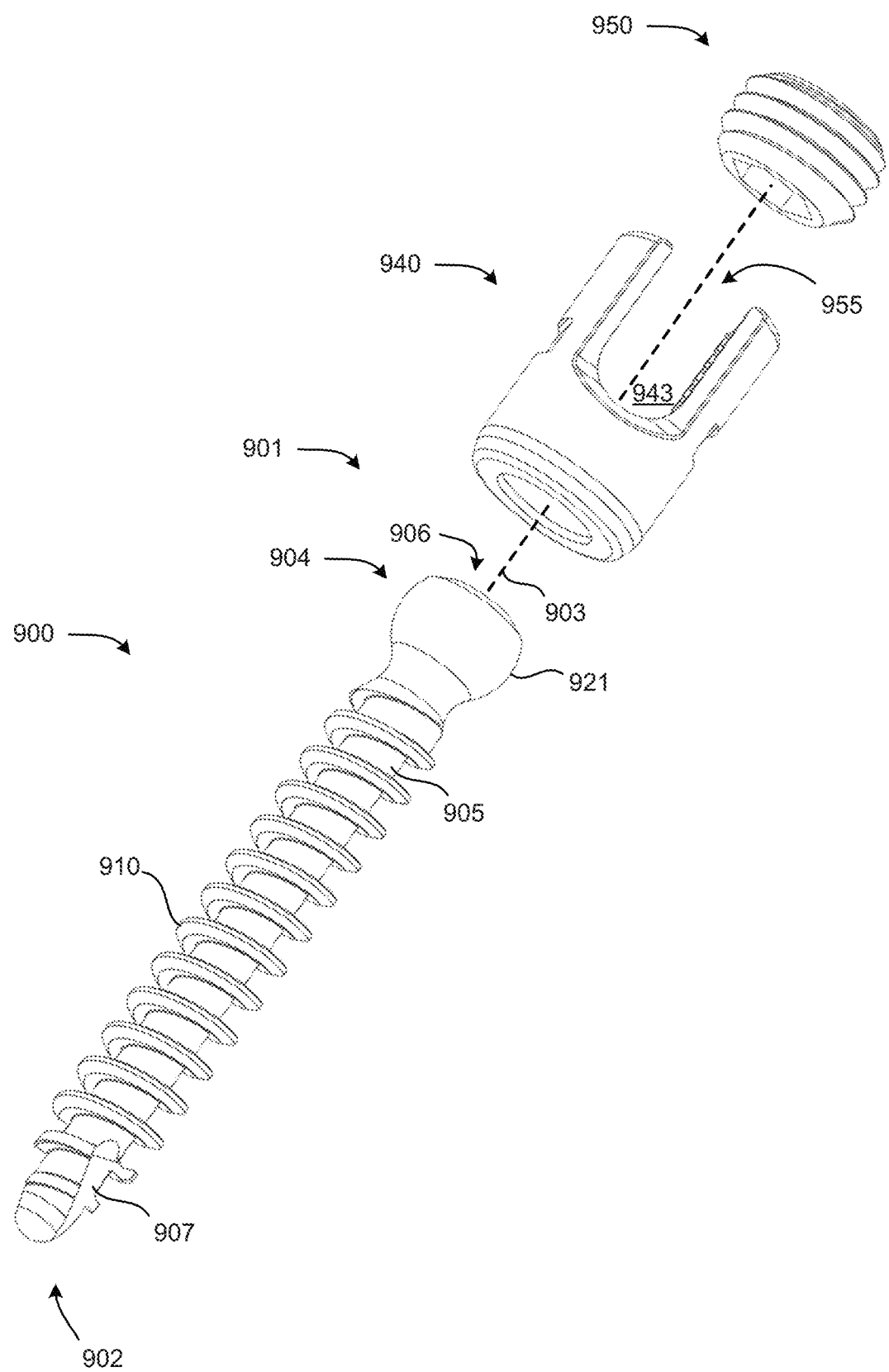
FIG. 9A illustrates an exploded view of a pedicle fastener stabilization system, according to an embodiment of the present disclosure.
Figure 9B:
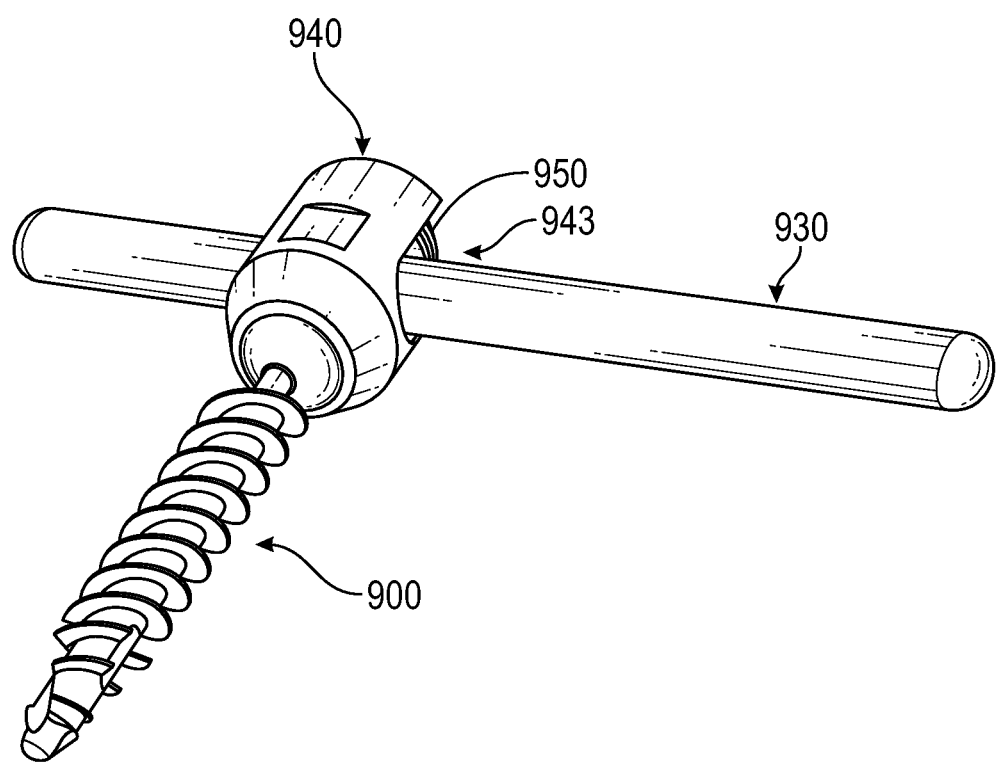
FIG. 9B illustrates the pedicle fastener stabilization system of FIG. 9A assembled together with a spinal stabilization rod.

In some embodiments, the spinal stabilization implement may comprise a spinal stabilization rod or rod (e.g., see rod 930 shown in FIG. 9B).

In some embodiments, the integrated tulip 840 may be configured to adjustably secure at least a part of the spinal stabilization implement to the integrated tulip 840 through the at least one opening 843.

In some embodiments, the integrated tulip 840 may include a locking member opening 855 configured to receive a locking member therein (e.g., see locking member 950 shown in FIG. 9A).

In some embodiments, the locking member may be configured to secure at least a part of the spinal stabilization rod received through the at least one opening 843 of the integrated tulip 840.

Figure 9C:
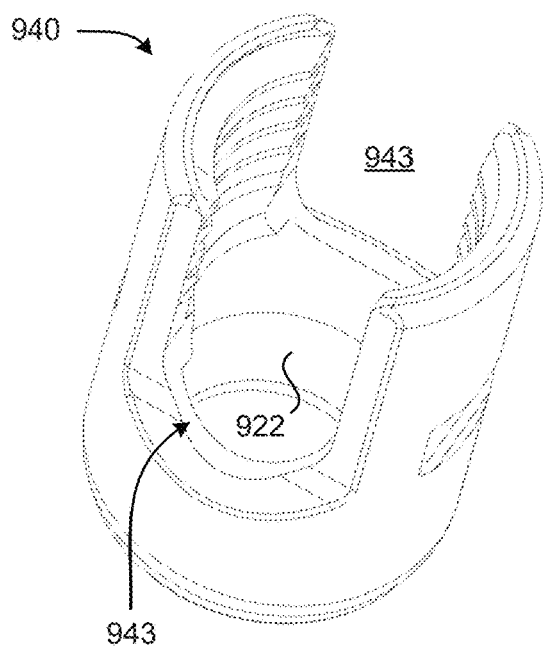
FIG. 9C illustrates a top perspective view of the discrete tulip shown in FIG. 9A.
Figure 9D:
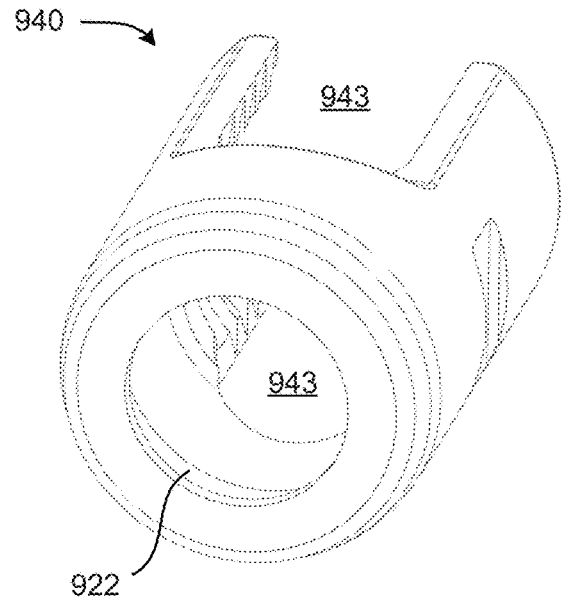
FIG. 9D illustrates a bottom perspective view of the discrete tulip.
Figure 9E:
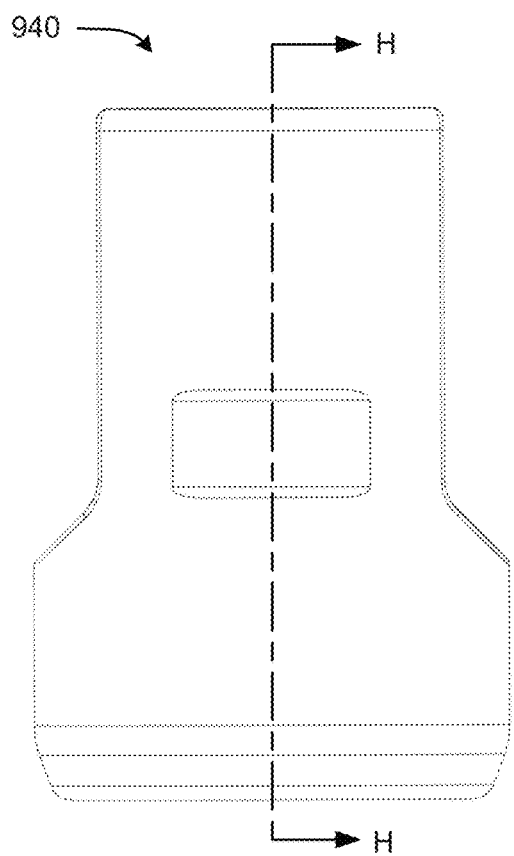
FIG. 9E illustrates a side view of the discrete tulip.
Figure 9F:
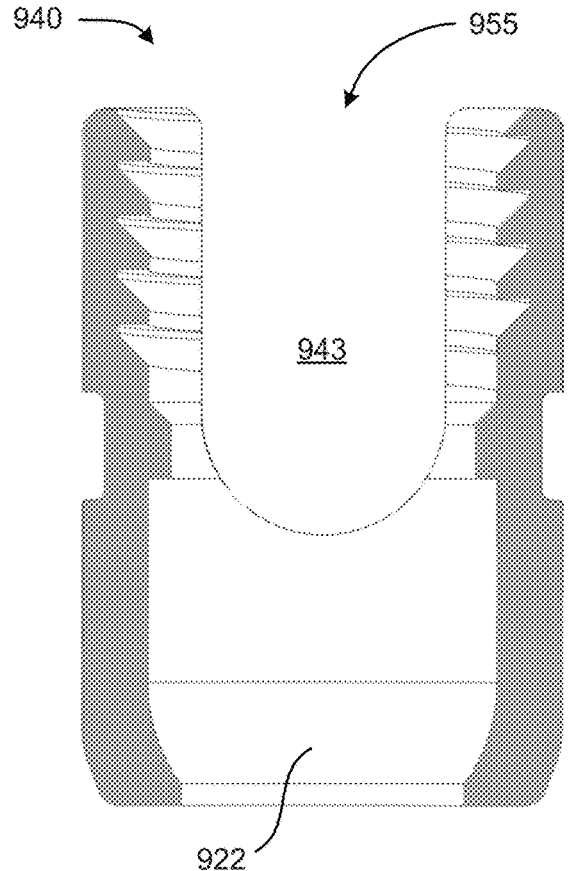
FIG. 9F illustrates a cross-sectional side view of the discrete tulip taken along the line H-H shown in FIG. 9E.

FIGS. 9A-9F illustrate various views of a pedicle fastener stabilization system, according to an embodiment of the present disclosure. Specifically, FIG. 9A illustrates an exploded view of the pedicle fastener stabilization system, FIG. 9B shows the pedicle fastener stabilization system of FIG. 9A assembled together (including a spinal stabilization rod), FIG. 9C illustrates a top perspective view of a discrete tulip or tulip 940 of the pedicle fastener stabilization system shown in FIG. 9A, FIG. 9D illustrates a bottom perspective view of the tulip 940, FIG. 9E illustrates a side view of the tulip 940, and FIG. 9F illustrates a cross-sectional side view of the tulip 940 taken along the line H-H shown in FIG. 9E.

As shown in FIG. 9A, the pedicle fastener stabilization system may generally include a pedicle bone fastener or fastener 900, the tulip 940, and the locking member 950. In some embodiments, the pedicle fastener stabilization system may also include a spinal stabilization rod or rod 930 that may be securable to the tulip 940 (see FIG. 9B).

The fastener 900 may generally include a shaft 905 having a proximal end 901, a distal end 902, and a longitudinal axis 903. The fastener 900 may also include a helical thread 910 disposed about the shaft 905 along the longitudinal axis 903 between the proximal and distal ends 901, 902 of the shaft 905. The fastener 900 may also include an integrated attachment feature located at the proximal end 901 of the shaft 905, such as a polyaxial head 904 having a first semi-spherical surface 921. The fastener 900 may additionally include a torque connection interface 906 formed in/on the polyaxial head 904 and a self-tapping feature 907 formed in the distal end 902 of the shaft 905.

In some embodiments, the helical thread 910 may comprise standard threading. In some embodiments, the helical thread 910 may comprise inverted threading. However, it will be understood that the fastener 900 may include any thread configuration, feature, or morphology described or contemplated herein to achieve optimal fixation within a given bone/tissue. For example, in some embodiments the helical thread 910 may comprise a first helical thread with standard or inverted threading comprising a first concave undercut surface, and the fastener 900 may also include a second helical thread (not shown) with standard or inverted threading adjacent the first helical thread comprising a second concave undercut surface, forming a "dual start" thread configuration. Moreover, it will also be understood that the fastener 900 may be utilized in conjunction with (or within) any system, method, or instrumentation described or contemplated herein.

In some embodiments, the polyaxial head 904 at the proximal end of the shaft 905 may be configured to be polyaxially-adjustably secured to a spinal stabilization implement.

In some embodiments, the spinal stabilization implement may comprise the tulip 940.

In some embodiments, the tulip 940 may include a second semi-spherical surface 922 that may be configured to engage the first semi-spherical surface 921 of the polyaxial head 904 to polyaxially-adjustably secure the tulip 940 to the polyaxial head 904 at any of a variety of relative orientations.

In some embodiments, the tulip 940 may include at least one opening 943 formed through one or more sides of the tulip 940.

In some embodiments, the tulip 940 may include two openings formed through opposing sides of the tulip 940.

In some embodiments, the at least one opening 943 may be configured to receive at least a part of a spinal stabilization rod or rod 930 therethrough, as shown in FIG. 9B.

In some embodiments, the tulip 940 may also include a locking member opening 955 configured to receive the locking member 950 therein.

In some embodiments, the tulip 940 may be configured to adjustably secure at least a part of the rod 930 to the tulip 940 by tightening the locking member 950 to compress the rod 930 between the tulip 940 and the locking member 950, as shown in FIG. 9B.

The fastener 900 may comprise any thread configuration, feature, or morphology described or contemplated herein to achieve optimal fixation within a vertebra, or within any other bone/tissue. Moreover, it will also be understood that the fastener 900 may be utilized in conjunction with (or within) any system, method, or instrumentation described or contemplated herein.

Figure 10A:
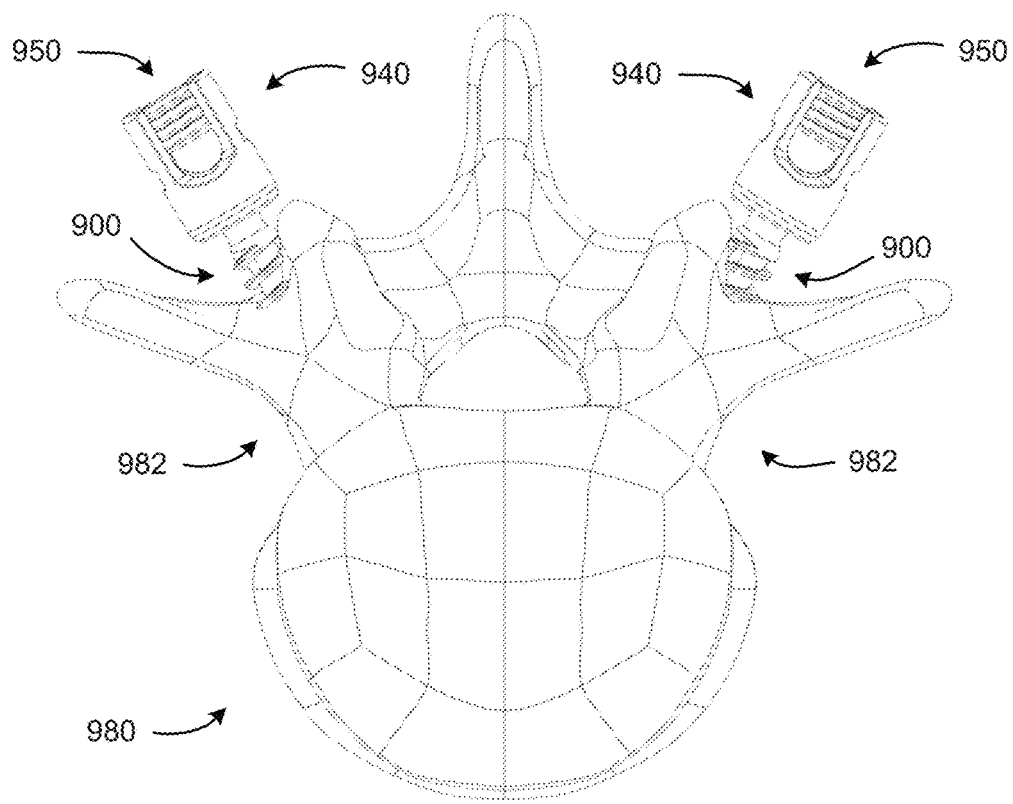
FIG. 10A illustrates a top view of a vertebral body with the pedicle fastener stabilization system of FIG. 9A inserted into pedicles of the vertebral body.
Figure 10B:
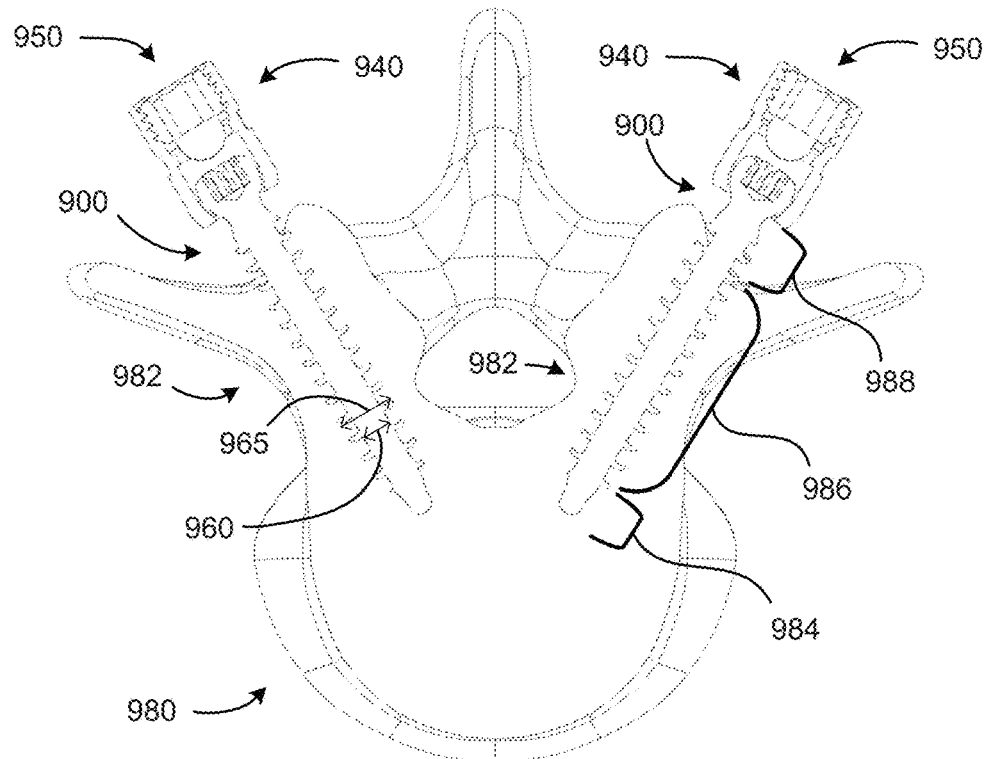
FIG. 10B illustrates a cross-sectional side view of FIG. 10A.

FIG. 10A illustrates a top view of a vertebral body 980 with the pedicle fastener stabilization system of FIG. 9A inserted into the pedicles 982 of the vertebral body 980, and FIG. 10B illustrates a cross-sectional side view of the vertebral body 980 of FIG. 10A.

In some embodiments, a method of implanting a polyaxial bone fastener assembly (e.g., such as the pedicle fastener stabilization system shown in FIGS. 9A-10B, or the bone fastener assembly shown in FIGS. 12A-12F, etc.) may generally include: (1) inserting a bone fastener into a bone, (2) adjusting an orientation of an implement to a selected orientation relative to an attachment feature of the bone fastener, and (3) attaching the implement to the attachment feature at the selected orientation.

In some embodiments, the bone fastener may include a shaft, a helical thread, and the attachment feature.

In some embodiments, the shaft may include a proximal end, a distal end, a longitudinal axis, and the helical thread disposed about the shaft along the longitudinal axis between the proximal and distal ends of the shaft.

In some embodiments, at least a portion of a minor diameter and/or a major diameter of the shaft/helical thread(s) may be constant to help prevent bone blowout during insertion of the bone fastener, as will be discussed below in more detail.

In some embodiments, the helical thread may include a first undercut surface and a second undercut surface.

In some embodiments, the first undercut surface may be angled toward one of the proximal end and the distal end of the shaft, and the second undercut surface may be angled toward the other one of the proximal end and the distal end of the shaft. However, it will be understood that the bone fastener may include any thread configuration, feature, or morphology described or contemplated herein to achieve optimal fixation within a given bone/tissue. For example, in some embodiments the bone fastener may comprise a first helical thread with standard or inverted threading, as well as a second helical thread with standard or inverted threading adjacent the first helical thread in a "dual start" thread configuration, etc.

In some embodiments, the attachment feature may be disposed at the proximal end of the shaft and configured to be adjustably secured to the implement.

In some embodiments, the attachment feature may be configured to be polyaxially-adjustably secured to the implement.

In some embodiments, the attachment feature may be coupled to the bone fastener or to the shaft of the bone fastener.

In some embodiments, adjusting the orientation of the implement to the selected orientation relative to the attachment feature may comprise polyaxially adjusting the orientation of the implement to a selected relative orientation, of a plurality of polyaxially-differentiated potential relative orientations, relative to the attachment feature.

In some embodiments, the attachment feature may be integrally formed with the bone fastener or the shaft of the bone fastener.

In some embodiments, the attachment feature may include a polyaxial head having a first semi-spherical surface and the implement may include a discrete tulip having a second semi-spherical surface configured to engage the first semi-spherical surface of the polyaxial head to polyaxially-adjustably secure the discrete tulip to the polyaxial head at any of a variety of relative orientations. For example, the second semi-spherical surface of the discrete tulip may be polyaxially adjusted to a selected orientation (of a plurality of polyaxially-differentiated potential relative orientations) relative to the first semi-spherical surface of the polyaxial head, and the discrete tulip may then be attached to the polyaxial head at the selected relative orientation.

In some embodiments, the discrete tulip may comprise at least one opening and a locking member configured to secure a rod received through the at least one opening to the discrete tulip at the selected relative orientation.

In some embodiments, the attachment feature may include a polyaxial head having a first semi-spherical surface, and the implement may include a radial head component having a second semi-spherical surface configured to engage the first semi-spherical surface and permit polyaxial articulation of the radial head component with respect to the polyaxial head, as will be discussed in more detail below with respect to FIGS. 12A-12F. However, in some embodiments the attachment feature may include a head that may rigidly couple with a radial head component, as will be discussed in more detail below with respect to FIGS. 14A-14I.

In some embodiments, the method may also include drilling a pilot hole (not shown) into the bone and inserting the shaft of the bone fastener into the pilot hole.

In some embodiments, the method may also include tapping (not shown) one or more bone threads in the bone to form one or more tapped bone threads about the pilot hole and inserting the helical thread(s) into the one or more tapped bone threads.

Bone blowout can occur when a bone fastener is inserted into a bone and generates a sufficient outwardly directed radial force on the bone to cause bone blowout due to the size/morphology of the bone fastener and/or the size/morphology of the bone hole receiving the bone fastener.

In some embodiments, a method of preventing bone blowout may generally include forming a hole in a bone (not shown), the hole having a bone hole diameter, and inserting a bone fastener into the hole having a minor diameter that is not greater than 5% larger the bone hole diameter. In this manner, an outwardly directed radial force applied to the bone by the minor diameter of the fastener may be reduced to prevent bone blowout.

In some embodiments, the shaft may include a proximal end, a distal end, and a longitudinal axis with at least one helical thread disposed about the shaft along the longitudinal axis between the proximal and distal ends of the shaft.

In some embodiments, at least a portion of the minor diameter of the shaft may be constant to help prevent bone blowout during insertion of the bone fastener. For example, a main portion of a bone fastener may exclude a pointed tip portion of the bone fastener (e.g., see the main portion 986 and the pointed tip portion 984 of the fastener 900 in FIG. 10B, as one non-limiting example). Moreover, in some embodiments, a main portion of a bone fastener may exclude a proximal portion of the bone fastener that may or may not be fully inserted into the bone (e.g., see the proximal portion 988 of the fastener 900 in FIG. 10B, as one non-limiting example). Thus, in some embodiments a minor diameter of a main portion of a bone fastener may be constant (e.g., see the minor diameter 960 of the main portion of the fastener 900 in FIG. 10B which is constant, as one non-limiting example).

In some embodiments, at least a portion of the major diameter of a fastener may also be constant to help prevent bone blowout from the threading of the bone fastener during insertion (e.g., see the major diameter 965 of the main portion of the fastener 900 in FIG. 10B which is constant, as one non-limiting example).

In some embodiments, the helical thread may include a first undercut surface and a second undercut surface.

In some embodiments, the first undercut surface may be angled toward one of the proximal end and the distal end of the shaft, and the second undercut surface may be angled toward the other one of the proximal end and the distal end of the shaft. However, it will be understood that the bone fastener may include any thread configuration, feature, or morphology described or contemplated herein to achieve optimal fixation within a given bone/tissue. For example, in some embodiments the bone fastener may comprise a first helical thread with standard or inverted threading, as well as a second helical thread with standard or inverted threading adjacent the first helical thread in a "dual start" thread configuration, etc.

In some embodiments, the minor diameter of at least a main portion of the shaft may be greater than the bone hole diameter. For example, the minor diameter of at least a main portion of the shaft may be greater than the bone hole diameter, but not greater than 5% larger the bone hole diameter.

In some embodiments, the minor diameter of at least a main portion of the shaft may not be greater than the bone hole diameter.

In some embodiments, the minor diameter of at least a main portion of the shaft may be equal to the bone hole diameter.

In some embodiments, the minor diameter of at least a main portion of the shaft may be less than the bone hole diameter.

In some embodiments, the minor diameter of the main portion of the shaft may be between 0 mm and 0.1 mm less than the bone hole diameter.

In some embodiments, the minor diameter of the main portion of the shaft may be at least 0.1 mm less than the bone hole diameter.

In some embodiments, the minor diameter of the main portion of the shaft may be between 0.1 mm and 0.2 mm less than the bone hole diameter.

In some embodiments, the minor diameter of the main portion of the shaft may be at least 0.2 mm less than the bone hole diameter.

However, it will be understood that at least a portion of the minor diameter of the shaft may any size that is less than, equal to, or greater than the bone hole diameter.

In these embodiments, the unique morphology of the thread designs disclosed herein allow for "over-drilling" a given bone hole to create a bone hole diameter that is equal to or greater than the minor diameter of at least a main portion of the shaft, while maintaining good bone purchase and loading characteristics provided by the unique morphology of the thread designs disclosed herein. In this manner, an over-drilled bone hole in combination with a smaller minor diameter and the unique morphology of the thread designs disclosed herein can achieve a lower radial outward load force that is placed on the bone by the minor diameter of the shaft in order to prevent bone blowout. This is in contrast to typical procedures that "under-drill" bone holes and rely on bone compaction by fasteners with larger minor diameters than the bone hole diameter in order to achieve sufficient bone purchase. However, this will result in higher radial outward load forces placed on the bone by the larger minor diameter of the shaft, thus increasing the risk of bone blowout.

In some embodiments, the method may also include tapping (not shown) one or more bone threads in the bone to form one or more tapped bone threads about the hole in the bone, and then inserting the helical thread(s) into the one or more tapped bone threads to further reduce an outwardly directed radial force applied to the bone by the helical thread(s) as the bone fastener is inserted into the bone.

Figure 11A:
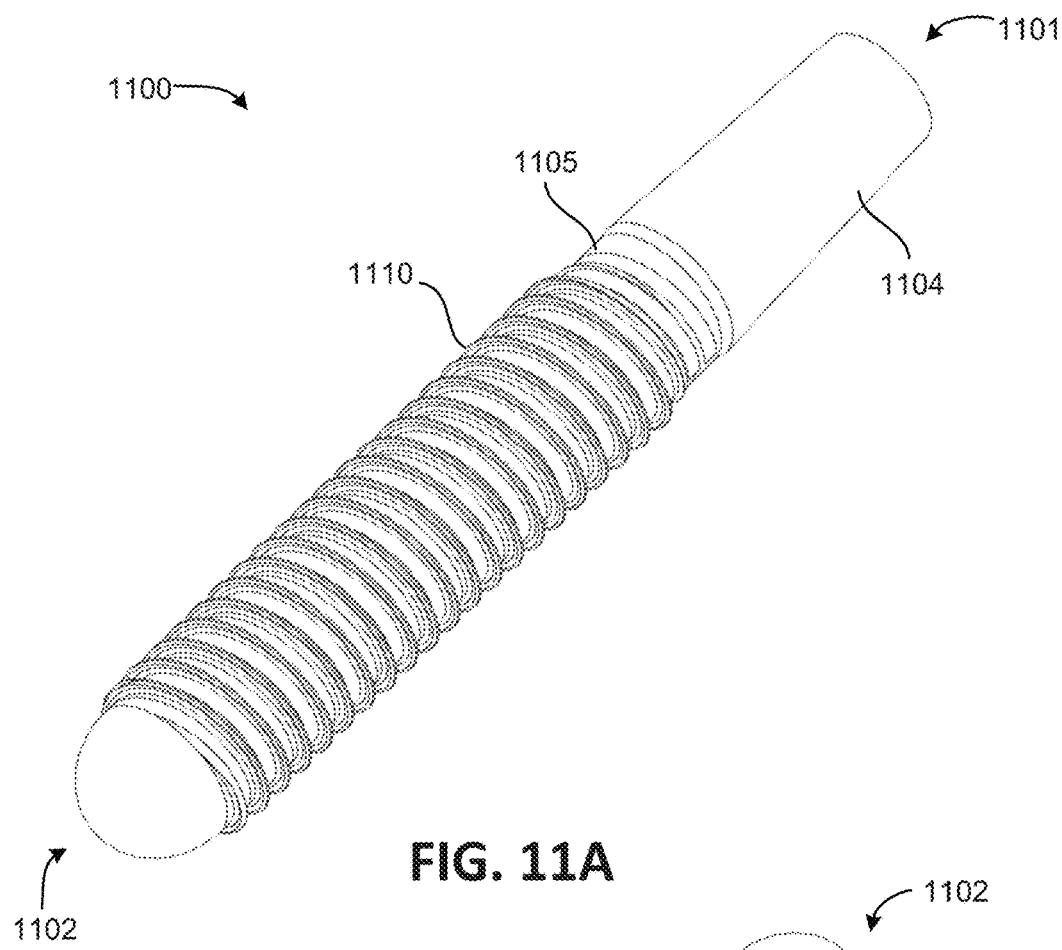
FIG. 11A illustrates a front perspective view of a threaded stem, according to an embodiment of the present disclosure.
Figure 11B:
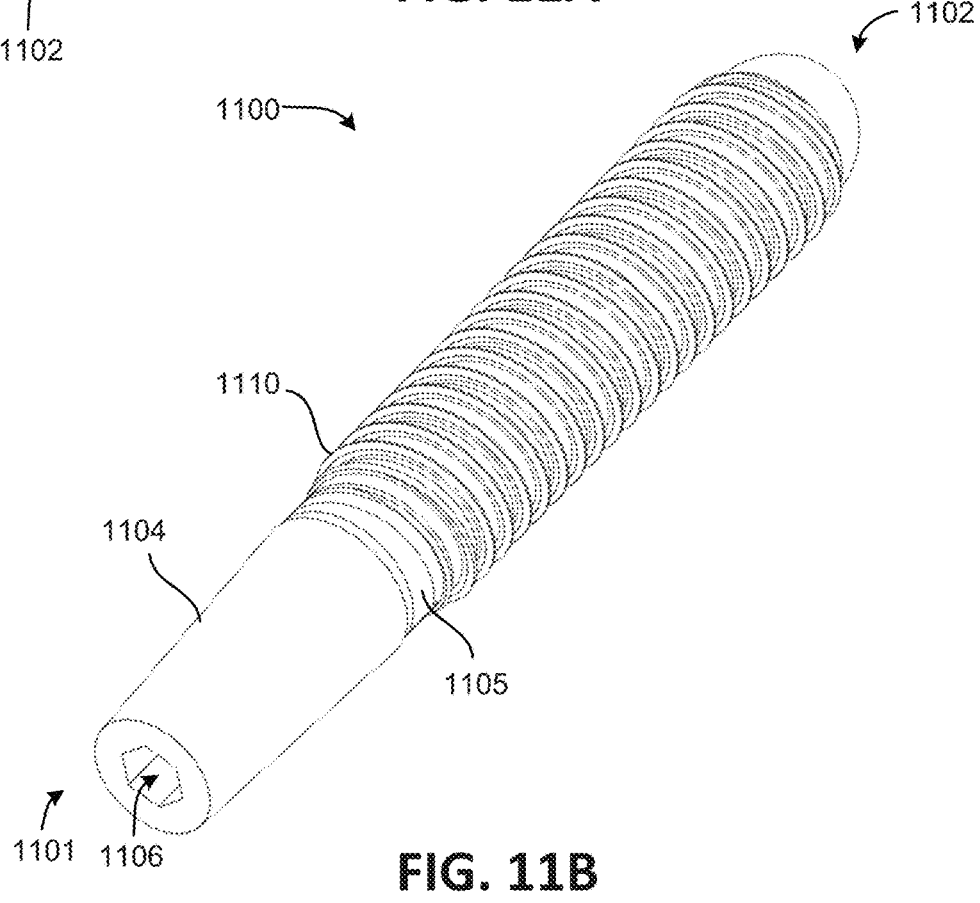
FIG. 11B illustrates a rear perspective view of the threaded stem of FIG. 11A.
Figure 11C:
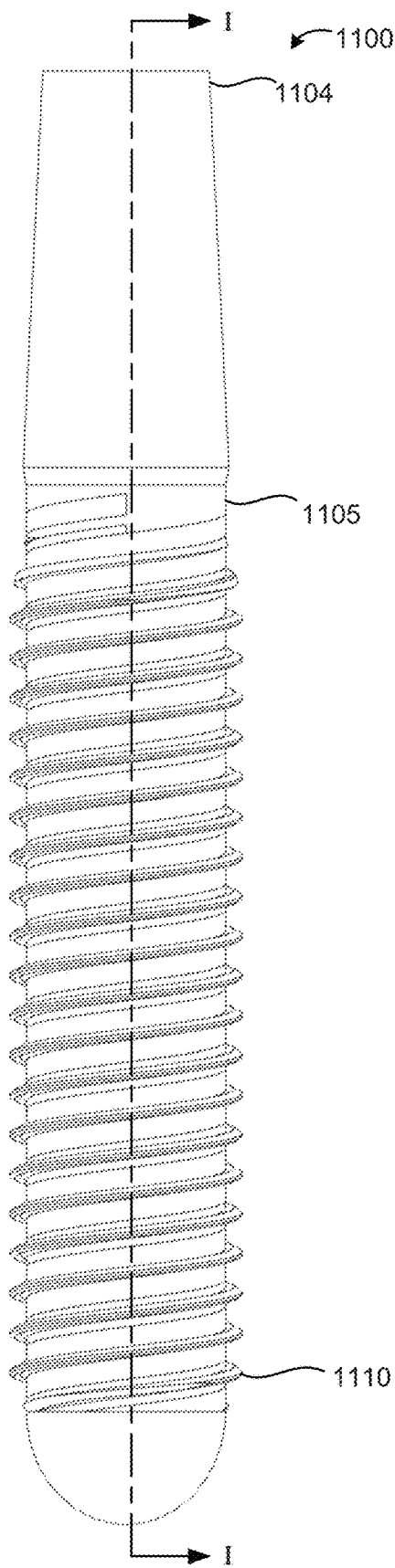
FIG. 11C illustrates a side view of the fastener of FIG. 11A.
Figure 11D:
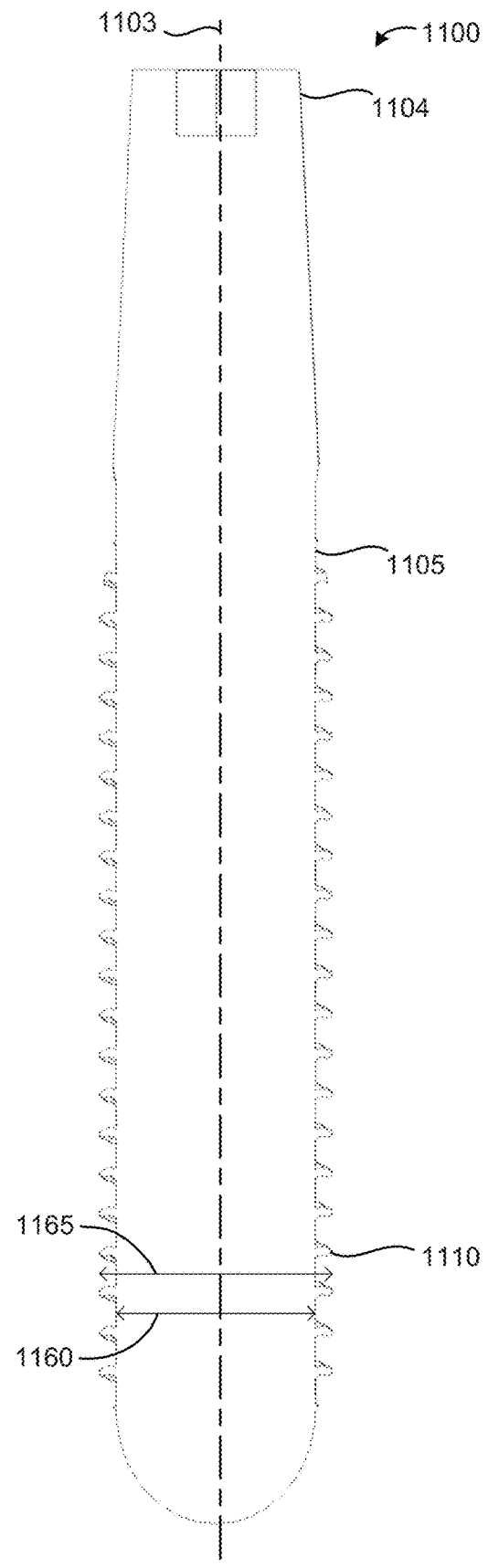
FIG. 11D illustrates a cross-sectional side view of the fastener of FIG. 11A taken along the line I-I shown in FIG. 11C.

FIGS. 11A-11D illustrate various views of a threaded stem, bone fastener, or fastener 1100, according to another embodiment of the present disclosure. Specifically, FIG. 11A is a front perspective view of the fastener 1100, FIG. 11B is a rear perspective view of the fastener 1100, FIG. 11C is a side view of the fastener 1100, and FIG. 11D is a cross-sectional side view of the fastener 1100 taken along the line I-I shown in FIG. 11C.

The fastener 1100 may generally include a shaft 1105 having a proximal end 1101, a distal end 1102, a longitudinal axis 1103, a helical thread 1110 disposed about the shaft 1105 along the longitudinal axis 1103, a head 1104, and a torque connection interface 1106 formed in/on the head 1104.

In some embodiments, the fastener 1100 may include the helical thread 1110 disposed about the shaft 1105 in a "single start" or "single lead" thread configuration having standard or inverted threading.

In some embodiments, the helical thread 1110 may include a first undercut surface, a second undercut surface, a third undercut surface, and a fourth open surface.

In some embodiments, the first undercut surface and the third undercut surface may be angled towards one of the proximal end 1101 and the distal end 1102 of the shaft 1105, and the second undercut surface and the fourth open surface may be angled towards the other one of the proximal end 1101 and the distal end 1102 of the shaft 1105.

However, it will be understood that the fastener 1100 may include any thread configuration, feature, or morphology described or contemplated herein to achieve optimal fixation within a given bone/tissue. For example, in some embodiments the helical thread 1110 may comprise a first helical thread with standard or inverted threading, and the fastener 1100 may also include a second helical thread (not shown) with standard or inverted threading adjacent the first helical thread, forming a "dual start" thread configuration, etc. Moreover, it will also be understood that the fastener 1100 may be utilized in conjunction with (or within) any system, method, or instrumentation described or contemplated herein.

In some embodiments, at least a portion of the fastener 1100 may be sized, shaped, and configured for use within an intramedullary canal (IMC) of a bone. For example, in some embodiments the fastener 1100 may be sized, shaped, and configured for use within an IMC as a transfemoral stem (or transfemoral stem abutment), a humeral stem, a tibial stem, etc. However, it will also be understood that the fastener 1100 may be sized, shaped, and configured for use within any IMC of any bone, and/or for any other suitable procedure or application outside of an IMC of a bone.

In some embodiments, the fastener 1100 may include a minor diameter 1160 and a major diameter 1165, as shown in FIG. 11D.

In some embodiments, a ratio of the major diameter 1165 to the minor diameter 1160 may be less than 1.50.

In some embodiments, a ratio of the major diameter 1165 to the minor diameter 1160 may be less than 1.25.

In some embodiments, a ratio of the major diameter 1165 to the minor diameter 1160 may be less than 1.10.

In some embodiments, a ratio of the major diameter 1165 to the minor diameter 1160 may be less than 1.05.

In some embodiments, at least a portion of the minor diameter 1160 of the shaft 1105 may be constant to help prevent bone blowout during insertion of the fastener 1100.

In some embodiments, at least a portion of the major diameter 1165 of the shaft 1105 may be constant to help prevent bone blowout during insertion of the fastener 1100.

Figure 12A:
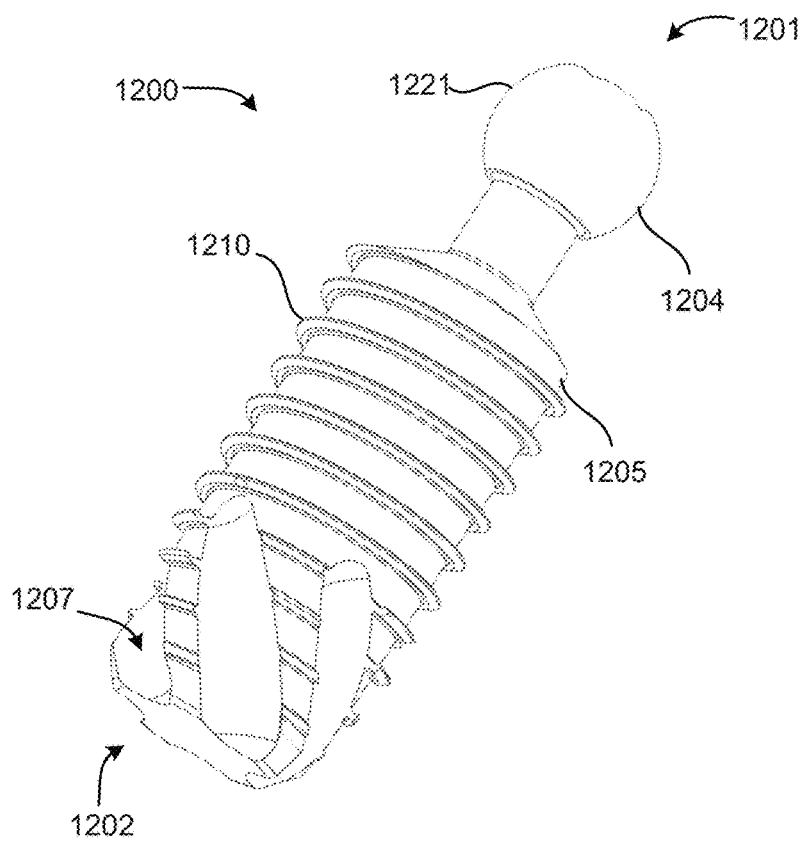
FIG. 12A illustrates a front perspective view of a threaded stem, according to another embodiment of the present disclosure.
Figure 12B:
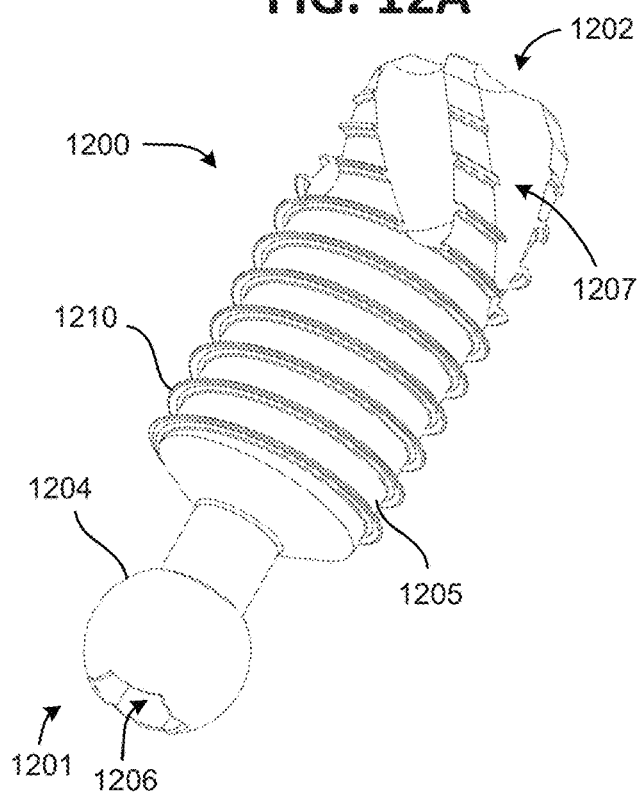
FIG. 12B illustrates a rear perspective view of the threaded stem of FIG. 12A.

FIGS. 12A-12F illustrate various views of a threaded stem, bone fastener, or fastener 1200, according to another embodiment of the present disclosure. Specifically, FIG. 12A is a front perspective view of the fastener 1200, FIG.

Figure 12E:
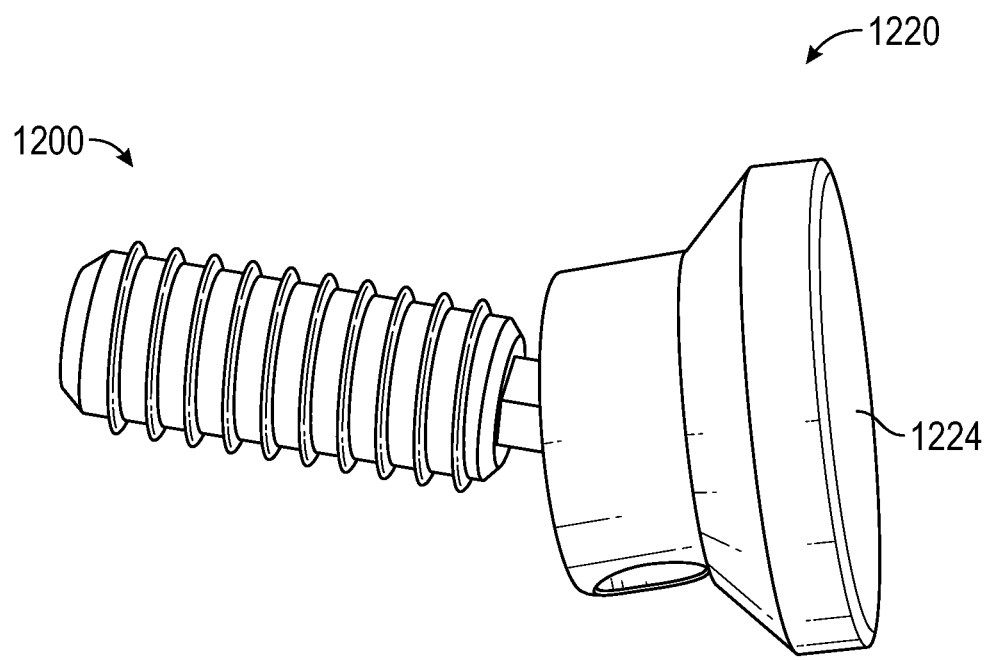
FIG. 12E illustrates a perspective side view of the threaded stem of FIG. 12A coupled to an implant.
Figure 12F:
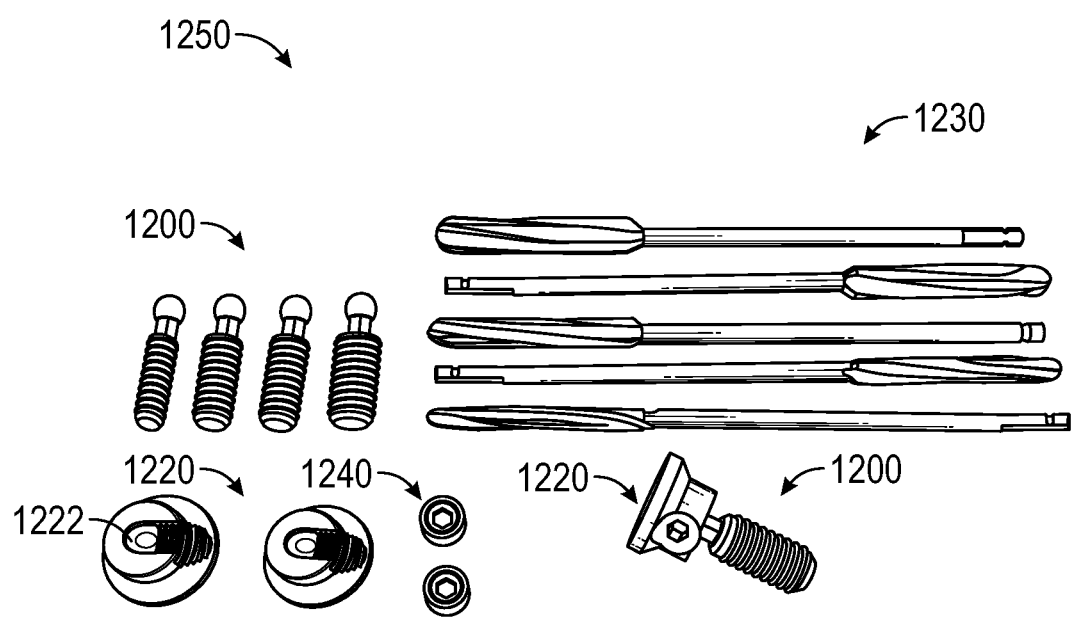
FIG. 12F illustrates a system comprising the threaded stem of FIG. 12A.

12B is a rear perspective view of the fastener 1200, FIG. 12C is a side view of the fastener 1200, FIG. 12D is a cross-sectional side view of the fastener 1200 taken along the line J-J shown in FIG. 12C, FIG. 12E is a perspective side view of the fastener 1200 coupled to a radial head component 1220, and FIG. 12F shows a system/kit 1250 including the fastener 1200.

The fastener 1200 may generally include a shaft 1205 having a proximal end 1201, a distal end 1202, a longitudinal axis 1203, a helical thread 1210, a polyaxial head 1204, a torque connection interface 1206 formed in/on the polyaxial head 1204, and one or more self-tapping features 1207.

In some embodiments, the fastener 1200 may include the helical thread 1210 disposed about the shaft 1205 in a "single start" or "single lead" thread configuration having a standard or inverted orientation.

In some embodiments, the helical thread 1210 may include a first undercut surface and a second undercut surface.

In some embodiments, the first undercut surface may be angled toward one of the proximal end 1201 and the distal end 1202 of the shaft 1205, and the second undercut surface may be angled toward the other one of the proximal end 1201 and the distal end 1202 of the shaft 1205.

In some embodiments, the helical thread 1210 may include a first undercut surface, a second undercut surface, a third undercut surface, and a fourth open surface.

In some embodiments, the first undercut surface and the third undercut surface may be angled towards one of the proximal end 1201 and the distal end 1202 of the shaft 1205, and the second undercut surface and the fourth open surface may be angled towards the other one of the proximal end 1201 and the distal end 1202 of the shaft 1205.

However, it will be understood that the fastener 1200 may include any thread configuration, feature, or morphology described or contemplated herein to achieve optimal fixation within a given bone/tissue. For example, in some embodiments the helical thread 1210 may comprise a first helical thread with standard or inverted threading, and the fastener 1200 may also include a second helical thread (not shown) with standard or inverted threading adjacent the first helical thread, forming a "dual start" thread configuration, etc. Moreover, it will also be understood that the fastener 1200 may be utilized in conjunction with (or within) any system, method, or instrumentation described or contemplated herein.

In some embodiments, at least a portion of the fastener 1200 may be sized, shaped, and configured for use within an IMC of a bone. For example, in some embodiments the fastener 1200 may be sized, shaped, and configured for use within an IMC of a radial bone as a threaded radial stem, etc. However, it will also be understood that the fastener 1200 may be sized, shaped, and configured for use within any IMC of any bone, and/or for any other suitable procedure or application outside of an IMC of a bone.

In some embodiments, the fastener 1200 may include a minor diameter 1260 and a major diameter 1265, as shown in FIG. 12D.

In some embodiments, a ratio of the major diameter 1265 to the minor diameter 1260 may be less than 1.50.

In some embodiments, a ratio of the major diameter 1265 to the minor diameter 1260 may be less than 1.25.

In some embodiments, a ratio of the major diameter 1265 to the minor diameter 1260 may be less than 1.10.

In some embodiments, a ratio of the major diameter 1265 to the minor diameter 1260 may be less than 1.05.

In some embodiments, at least a portion of the minor diameter 1260 of the shaft 1205 may be constant to help prevent bone blowout during insertion of the fastener 1200.

In some embodiments, at least a portion of the major diameter 1265 of the shaft 1205 may be constant to help prevent bone blowout during insertion of the fastener 1200.

In some embodiments, an attachment feature may be located at the proximal end 1201 of the shaft 1205 and configured to be adjustably secured to an implement, such as the radial head component 1220 or a glenoid component (not shown), etc.

In some embodiments, the attachment feature may comprise a polyaxial head 1204 that may be coupled to, or integrally formed with, the proximal end 1201 of the shaft 1205.

In some embodiments, the polyaxial head 1204 may include a first semi-spherical surface 1221.

In some embodiments, the radial head component 1220 (or a glenoid component, etc.) may be coupled to the polyaxial head 1204 of the fastener 1200 for utilization in a radial head arthroplasty procedure, a glenoid procedure, etc.

In some embodiments, the radial head component 1220 may include a second semi-spherical surface 1222 configured to engage the first semi-spherical surface 1221 and permit polyaxial articulation of the radial head component 1220 with respect to the polyaxial head 1204.

In some embodiments, the radial head component 1220 may include a concave articulation surface 1224 configured to receive a convex articulation surface (not shown) to form a prosthetic joint.

In some embodiments, a system/kit 1250 may comprise one or more drill bits 1230 of varying sizes to form pilot holes of varying size in a radial bone (not shown). The system/kit 1250 may also comprise one or more fasteners 1200 of varying size, one or more radial head components 1220 of varying size, and one or more couplers 1240 for coupling a radial head component 1220 to a fastener 1200, etc.

Figure 13A:
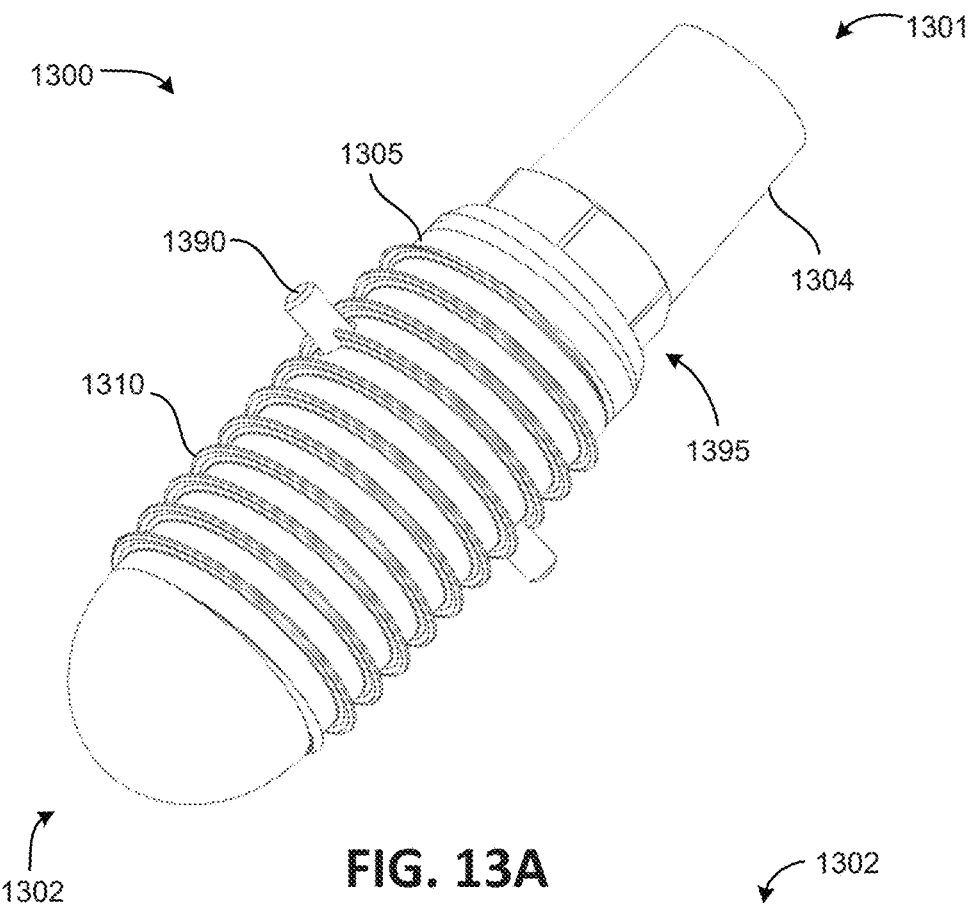
FIG. 13A illustrates a front perspective view of a threaded stem, according to another embodiment of the present disclosure.
Figure 13B:
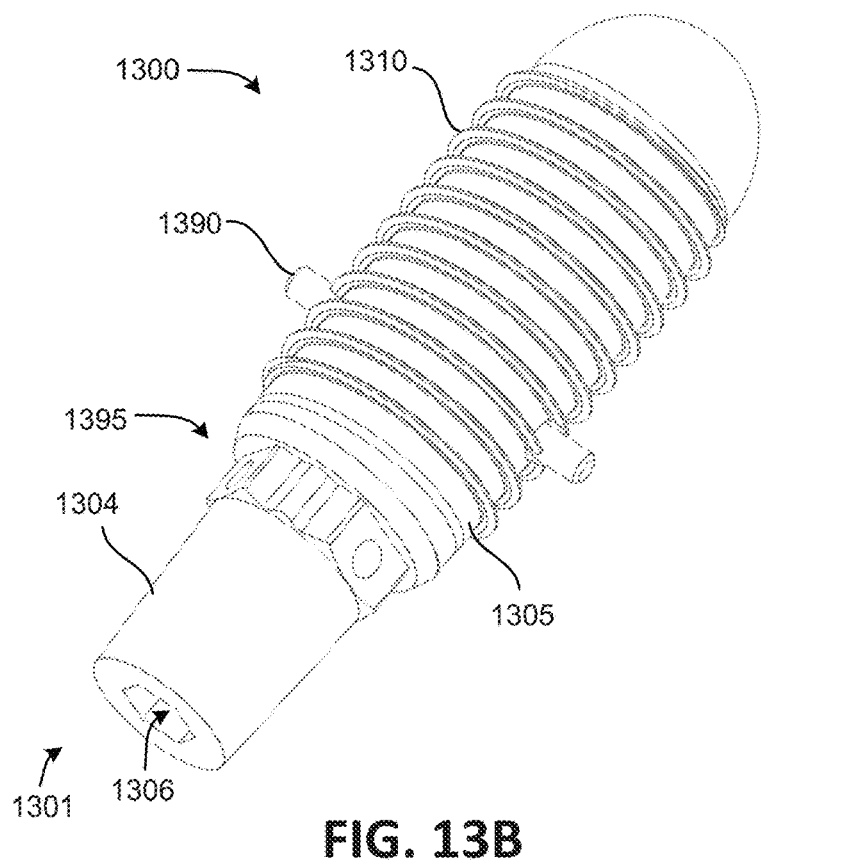
FIG. 13B illustrates a rear perspective view of the threaded stem of FIG. 13A.
Figure 13C:
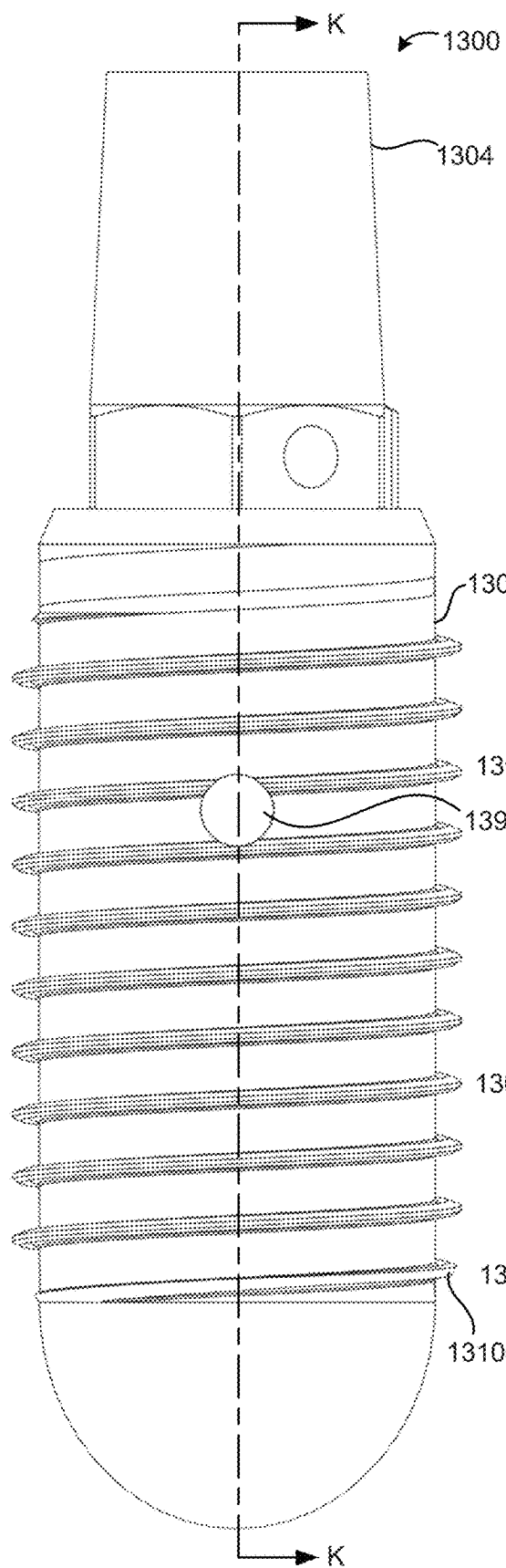
FIG. 13C illustrates a side view of the fastener of FIG. 13A.
Figure 13D:
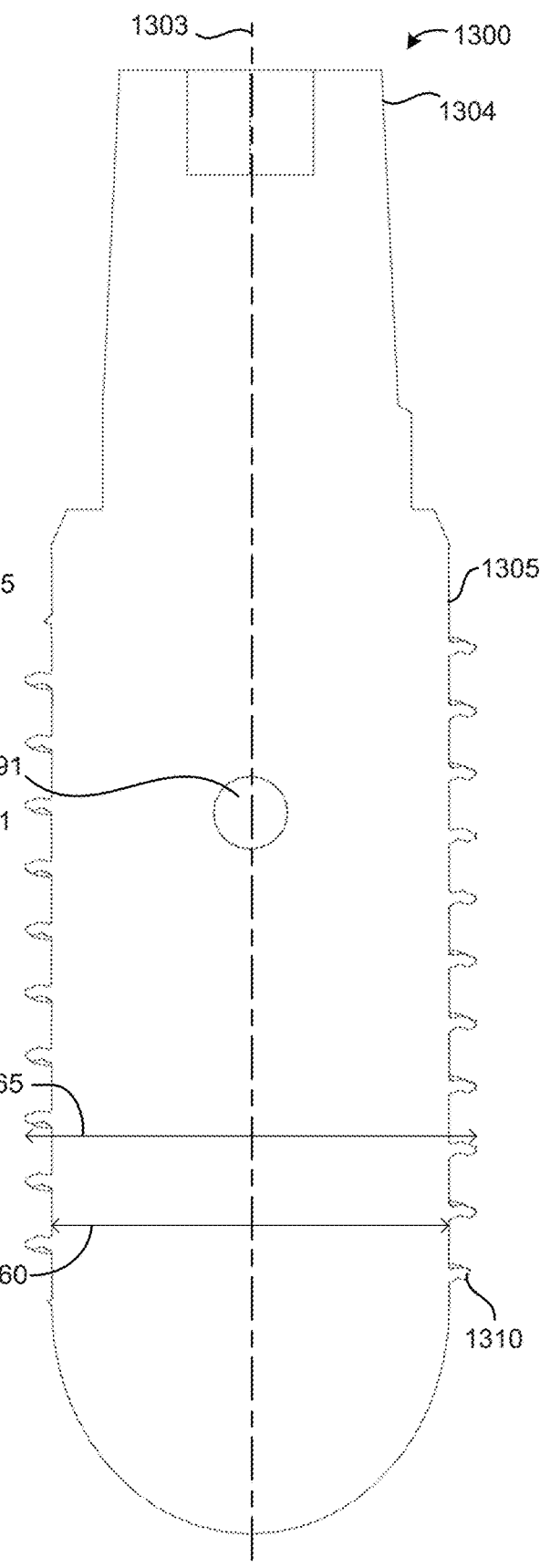
FIG. 13D illustrates a cross-sectional side view of the fastener of FIG. 13A taken along the line K-K shown in FIG. 13C.

FIGS. 13A-13D illustrate various views of a threaded stem, bone fastener, or fastener 1300, according to another embodiment of the present disclosure. Specifically, FIG. 13A is a front perspective view of the fastener 1300, FIG. 13B is a rear perspective view of the fastener 1300, FIG. 13C is a side view of the fastener 1300, and FIG. 13D is a cross-sectional side view of the fastener 1300 taken along the line K-K shown in FIG. 13C.

The fastener 1300 may generally include a shaft 1305 having a proximal end 1301, a distal end 1302, a longitudinal axis 1303, a helical thread 1310 disposed about the shaft 1305 along the longitudinal axis 1303, a head 1304, and a torque connection interface 1306 formed in/on the head 1304.

In some embodiments, the fastener 1300 may include the helical thread 1310 disposed about the shaft 1305 in a "single start" or "single lead" thread configuration having standard or inverted threading.

In some embodiments, the helical thread 1310 may include a first undercut surface and a second undercut surface.

In some embodiments, the first undercut surface may be angled toward one of the proximal end 1301 and the distal end 1302 of the shaft 1305, and the second undercut surface may be angled toward the other one of the proximal end 1301 and the distal end 1302 of the shaft 1305.

In some embodiments, the helical thread 1310 may include a first undercut surface, a second undercut surface, a third undercut surface, and a fourth open surface.

In some embodiments, the first undercut surface and the third undercut surface may be angled towards one of the proximal end 1301 and the distal end 1302 of the shaft 1305, and the second undercut surface and the fourth open surface may be angled towards the other one of the proximal end 1301 and the distal end 1302 of the shaft 1305.

However, it will be understood that the fastener 1300 may include any thread configuration, feature, or morphology described or contemplated herein to achieve optimal fixation within a given bone/tissue. For example, in some embodiments the helical thread 1310 may comprise a first helical thread with standard or inverted threading, and the fastener 1300 may also include a second helical thread (not shown) with standard or inverted threading adjacent the first helical thread, forming a "dual start" thread configuration, etc. Moreover, it will also be understood that the fastener 1300 may be utilized in conjunction with (or within) any system, method, or instrumentation described or contemplated herein.

In some embodiments, at least a portion of the fastener 1300 may be sized, shaped, and configured for use within an intramedullary canal (IMC) of a bone. For example, in some embodiments the fastener 1300 may be sized, shaped, and configured for use within an IMC as a transfemoral stem (or transfemoral stem abutment), a humeral stem, a tibial stem, etc. However, it will also be understood that the fastener 1300 may be sized, shaped, and configured for use within any IMC of any bone, and/or for any other suitable procedure or application outside of an IMC of a bone.

In some embodiments, the fastener 1300 may include a pin hole 1391 formed through the shaft 1305 of the fastener 1300. The pin hole 1391 may be configured to receive an anti-rotation pin 1390 therethrough. In this manner, the anti-rotation pin 1390 may prevent the fastener 1300 from rotating and/or loosening once the fastener 1300 has been implanted within a bone.

In some embodiments, the fastener 1300 may be utilized in a limb salvage procedure to prevent amputation and/or mitigate the need for additional amputation.

In some embodiments, the fastener 1300 may include an attachment feature 1395 that may be configured to removably couple with an implement, such as a prosthetic component (not shown). For example, the fastener 1300 may be inserted within an intramedullary canal of a long bone (e.g., a femur, a humerus, etc.). Once the fastener 1300 has achieved sufficient osseointegration within the long bone, another prosthetic component such as an abutment (not shown), etc., may be removably coupled to the fastener 1300 via the attachment feature 1395 and may extend outside the skin of the patient to connect with a prosthetic limb (e.g., a prosthetic arm, leg, foot, etc., not shown), as one non-limiting example.

In some embodiments, the fastener 1300 may include a minor diameter 1360 and a major diameter 1365, as shown in FIG. 13D.

In some embodiments, a ratio of the major diameter 1365 to the minor diameter 1360 may be less than 1.50.

In some embodiments, a ratio of the major diameter 1365 to the minor diameter 1360 may be less than 1.25.

In some embodiments, a ratio of the major diameter 1365 to the minor diameter 1360 may be less than 1.10.

In some embodiments, a ratio of the major diameter 1365 to the minor diameter 1360 may be less than 1.05.

In some embodiments, at least a portion of the minor diameter 1360 of the shaft 1305 may be constant to help prevent bone blowout during insertion of the fastener 1300.

In some embodiments, at least a portion of the major diameter 1365 of the shaft 1305 may be constant to help prevent bone blowout during insertion of the fastener 1300.

Figure 14A:
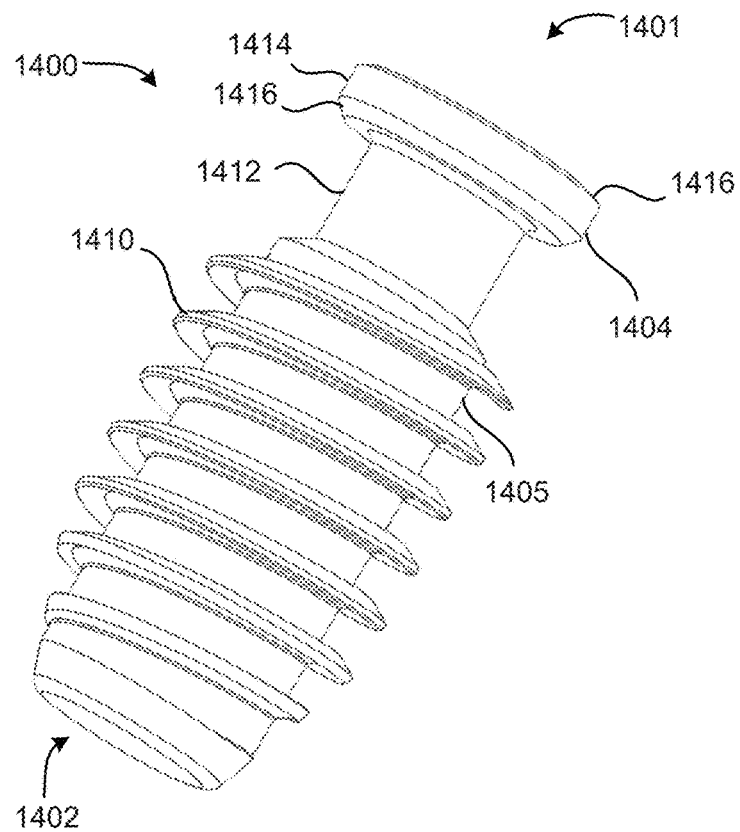
FIG. 14A illustrates a front perspective view of a threaded stem, according to another embodiment of the present disclosure.
Figure 14B:
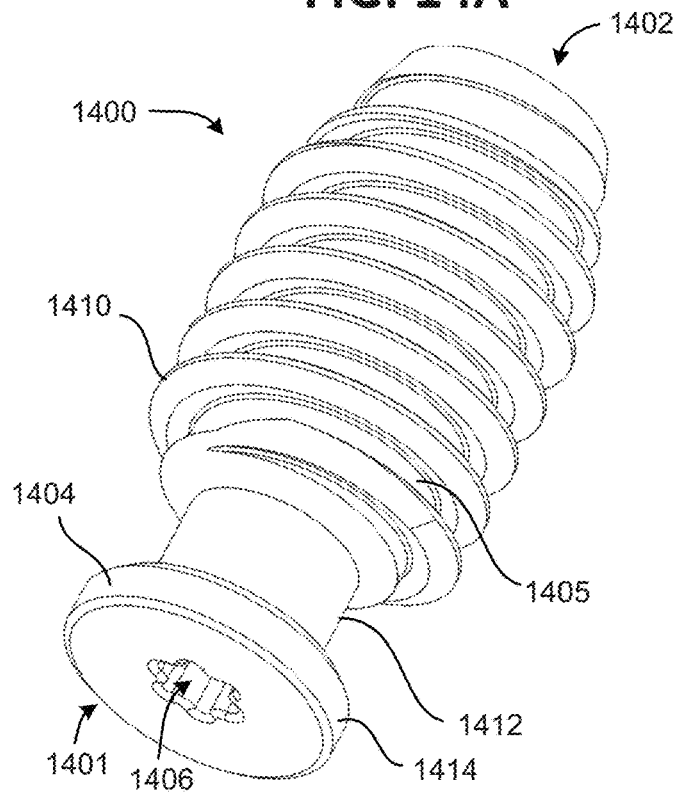
FIG. 14B illustrates a rear perspective view of the threaded stem of FIG. 14A.
Figures 14C, 14D:
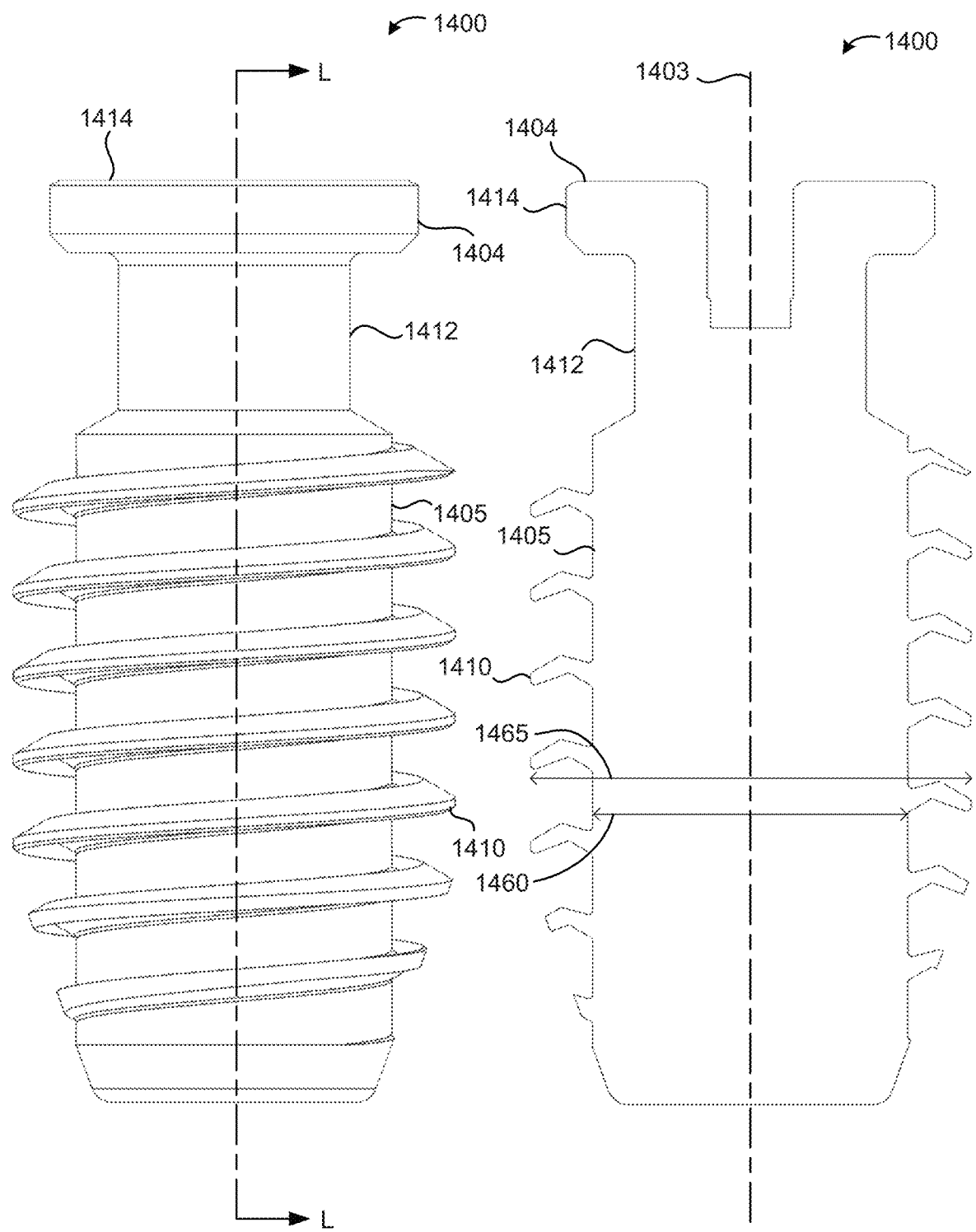
FIG. 14C illustrates a side view of the fastener of FIG. 14A.
FIG. 14D illustrates a cross-sectional side view of the fastener of FIG. 14A taken along the line L-L shown in FIG. 14C.
Figure 14E:
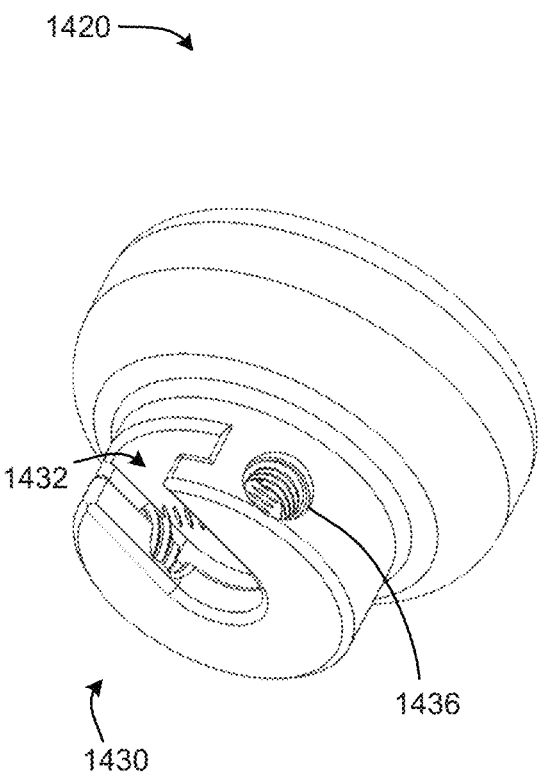
FIG. 14E illustrates a front perspective view of a radial head component, according to an embodiment of the present disclosure.
Figure 14F:
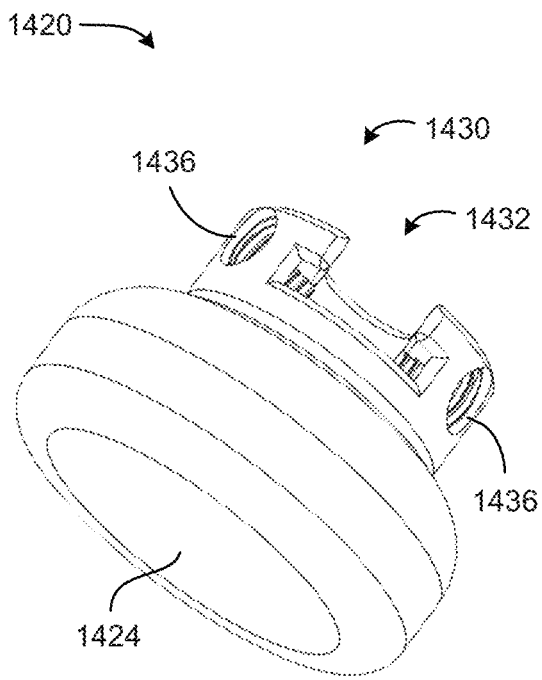
FIG. 14F illustrates a rear perspective view of the radial head component of FIG. 14E.
Figure 14G:
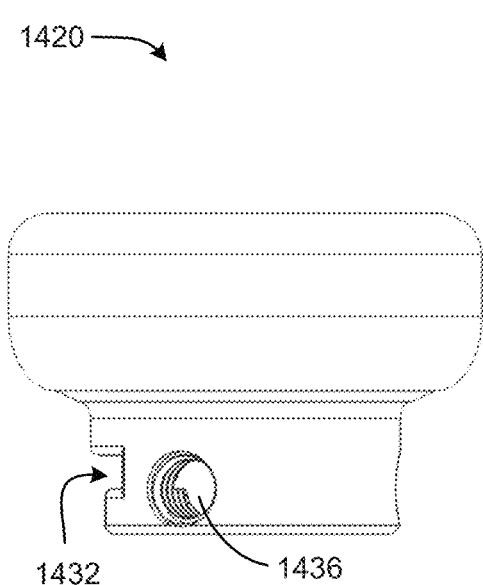
FIG. 14G illustrates a side view of the radial head component of FIG. 14E.
Figure 14H:
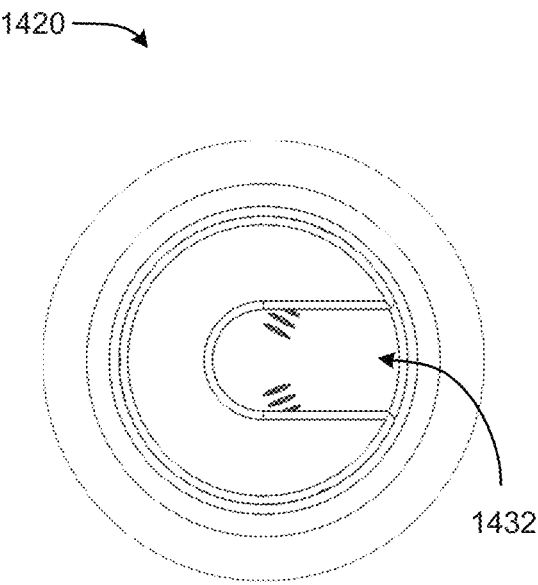
FIG. 14H illustrates a bottom view of the radial head component of FIG. 14E.
Figure 14I:
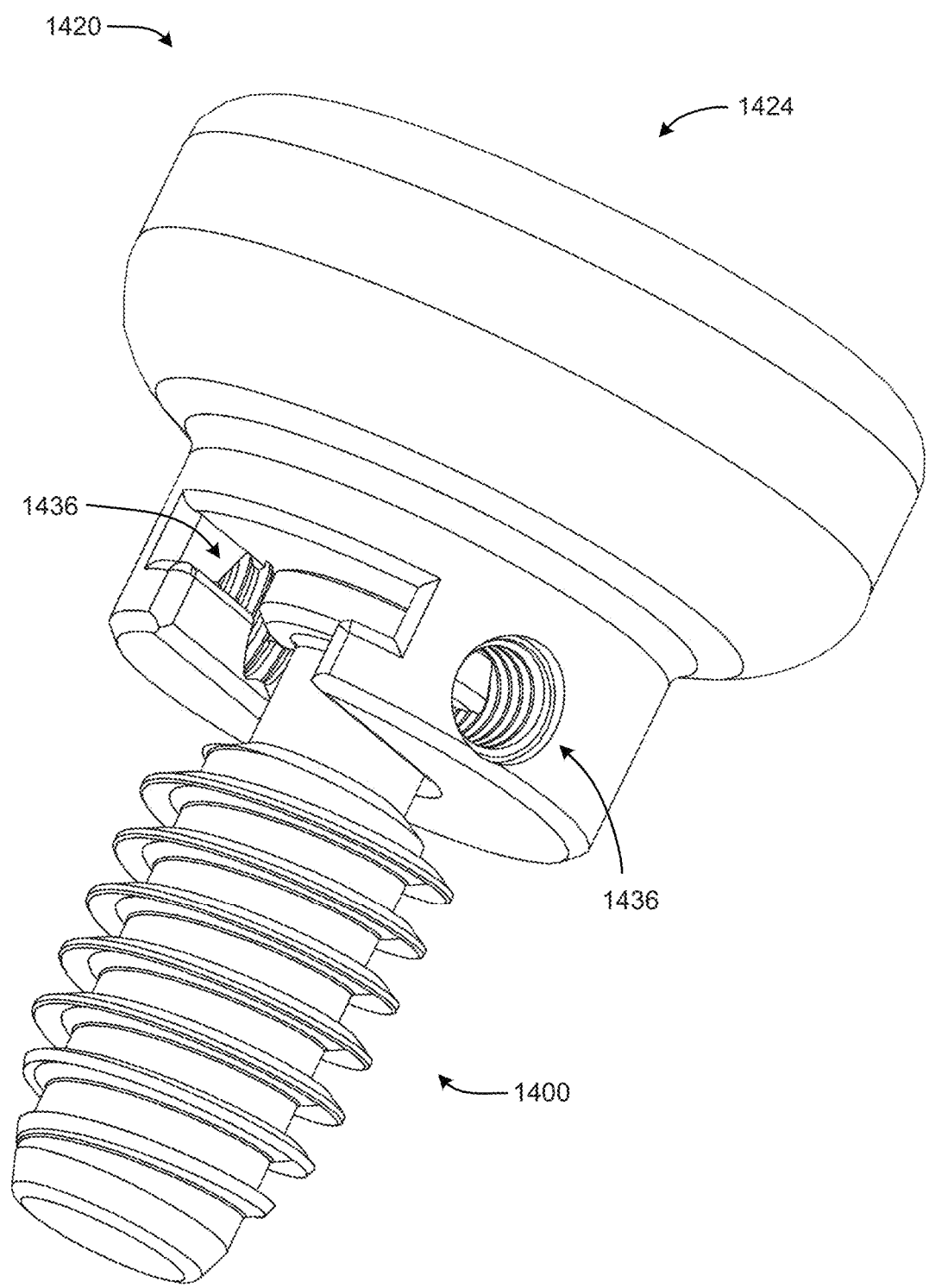
FIG. 14I illustrates an assembly comprising the threaded stem of FIG. 14A and the radial head component of FIG. 14E.

FIGS. 14A-14F illustrate various views of a threaded stem, bone fastener, or fastener 1400, according to another embodiment of the present disclosure. Specifically, FIG. 14A is a front perspective view of the fastener 1400, FIG. 14B is a rear perspective view of the fastener 1400, FIG. 14C is a side view of the fastener 1400, FIG. 14D is a cross-sectional side view of the fastener 1400 taken along the line L-L shown in FIG. 14C. FIG. 14E is a front perspective view of a radial head component 1420 that may be utilized with the fastener 1400, FIG. 14F is a rear perspective view of the radial head component 1420, FIG. 14G is a side view of the radial head component 1420, FIG. 14H is a bottom view of the radial head component 1420, and FIG. 14I is a side view of an assembly comprising the radial head component 1420 and the fastener 1400.

The fastener 1400 may generally include a shaft 1405 having a proximal end 1401, a distal end 1402, a longitudinal axis 1403, a helical thread 1410, an attachment feature or head 1404, a torque connection interface 1406 formed in/on the head 1404, and one or more self-tapping features 1407.

In some embodiments, the fastener 1400 may include the helical thread 1410 disposed about the shaft 1405 in a "single start" or "single lead" thread configuration having a standard or inverted orientation.

In some embodiments, the helical thread 1410 may include a first undercut surface and a second undercut surface.

In some embodiments, the first undercut surface may be angled toward one of the proximal end 1401 and the distal end 1402 of the shaft 1405, and the second undercut surface may be angled toward the other one of the proximal end 1401 and the distal end 1402 of the shaft 1405.

In some embodiments, the helical thread 1410 may include a first undercut surface, a second undercut surface, a third undercut surface, and a fourth open surface.

In some embodiments, the first undercut surface and the third undercut surface may be angled towards one of the proximal end 1401 and the distal end 1402 of the shaft 1405, and the second undercut surface and the fourth open surface may be angled towards the other one of the proximal end 1401 and the distal end 1402 of the shaft 1405.

However, it will be understood that the fastener 1400 may include any thread configuration, feature, or morphology described or contemplated herein to achieve optimal fixation within a given bone/tissue. For example, in some embodiments the helical thread 1410 may comprise a first helical thread with standard or inverted threading, and the fastener 1400 may also include a second helical thread (not shown) with standard or inverted threading adjacent the first helical thread, forming a "dual start" thread configuration, etc. Moreover, it will also be understood that the fastener 1400 may be utilized in conjunction with (or within) any system, method, or instrumentation described or contemplated herein.

In some embodiments, at least a portion of the fastener 1400 may be sized, shaped, and configured for use within an IMC of a bone. For example, in some embodiments the fastener 1400 may be sized, shaped, and configured for use within an IMC of a radial bone as a threaded radial stem, etc. However, it will also be understood that the fastener 1400 may be sized, shaped, and configured for use within any IMC of any bone, and/or for any other suitable procedure or application outside of an IMC of a bone.

In some embodiments, the fastener 1400 may include a minor diameter 1460 and a major diameter 1465, as shown in FIG. 14D.

In some embodiments, a ratio of the major diameter 1465 to the minor diameter 1460 may be less than 1.50.

In some embodiments, a ratio of the major diameter 1465 to the minor diameter 1460 may be less than 1.25.

In some embodiments, a ratio of the major diameter 1465 to the minor diameter 1460 may be less than 1.10.

In some embodiments, a ratio of the major diameter 1465 to the minor diameter 1460 may be less than 1.05.

In some embodiments, at least a portion of the minor diameter 1460 of the shaft 1405 may be constant to help prevent bone blowout during insertion of the fastener 1400.

In some embodiments, at least a portion of the major diameter 1465 of the shaft 1405 may be constant to help prevent bone blowout during insertion of the fastener 1400.

In some embodiments, the attachment feature, or head 1404, may be located at the proximal end 1401 of the shaft 1405 and configured to be adjustably secured to an implement, such as the radial head component 1420 or a glenoid component (not shown), etc.

In some embodiments, the head 1404 that may be coupled to, or integrally formed with, the proximal end 1401 of the shaft 1405.

In some embodiments, the head 1404 may include a neck portion 1412 and a projection portion 1414.

In some embodiments, the projection portion 1414 may comprise a disc shape.

In some embodiments, the projection portion 1414 may also comprise one or more beveled surfaces 1416.

In some embodiments, the radial head component 1420 (or a glenoid component, etc.) may be coupled to the head 1404 of the fastener 1400 for utilization in a radial head arthroplasty procedure, a glenoid procedure, etc., as shown in FIG. 14I.

In some embodiments, the radial head component 1420 may include a concave articulation surface 1424 that may be configured to receive a convex articulation surface (not shown) to form a prosthetic joint.

In some embodiments, the radial head component 1420 may include an attachment feature 1430.

In some embodiments, the attachment feature 1430 may include a window 1432 that may be sized and shaped to receive the head 1404 and neck portion 1412 of the fastener 1400 therein, as shown in FIG. 14I.

In some embodiments, the attachment feature 1430 may also include one or more set screw holes 1436 configured to receive one or more set screws (not shown) to removably couple the radial head component 1420 to the fastener 1400.

Any of the fasteners described or contemplated herein may be configured for removal and replacement during a revision procedure by simply unscrewing and removing the fastener from the bone/tissue in which the fastener resides. Moreover, the fasteners described herein may advantageously be removed from bone without removing any appreciable amount of bone during the removal process to preserve the bone. In this manner, implants may be mechanically integrated with the bone, while not being cemented to the bone or integrated via bony ingrowth, in order to provide an instant and removable connection between an implant and a bone. Accordingly, revision procedures utilizing the fasteners described herein can result in less trauma to the bone and improved patient outcomes. However, it will also be understood that any of the fasteners described or contemplated herein may also be utilized with cement, as desired.

Any procedures/methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. Moreover, as defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A pedicle bone fastener comprising:
a shaft comprising:
  a proximal end;
  a distal end; and
  a longitudinal axis;
a helical thread disposed about the shaft along the longitudinal axis between the proximal and distal ends of the shaft, the helical thread comprising:
  a first undercut surface; and
  a second undercut surface, wherein:
    the first undercut surface is angled toward one of the proximal end and the distal end of the shaft;

the second undercut surface is angled toward the other one of the proximal end and the distal end of the shaft; and
at least one of the first undercut surface and the second undercut surface comprises a concave crescent shape; and
an integrated attachment feature at the proximal end of the shaft and configured to be adjustably secured to a spinal stabilization implement.

2. The pedicle bone fastener of claim 1, wherein the integrated attachment feature comprises a polyaxial head having a first semi-spherical surface configured to be polyaxially-adjustably secured to the spinal stabilization implement.

3. The pedicle bone fastener of claim 2, wherein the spinal stabilization implement comprises a discrete tulip having a second semi-spherical surface configured to engage the first semi-spherical surface of the polyaxial head to polyaxially-adjustably secure the discrete tulip to the polyaxial head at any of a variety of relative orientations.

4. The pedicle bone fastener of claim 3, wherein the discrete tulip further comprises:
at least one opening; and
a locking member configured to secure a rod receivable through the at least one opening to the discrete tulip.

5. The pedicle bone fastener of claim 1, wherein the integrated attachment feature comprises an integrated tulip having at least one opening configured to receive at least a part of the spinal stabilization implement therethrough.

6. The pedicle bone fastener of claim 5, wherein the spinal stabilization implement comprises a rod receivable through the at least one opening of the integrated tulip.

7. The pedicle bone fastener of claim 6, wherein the integrated tulip further comprises a locking member configured to secure the rod to the integrated tulip.

8. A pedicle fastener stabilization system comprising:
a pedicle bone fastener comprising:
a shaft comprising:
a proximal end;
a distal end; and
a longitudinal axis;
a polyaxial head at the proximal end of the shaft;
a first helical thread disposed about the shaft along the longitudinal axis between the proximal and distal ends of the shaft, the first helical thread comprising a first concave undercut surface oriented toward one of the proximal end and the distal end of the shaft; and
a second helical thread disposed about the shaft adjacent the first helical thread and interposed therebetween, the second helical thread comprising a second concave undercut surface oriented toward the other one of the proximal end and the distal end of the shaft;
a tulip configured to be polyaxially-adjustably secured to the polyaxial head; and
a spinal stabilization rod securable to the tulip.

9. The pedicle fastener stabilization system of claim 8, wherein the polyaxial head is integrally formed with the pedicle bone fastener.

10. The pedicle fastener stabilization system of claim 9, wherein the polyaxial head comprises a first semi-spherical surface.

11. The pedicle fastener stabilization system of claim 10, wherein the tulip comprises a second semi-spherical surface configured to engage the first semi-spherical surface of the polyaxial head to polyaxially-adjustably secure the tulip to the polyaxial head at any of a variety of relative orientations.

12. The pedicle fastener stabilization system of claim 8, wherein the tulip comprises at least one opening configured to receive the spinal stabilization rod therethrough.

13. The pedicle fastener stabilization system of claim 12, wherein the tulip comprises a locking member configured to secure the spinal stabilization rod to the tulip.

14. The pedicle fastener stabilization system of claim 8, wherein a minor diameter of the shaft is constant.

15. A method of implanting a bone fastener assembly comprising:
inserting a bone fastener into a bone, the bone fastener comprising:
a shaft comprising:
a proximal end;
a distal end; and
a longitudinal axis;
a helical thread disposed about the shaft along the longitudinal axis between the proximal and distal ends of the shaft, the helical thread comprising:
a first undercut surface; and
a second undercut surface, wherein:
the first undercut surface is angled toward one of the proximal end and the distal end of the shaft; and
the second undercut surface is angled toward the other one of the proximal end and the distal end of the shaft; and at least one of the first undercut surface and the second undercut surface comprises a concave crescent shape; and
an attachment feature at the proximal end of the shaft configured to be adjustably secured to an implement;
adjusting an orientation of the implement to a selected orientation relative to the attachment feature; and
attaching the implement to the attachment feature at the selected orientation.

16. The method of claim 15, wherein:
the attachment feature at the proximal end of the shaft is configured to be polyaxially-adjustably secured to the implement; and
adjusting the orientation of the implement to the selected orientation relative to the attachment feature further comprises:
polyaxially adjusting the orientation of the implement to a selected relative orientation, of a plurality of polyaxially-differentiated potential relative orientations, relative to the attachment feature.

17. The method of claim 16, wherein:
the attachment feature comprises a polyaxial head having a first semi-spherical surface; and
the implement comprises a discrete tulip having a second semi-spherical surface configured to engage the first semi-spherical surface of the polyaxial head to polyaxially-adjustably secure the discrete tulip to the polyaxial head at any of a variety of relative orientations.

18. The method of claim 17, wherein the discrete tulip comprises:
at least one opening; and
a locking member configured to secure a rod received through the at least one opening to the discrete tulip.

19. The method of claim 15 further comprising:
drilling a pilot hole into the bone; and
inserting the shaft of the bone fastener into the pilot hole.

20. The method of claim 19 further comprising:
tapping a bone thread in the bone to form a tapped bone thread about the pilot hole; and
inserting the helical thread into the tapped bone thread.

* * * * *